(12) United States Patent
Canfield et al.

(10) Patent No.: US 10,383,202 B2
(45) Date of Patent: Aug. 13, 2019

(54) ELECTRONIC FOCAL SPOT ALIGNMENT OF AN X-RAY TUBE

(71) Applicant: Varex Imaging Corporation, Salt Lake City, UT (US)

(72) Inventors: Bradley D Canfield, Orem, UT (US); Michael Meiler, Draper, UT (US); Colton B Woodman, Magna, UT (US); Inwoo Yoon, South Jordan, UT (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 522 days.

(21) Appl. No.: 15/141,191

(22) Filed: Apr. 28, 2016

(65) Prior Publication Data

US 2017/0318651 A1    Nov. 2, 2017

(51) Int. Cl.
*H01J 35/00* (2006.01)
*H05G 1/52* (2006.01)
(Continued)

(52) U.S. Cl.
CPC .............. *H05G 1/52* (2013.01); *A61B 6/035* (2013.01); *A61B 6/584* (2013.01); *H01J 35/06* (2013.01);
(Continued)

(58) Field of Classification Search
CPC ...................................................... H01J 35/14
See application file for complete search history.

(56) References Cited

U.S. PATENT DOCUMENTS

| 5,550,889 A | 8/1996 | Gard |
| 5,566,220 A | 10/1996 | Saito |

(Continued)

FOREIGN PATENT DOCUMENTS

| JP | 2005-143746 | 6/2005 |
| JP | 2008 159317 | 7/2008 |

(Continued)

OTHER PUBLICATIONS

EPO Search Report for Varex Imaging Corp.'s EP 17168100.0-1556 dated Sep. 26, 2017.
(Continued)

*Primary Examiner* — Dani Fox
(74) *Attorney, Agent, or Firm* — Laurence & Phillips IP Law

(57) ABSTRACT

Technology is described for electronically aligning a central ray of an x-ray tube to a radiation detector. In an example, an x-ray system includes an x-ray tube and a tube control unit (TCU). The x-ray tube includes a cathode that includes an electron emitter configured to emit an electron beam, an anode configured to receive the electron beam and generate x-rays with a central ray from electrons of the electron beam colliding on a focal spot of the anode, and a steering magnetic multipole between the cathode and the anode that is configured to produce a steering magnetic field from a steering signal. At least two poles of the steering magnetic multipole are on opposite sides of the electron beam. The TCU includes at least one steering driver configured to generate the steering signal. The TCU is configured to convert an offset value to the steering signal.

24 Claims, 37 Drawing Sheets

(51) Int. Cl.
*H01J 35/14* (2006.01)
*H01J 35/06* (2006.01)
*H01J 35/08* (2006.01)
*A61B 6/03* (2006.01)
*A61B 6/00* (2006.01)
*H01J 35/30* (2006.01)

(52) U.S. Cl.
CPC .............. *H01J 35/08* (2013.01); *H01J 35/14* (2013.01); *A61B 6/54* (2013.01); *A61B 6/582* (2013.01); *H01J 35/305* (2013.01)

(56) References Cited

U.S. PATENT DOCUMENTS

| | | | |
|---|---|---|---|
| 2005/0094762 A1 | 5/2005 | Dunham | |
| 2011/0150187 A1* | 6/2011 | Boudry | H05G 1/46 378/207 |
| 2015/0187530 A1 | 7/2015 | Canfield | |
| 2015/0187536 A1 | 7/2015 | Canfield | |
| 2015/0187537 A1 | 7/2015 | Canfield | |
| 2015/0187538 A1 | 7/2015 | Canfield | |

FOREIGN PATENT DOCUMENTS

| | | |
|---|---|---|
| JP | 2009 142349 | 7/2009 |
| JP | 2010 005015 | 1/2010 |
| JP | 2012-196327 | 10/2012 |
| JP | 2012-234810 | 11/2012 |
| WO | WO2015066246 | 5/2015 |

OTHER PUBLICATIONS

Translation of Office Action in JP 2017-087406 dated Feb. 19, 2018.
Translation of Office Action in JP 2017-089466 dated Jun. 14, 2018.
Office Action in U.S. Appl. No. 15/141,240 dated Sep. 19, 2018.
Response to Office Action in U.S. Appl. No. 15/141,240 dated Jan. 21, 2019.

* cited by examiner

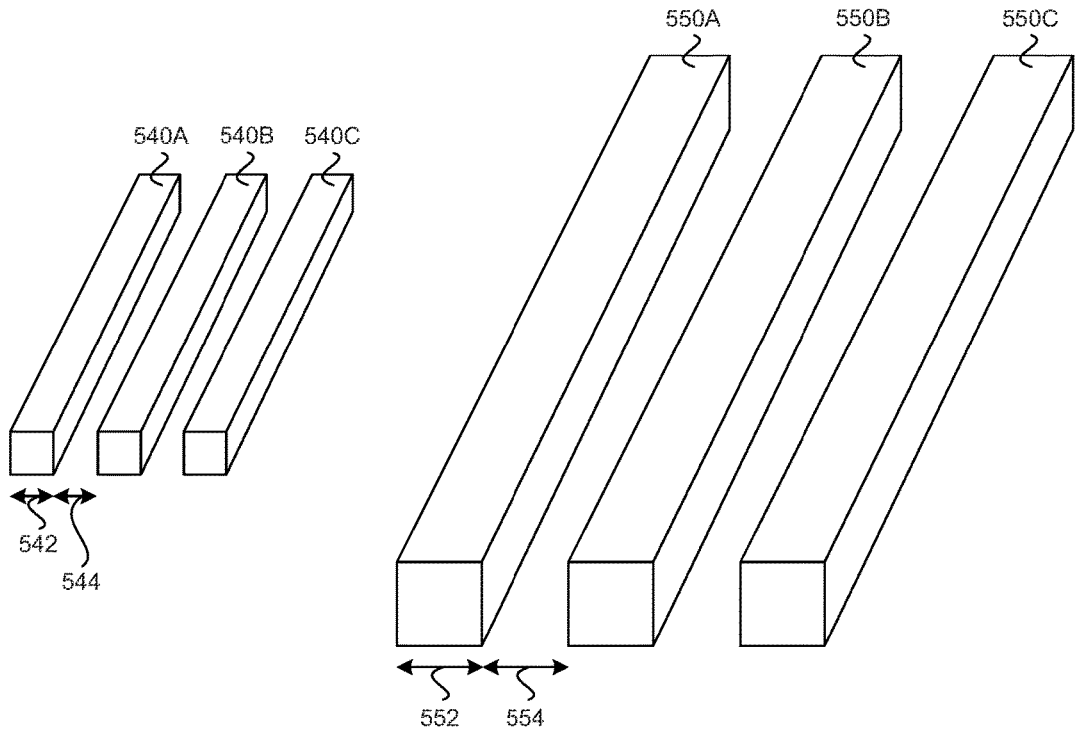
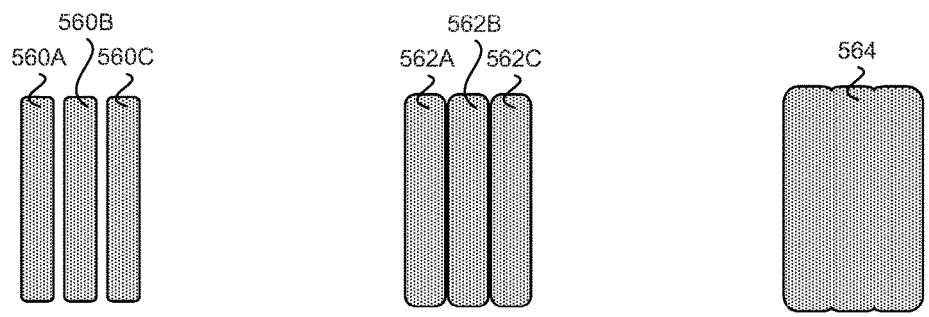
FIG. 29C     FIG. 29D     FIG. 29E

ELECTRONIC FOCAL SPOT ALIGNMENT OF AN X-RAY TUBE

BACKGROUND

Unless otherwise indicated herein, the approaches described in this section are not prior art to the claims in this disclosure and are not admitted to be prior art by inclusion in this section.

An x-ray system typically includes an x-ray tube and an imager (or detector). The power and signals for the x-ray tube can be provided by a high voltage generator. The x-ray tube emits radiation, such as x-rays, toward an object. The object is positioned between the x-ray tube and the imager. The radiation typically passes through the object and impinges on the imager. As radiation passes through the object, internal structures of the object cause attenuation in the radiation received at the imager. The imager then generates data based on the detected radiation, and the system translates or reconstructs the radiation attenuations into an image with spatial variances, which may be used to evaluate the internal structure of the object, such as a patient in a medical imaging procedure or an inanimate object in an inspection scan.

The x-ray tube includes a cathode and an anode. X-rays are produced in x-ray tubes by applying an electrical current to a filament positioned within the cathode to cause electrons to be emitted from the cathode by thermionic emission. In a vacuum, the electrons accelerate towards and then impinge upon the anode due to the voltage difference between the cathode and the anode. When the electrons collide with a target on the anode, some of the energy is emitted as x-rays, and the majority of the energy is released as heat. The area on the anode in which the electrons collide is generally known as the focal spot, and the emitted x-rays can have a central ray (i.e., central ray beam, central x-ray beam, center ray beam, center x-ray beam, or center ray) emanating from the focal spot, and the central ray represents a point area in x-ray beam with a high intensity. A focal spot size can be determined by an x-ray system design, an x-ray tube structure, a tube voltage (e.g., with units of kilovolts [kV]), and a tube current (e.g., with units of milliamps [mA]). Because of high temperatures generated when the electron beam strikes the target, specifically the focal spot, the anode can include features to distribute the heat generated at the focal spot on the target, such as rotating a disc-shaped anode target at a high rotational speed. A rotating anode typically includes the disc-shaped anode target, which is rotated by an induction motor via a bearing assembly.

The radiation imager (e.g., x-ray detector, x-ray imager, or radiation detector) can include a conversion element that converts an incoming radiation beam into electrical signals, which can be used to generate data about the radiation beam, which in turn can be used to characterize an object being inspected (e.g., the patient or inanimate object). In one example, the conversion element includes a scintillator that converts a radiation beam into light, and a sensor that generates electrical signals in response to the light. The imager can also include processing circuitry that processes the electrical signals to generate data about the radiation beam.

The x-ray tube and radiation imager can be components in an x-ray system, such as a computed tomography (CT) system or scanner, which includes a gantry that rotates both the x-ray tube and the imager to generate various images of the object at different angles. The CT scanner may also include a collimator to limit the exposure area of the emitted x-rays. A collimator is a device that narrows a beam of particles or waves (e.g., x-rays) to cause the directions of the beam to become more aligned in a specific direction or to cause the spatial cross section of the beam to become smaller. The x-ray tube, the radiation imager, the collimator, and the generator can be separate components that are attached to the gantry.

Conventionally, to ensure image quality, good accuracy, and high resolution, the x-ray tube is mechanically aligned to the gantry and the collimator so the central ray of the x-ray tube is centered on a specified location on the detector (e.g., center point on the detector). Mechanical alignment of the x-ray tube on the gantry can be time consuming, cumbersome, and iterative, especially for fine tune adjustments (e.g., sub millimeter range). For example, to achieve the correct positioning of the x-ray tube, a series of images can be taken and the central ray representing the focal spot location can be determined from the images. Subsequently, the x-ray tube can be adjusted and another series of images can be taken to determine the focal spot position (or central ray). The x-ray tube is adjusted and the sequence is repeated again until a satisfactory alignment of the x-ray tube relative to the detector is achieved.

The technology (systems, devices, and methods) described herein provides alternatives to mechanical alignment, especially for fine tune adjustments of the focal spot position, and thus the central ray.

BRIEF SUMMARY OF SOME EXAMPLE EMBODIMENTS

Electronic focal spot alignment (or central ray alignment) refers to the technology (systems, devices, and methods) described herein that provides alternatives to mechanical alignment, especially for fine tune adjustments of the focal spot position, and thus the central ray. Electronic focal spot alignment can provide an automated and more accurate adjustment of the x-ray tube to radiation detector than just a mechanical alignment after a course mechanical alignment is performed. Electronic focal spot alignment can reduce the time to align the x-ray tube to the gantry and the radiation detector as well as providing a more accurate alignment. Electronic focal spot alignment uses steering coils of x-ray tube magnetics and tube control unit (TCU) electronics to adjust a focal spot on a focal track on the anode, which generates x-rays with a central ray that can be aligned with the imaging system (e.g., the radiation detector) of the x-ray system. In an example, the focal spot can be moved in two dimensional (2D) space utilizing a 2D beam steering or deflection mechanism that acts on the electron beam. By adding offset values to the signals that generate the steering directions, the focal spot can be adjusted to align the central ray with the imaging system.

Another example provides a method of aligning a central ray of an x-ray tube to a radiation detector using a tube control unit (TCU). The method includes the operation of emitting electrons from an emitter in an x-ray tube. The next operation of the method can include generating x-rays with a central ray from the electrons colliding on a focal spot of an anode of the x-ray tube. The method can further include receiving, at the TCU, an offset value representing a distance of the central ray from a specified imager location. The next operation of the method can include generating a steering signal from at least one steering driver of the TCU based on the offset value that is applied to a steering magnetic multipole between the emitter and the anode on an x-ray tube. The method can further include moving the focal spot on the anode with the steering magnetic multipole to align the central ray to the specified imager location. At least two poles of the steering magnetic multipole are on opposite sides of a path of the electrons. In a configuration, the specified imager location represents an align position of the radiation imager.

In an example, the operation of generating the steering signal includes: summing the offset value and steering position calibration data, and combining the sum of the offset value and the steering position calibration data with steering driver calibration data. The steering position calibration data represent current values to generate at least one steering position using the steering magnetic multipole for a tube voltage and tube current combination. The steering driver calibration data represent current values of the at least one steering driver.

In another example, the operation of generating the steering signal includes: determining a position change of the central ray from the specified imager location, calculating a deflection value using steering position calibration data, and summing the offset value representing a static position change of the central ray and the deflection value representing a dynamic position change of the central ray. The method can further include saving the offset value in an offset table.

In a configuration, the method can further include generating a focusing signal from at least one focusing driver of the TCU that is applied to a focusing magnetic multipole between the emitter and anode on the x-ray tube, and narrowing an area of the focal spot on the anode with the focusing magnetic multipole. The operation of generating the focusing signal can further include: receiving tube calibration data from the x-ray tube, and combining the tube calibration data and focus driver calibration data. The tube calibration data represent current values to generate a specified focal spot size for the x-ray tube. The focus driver calibration data represent current values of at least one focus driver.

Prior to receiving the offset value, in another configuration, the method can further include: receiving, at a system control unit, image data from a radiation imager including a central ray position on the radiation imager, calculating the offset value based on a center ray position relative to the specified imager location, and sending the offset value to the TCU. Also prior to receiving the offset value, the method can further include: detecting x-rays, converting detected x-rays into image data that includes a central ray position, and sending the image data to the system control unit.

In another example, an x-ray system includes an x-ray tube and a tube control unit (TCU). The x-ray tube includes a cathode that includes an electron emitter configured to emit an electron beam, an anode configured to receive the electron beam and generate x-rays with a central ray from electrons of the electron beam colliding on a focal spot of the anode, and a steering magnetic multipole between the cathode and the anode that is configured to produce a steering magnetic multipole field from a steering signal. At least two poles of the steering magnetic multipole are on opposite sides of the electron beam. The steering magnetic multipole field moves a focal spot of the electron beam on the anode. The TCU includes at least one steering driver configured to generate the steering signal. The TCU is configured to convert a offset value to the steering signal. The offset value represents a distance of the central ray from a specified detector location.

In an example, the x-ray system includes a system control unit configured to: receive image data from a radiation imager that includes a central ray position, calculate the offset value based on a center ray position relative to the specified imager location, and send the offset value to the TCU. In another example, the x-ray system includes an x-ray imager configured to: detect x-rays, convert detected x-rays into image data that includes a central ray position, and send the image data to the system control unit.

In a configuration, the steering magnetic multipole has a steering yoke with at least two evenly distributed pole projections extending from the steering yoke and oriented toward a central axis of the steering yoke. Each of the at least two pole projections having a steering electromagnetic coil operably coupled to the at least one steering driver that provides a current to each steering electromagnetic coil to produce a steering magnetic field.

In another configuration, the steering magnetic multipole includes at least two sets of steering magnetic dipoles that provide two dimensional (2D) steering of the focal spot. A first set of the steering magnetic dipoles include two poles on opposite sides of the electron beam and a second set of the steering magnetic dipoles include another two poles on opposite sides of the electron beam. A first path of magnetic flux from between the two poles of the first set of the steering magnetic dipoles is substantially orthogonal to a second path of magnetic flux from between the two poles of the second set of the steering magnetic dipoles. The at least one steering driver includes at least one horizontal driver configured to generate the steering signal to the two poles and at least one vertical driver configured to generate the steering signal to the other two poles.

In another example, the steering magnetic multipole includes two sets of steering magnetic dipoles that have a steering yoke with four evenly distributed steering pole projections extending from the steering yoke and oriented toward a central axis of the steering yoke. Each of the four steering pole projections having a steering electromagnetic coil operably coupled to the at least one steering driver that provides a current to each steering electromagnetic coil to produce a steering magnetic field.

In another configuration, the x-ray tube includes a focusing magnetic multipole between the cathode and the steering magnetic multipole that is configured to produce a focusing magnetic field from a focusing signal. The focusing magnetic field narrows the electron beam on a focal track of the anode. The TCU includes at least one focusing driver configured to generate the focusing signal. The TCU can also include focus driver calibration data representing current values of at least one focus driver. The focusing signal can include the focus driver calibration data partially iterated with tube calibration data representing current values to generate a specified focal spot size for the x-ray tube a tube voltage and tube current combination. In another example, the focusing magnetic multipole is disposed on the steering magnetic multipole. The steering magnetic multipole is also configured to produce the focusing magnetic field.

In another example, the TCU includes: steering driver calibration data representing current values of the at least one steering driver, and steering position calibration data representing current values to generate at least one steering position using the steering magnetic multipole for a tube voltage and tube current combination. The steering signal includes the offset value added to the steering position calibration data and is partially iterated with the steering driver calibration data. The steering position calibration data can include multiple steering positions in which other steering positions can be calculated. In a configuration, the x-ray system includes a computerized tomography (CT) scanner or a rotational x-ray system and the x-ray system includes a gantry configured to receive the x-ray tube and the TCU.

In another example, a tube control unit (TCU) is configured to align an x-ray tube to an x-ray imager. The TCU includes at least one steering driver, memory, and a processor. The at least one steering driver is configured to generate a steering signal for at least one steering coil of a steering magnetic multipole for an x-ray tube. The memory is configured to store steering position calibration data representing current values to generate at least one steering position using the steering magnetic multipole for a tube voltage and tube current combination. The processor is configured to: generate an offset value representing a distance of a central ray of the x-ray tube from a specified imager location of an x-ray imager, generate a deflection value using the steering position calibration data, and sum the offset value representing a static position change of the central ray and the deflection value representing a dynamic position change of the central ray.

In a configuration, the memory is configured to store the steering driver calibration data that represent current values of the at least one steering driver. The processor is configured to combine the sum of the offset value and the deflection value with the steering driver calibration data.

In another configuration, the TCU includes at least one focusing driver configured to generate a focusing signal for at least one focusing coil of a focusing magnetic multipole for the x-ray tube. The memory is configured to: store focus driver calibration data that represent current values of the at least one focusing driver, and store tube calibration data representing current values to generate a specified focal spot size for the x-ray tube. The processor is configured to combine the tube calibration data and the focus driver calibration data.

The summary provided above is illustrative and is not intended to be in any way limiting. In addition to the examples described above, further aspects, features, and advantages of the invention will be made apparent by reference to the drawings, the following detailed description, and the appended claims.

BRIEF DESCRIPTION OF THE DRAWINGS

FIGS. 29A-B illustrate examples of line shape phantoms for alignment or tolerance determination.

FIGS. 29C-E illustrate example images of the line shape phantoms shown in FIGS. 29A-B.

DETAILED DESCRIPTION OF SOME EXAMPLE EMBODIMENTS

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Numbers provided in flow charts and processes are provided for clarity in illustrating steps and operations and do not necessarily indicate a particular order or sequence. Unless otherwise defined, the term "or" can refer to a choice of alternatives (e.g., a disjunction operator, or an exclusive or) or a combination of the alternatives (e.g., a conjunction operator, and/or, a logical or, or a Boolean OR).

The invention relates generally to electronic focal spot alignment (or central ray alignment) to a radiation imaging system (e.g., x-ray detector) and, more particularly, to various methods and components for electronic focal spot alignment in a rotating x-ray system, such as a computed tomography (CT) system.

Example embodiments illustrate components and features in an x-ray system, such as an x-ray tube, a tube control unit (TCU), system control unit, and radiation detector (e.g., x-ray detector), for aligning a central ray of the x-ray tube to the radiation detector. In particular, example two dimensional steering magnetic multipoles and offset values can be used to align the focal spot position and the central ray, which can improve the accuracy and speed of aligning an x-ray tube to the radiation imaging system or gantry.

Reference will now be made to the drawings to describe various aspects of example embodiments of the invention. It is to be understood that the drawings are diagrammatic and schematic representations of such example embodiments, and are not limiting of the present invention, nor are they necessarily drawn to scale. In some drawings, features are exaggerated to visually illustrate concepts or principles.

Example X-Ray Tube

Figure 1:
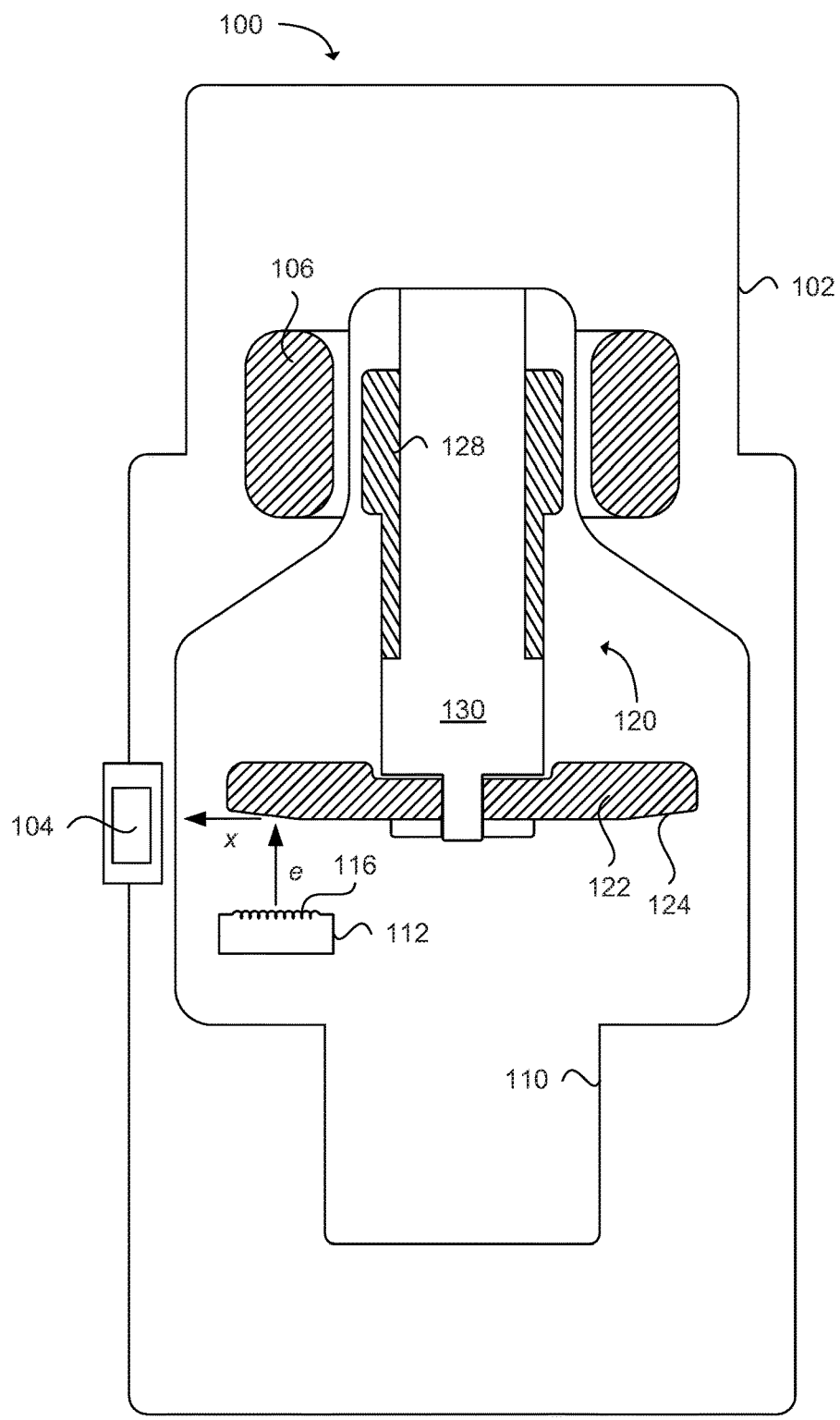
FIG. 1 illustrates a block diagram of an example x-ray tube.

FIG. 1 is a block diagram of an example rotary or rotating anode type x-ray tube 100 with a rotatable disc-shaped anode 122. The x-ray tube 100 includes a housing 102 and an x-ray insert 110 within the housing 102. The housing 102 encloses the insert 110. A coolant or air may fill the space or cavity between the housing 102 and the insert 110. A cathode 112 and an anode assembly 120 are positioned within an evacuated enclosure, also referred to as the insert 110. The anode assembly 120 includes the anode 122, a bearing assembly 130, and a rotor 128 mechanically coupled to the bearing assembly 130. The anode 122 is spaced apart from and oppositely disposed to the cathode 112. The anode 122 and cathode 112 are connected in an electrical circuit that allows for the application of a high voltage potential between the anode 122 and the cathode 112. The cathode 112 includes an electron emitter 116 (an emission source) that is connected to an appropriate power source (not shown).

As disclosed in FIG. 1, prior to operation of the example x-ray tube 100, the insert 110 is evacuated to create a vacuum. The insert 110 encloses the vacuum. Then, during operation of the example x-ray tube 100, an electrical current is passed through the electron emitter 116 of the cathode 112 to cause electrons "e" to be emitted from the cathode 112 by thermionic emission. The application of a high voltage differential between the anode 122 and the cathode 112 then causes the electrons "e" to accelerate from the cathode electron emitter toward a focal spot on a focal track 124 that is positioned on the anode 122. The focal track 124 may be composed for example of tungsten (W) and rhenium (Re) or other materials having a high atomic ("high Z") number. As the electrons "e" accelerate, they gain a substantial amount of kinetic energy, and upon striking the rotating focal track 124 some of this kinetic energy is converted into x-rays "x".

The focal track 124 is oriented so that emitted x-rays "x" are visible to an x-ray tube window 104. The x-ray tube window 104 includes an x-ray transmissive material, such as beryllium (Be), so the x-rays "x" emitted from the focal track 124 pass through the x-ray tube window 104 in order to strike an intended object (not shown) and then the detector to produce an x-ray image (not shown). FIG. 1 illustrates a single window 104 on the housing 102 (e.g., with a glass insert that allows radiation to pass through the glass, beryllium, or aluminum of the glass insert). In other examples, a separate window may be included on both the insert 110 (e.g., a metal insert) and the housing 102, or a window may be included on just the insert 110.

X-radiation (composed of x-rays) refers to a form of electromagnetic radiation. Most X-rays have a wavelength ranging from 0.01 to 10 nanometers (nm), corresponding to frequencies in the range 30 petahertz to 30 exahertz ($3\times10^{16}$ Hertz [Hz] to $3\times10^{19}$ Hz) and energies in the range 100 electron volt (eV) to 100 kilo electron volt (eV).

As the electrons "e" strike the focal track 124, a significant amount of the kinetic energy of the electrons "e" is transferred to the focal track 124 as heat. To reduce the heat at a specific focal spot on the focal track 124, a disc-shaped anode target is rotated at high speeds, typically using an induction motor that includes a rotor 128 and a stator 106. The induction motor is an alternating current (AC) electric motor in which the electric current in the rotor 128 needed to produce torque is obtained by electromagnetic induction from a magnetic field created by current running through the stator winding. Then, the rotor 128 rotates a hub of the bearing assembly 130 that is mechanically coupled to the anode 122, which rotates the anode 122. In other examples (not shown), the x-ray tube uses a stationary track.

After the x-rays are emitted from the x-ray tube, the x-rays strike or transmit through an intended object (e.g., the patient or inanimate object) and then the radiation detector to produce an x-ray image. The radiation detector includes a matrix or array of pixel detector elements. The pixel detector elements (e.g., x-ray detector element or detector element) refers to an element in a matrix or array that converts x-ray photons to electrical charges. A detector element may include a photoconductor material which can convert x-ray photons directly to electrical charges (electron-hole pairs) in a direct detection scheme. Suitable photoconductor materials include and are not limited to mercuric iodide ($HgI_2$), lead iodide ($PbI_2$), bismuth iodide ($BiI_3$), cadmium zinc telluride (CdZnTe), or amorphous selenium (a-Se). In some embodiments, a detector element may comprise a scintillator material which converts x-ray photons to light and a photosensitive element coupled to the scintillator material to convert the light to electrical charges (i.e., indirect detection scheme). Suitable scintillator materials include and are not limited to gadolinium oxisulfide ($Gd_2O_2S$:Tb), cadmium tungstate ($CdWO_4$), bismuth germanate ($Bi_4Ge_3O_{12}$ or BGO), cesium iodide (CsI), or cesium iodide thallium (CsI:Tl)). Suitable photosensitive element may include a photodiode, a photogate, or phototransistors. Other circuitry for pixel detector elements may also be used.

Example Gantry

The x-ray tube and radiation detector can be included in a rotational x-ray system, such as a computerized tomography (CT) scanner. Computerized tomography (CT) involves the imaging of the internal structure of an object by collecting several projection images ("radiographic projections") in a single scan operation ("scan"), and is widely used in the medical field to view the internal structure of selected portions of the human body. Typically, several two-dimensional projections are made of the object, and a three-dimensional representation of the object is constructed from the projections using various tomographic reconstruction methods. From the three-dimensional image, conventional CT slices (e.g., 16 or 64 slices per gantry rotation) through the object can be generated. The two-dimensional projections are typically created by transmitting radiation from a "point source" (e.g., x-ray tube) through the object, which will absorb some of the radiation based on its size, density, and atomic composition, and collecting the non-absorbed radiation onto a two-dimensional imaging device or imager (i.e., radiation imager or radiation detector), which comprises an array of pixel detectors (simply called "pixels"). Such a CT system is shown in FIG. 2.

Figure 2:
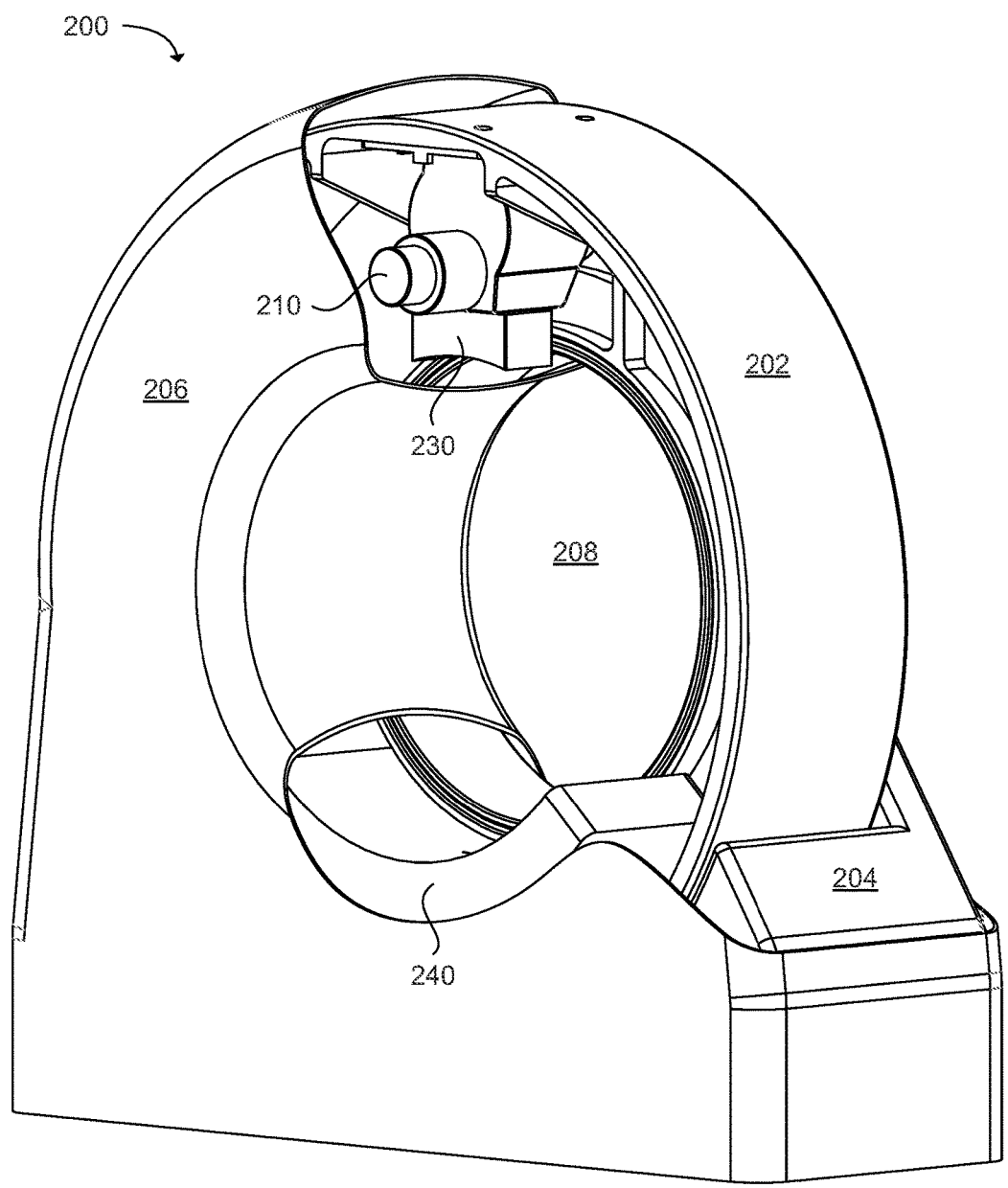
FIG. 2 illustrates a perspective view of a partially exposed example gantry assembly.

FIG. 2 illustrates a partially exposed rotating assembly (or gantry assembly) 200, or gantry, of a rotating x-ray system (or rotational x-ray system). The gantry includes a stationary gantry frame 204 that supports a rotatable gantry frame 202. The rotatable gantry can support an x-ray tube 210, a collimator 230, and a radiation detector or imager 240. Alternatively, the collimator can be coupled directly to the x-ray tube. The gantry also includes a gantry cover 206 to shield the rotating components and frame from a user as well as provide an aesthetic covering. The rotatable gantry frame can include an annular shape (i.e., ring shape) that rotates at a high speed about a center of axis (i.e., central axis) in a gantry aperture 208 of the rotatable gantry frame. The centrifugal force (or gantry force) on components disposed on the rotatable gantry frame can experience a high force, which can exceed a gravitational force (g-force, G's, or G loads) or a multiple of the g-force (e.g., 20 times the g-force). In other examples not shown, the rotatable gantry frame may rotate less than a full revolution, such as rotation of 180° or greater in a C-arm scanner.

X-Ray Tube Mechanical Alignment

Conventionally, as previously described, the x-ray tube is mechanically aligned to the gantry and the collimator so the central ray of the x-ray tube is centered on a specified location on the detector (e.g., center point on the detector) based on movement of the x-ray tube. Alignment of the x-ray tube is used to ensure image quality, good accuracy, and high resolution. Mechanical alignment or adjustments—repositioning of the x-ray tube—to achieve alignment, especially for higher precision of the central ray can be time consuming, cumbersome, iterative, and the quality of the alignment can be highly dependent on the skill of the technician performing the mechanical alignment. In some mechanical alignment processes, the central ray is aligned by moving the x-ray tube and collimator.

Figure 3:
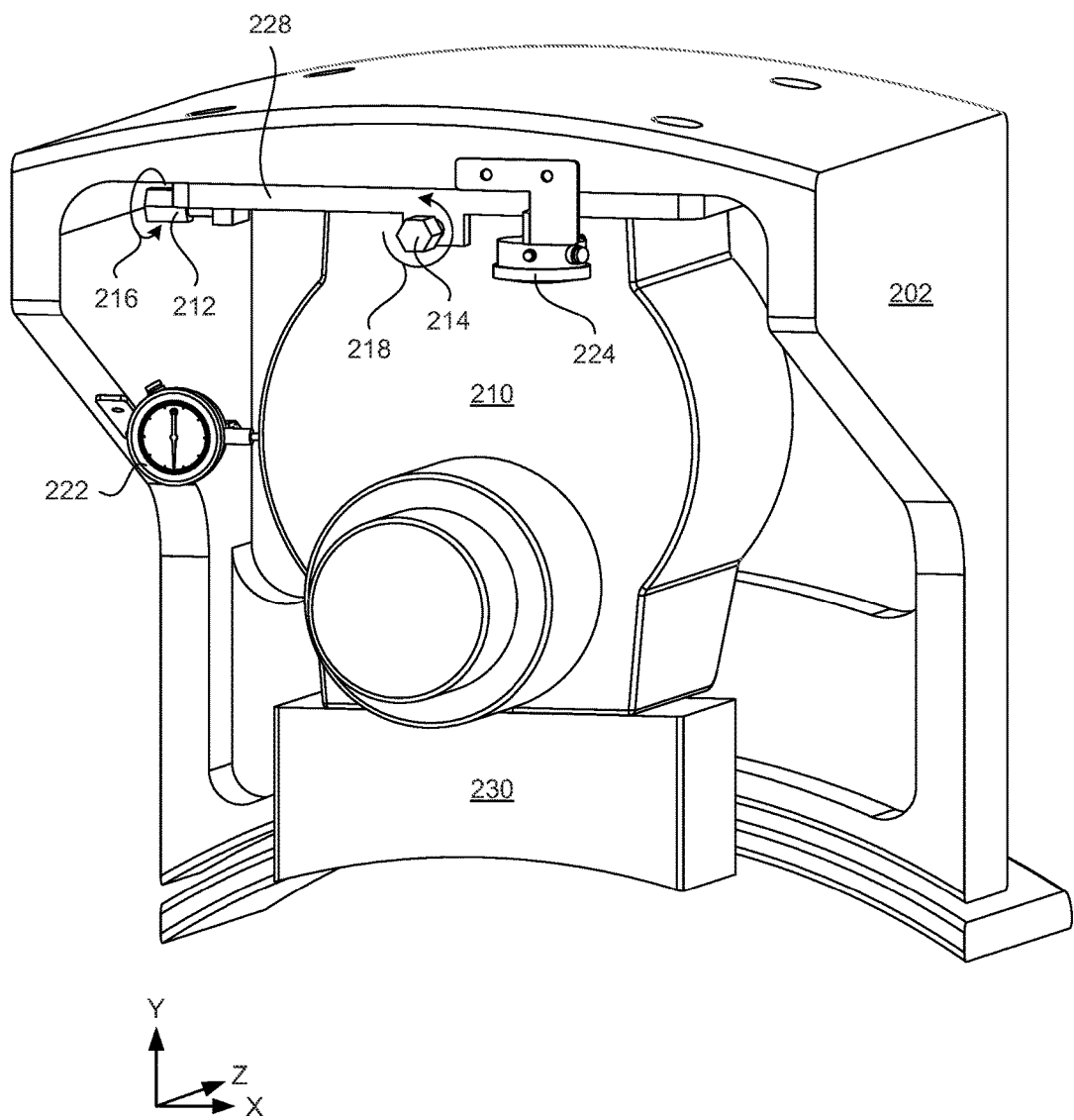
FIG. 3 illustrates a perspective view of an example x-ray tube and a collimator coupled to a rotatable gantry frame.

FIG. 3 illustrates an expanded view of the x-ray tube 210 and the collimator 230 mounted to the rotatable gantry frame 202 via an x-ray tube mounting bracket 228. For descriptive purposes, FIG. 3 provides a Cartesian coordinate system with the y-axis in the radial direction from center of axis of the gantry (e.g., the vertical direction in FIG. 3), the x-axis is in the circumferential direction around the center of axis of the gantry (e.g., the horizontal direction in FIG. 3) and orthogonal to the y-axis, and the z-axis is orthogonal to the x-y plane in the axial direction. The rotation of the gantry occurs in the x-y plane. The x-ray tube mounting bracket provides two dimensional (2D) adjustment of the x-ray tube in the x-z plane. An x-axis adjustment nut, bolt, turret, or knob 212 provides adjustment of the x-ray tube in the x-axis based on an x-axis adjustment nut rotation 216. An x-axis indicator or dial 222 can indicate a change in position in the x-direction of the x-ray relative to the rotatable gantry frame 202 or collimator 230 with micrometer type measurements. Similarly, a z-axis adjustment nut, bolt, turret, or knob 214 provides adjustment of the x-ray tube in the z-axis based on a z-axis adjustment nut rotation 218. A z-axis indicator or dial 224 can indicate a change in position in the z-direction of the x-ray relative to the rotatable gantry frame 202 or collimator 230 with micrometer type accuracy.

With an aligned x-ray tube 210 to the rotatable gantry frame 202, a point source (e.g., x-ray tube) and a center of the two-dimensional imager (e.g., x-ray detector 240) lie on a common axis (i.e., a y-axis), which may be called the projection axis. The source's radiation (e.g., x-rays) emanates toward the imaging device in a volume of space defined by a right-circular, elliptical, or rectangular cone (based on the collimator used) having its vertex at the point source and its base at the imaging device with a central ray emanating from the vertex representing the center point of the x-radiation.

Figure 4:
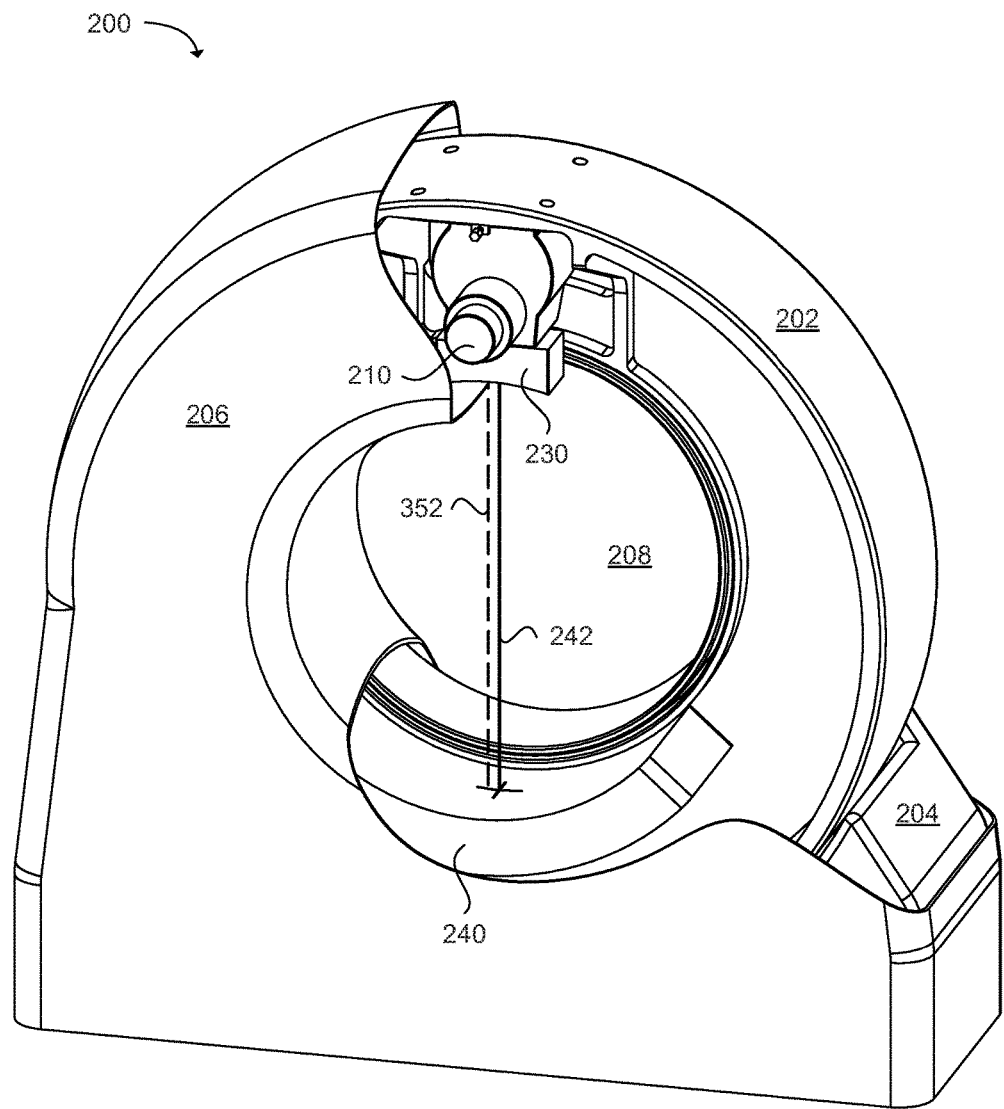
FIG. 4 illustrates a perspective view of a partially exposed example gantry assembly showing a geometric center point of an x-ray detector relative to a central x-ray beam.
Figure 5:
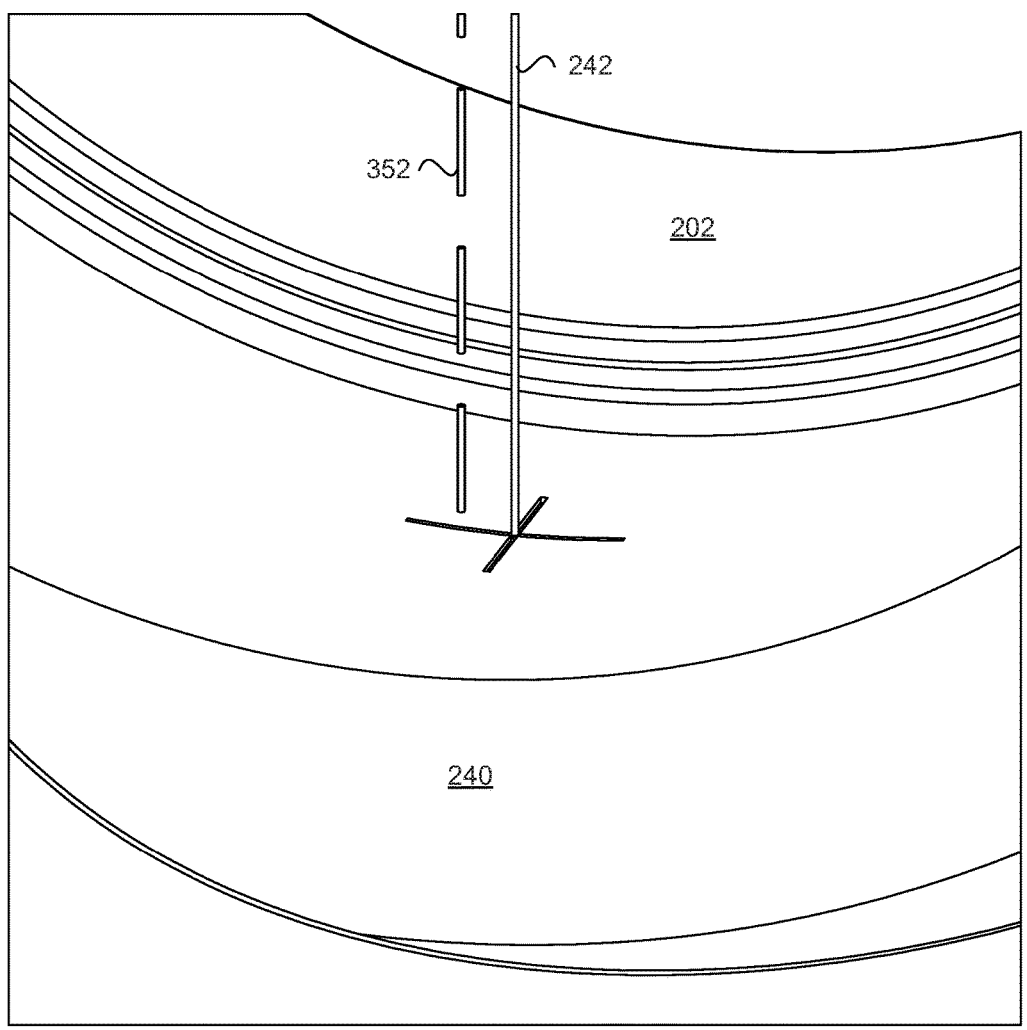
FIG. 5 illustrates an expanded perspective view of an example x-ray detector relative to a central x-ray beam.
Figure 6:
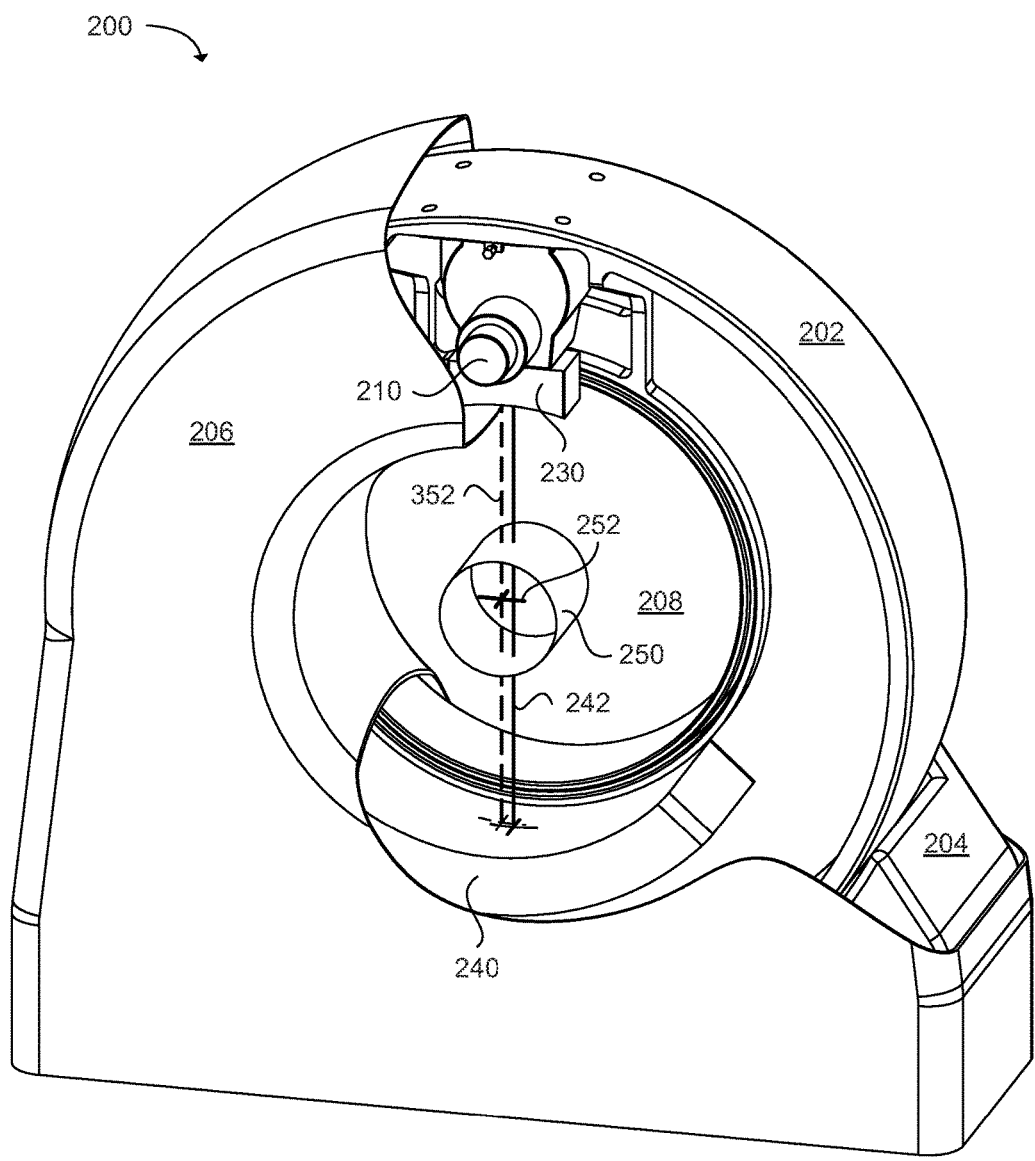
FIG. 6 illustrates a perspective view of a partially exposed example gantry assembly and object showing a geometric center point of an x-ray detector relative to a central x-ray beam.

FIGS. 4 and 5 illustrate a gantry assembly showing an x-ray detector geometric center point 242 relative to a central x-ray beam 352. FIG. 6 illustrates an object feature 252 (or phantom) of an object used to determine the central ray location on the x-ray detector. Initially when the x-ray tube 210 is installed on the rotatable gantry frame 202, the central ray is usually misaligned with the x-ray detector geometric center point (or other specified imager location), as shown. An alignment process moves the central ray to the x-ray detector geometric center point within a specified tolerance.

Conventionally, the alignment process is entirely mechanical, which mechanical alignment moves the x-ray tube 210 relative to the rotatable gantry frame 202, so the central ray 352 is located at the x-ray detector geometric center point 242 within the specified tolerance. While coarse mechanical alignment (e.g., within ±0.5 to 0.1 millimeter [mm]) can be achieved with proper fixturing of the x-ray tube mounting bracket 228 or the x-ray tube 210, fine mechanical alignment can be based on an iterative process by which images or data are acquired and the tube or collimator orientation is adjusted mechanically using adjustment tools (e.g., wrenches or adjustment nuts, bolts, turrets, or knobs 212 and 214) and measuring devices (e.g., indicators or dials 222 and 224 or micrometers).

For high resolution images, fine adjustments in the sub millimeter range down to micrometers can be needed. In order to achieve the correct positioning of the central ray 352 (representing the x-ray tube position), a series of images are taken and the central ray is determined. Subsequently, the x-ray tube is adjusted and another series of images is taken to determine the position. The central ray or x-ray tube is adjusted and the sequence is repeated until a satisfactory alignment is achieved.

Figure 7:
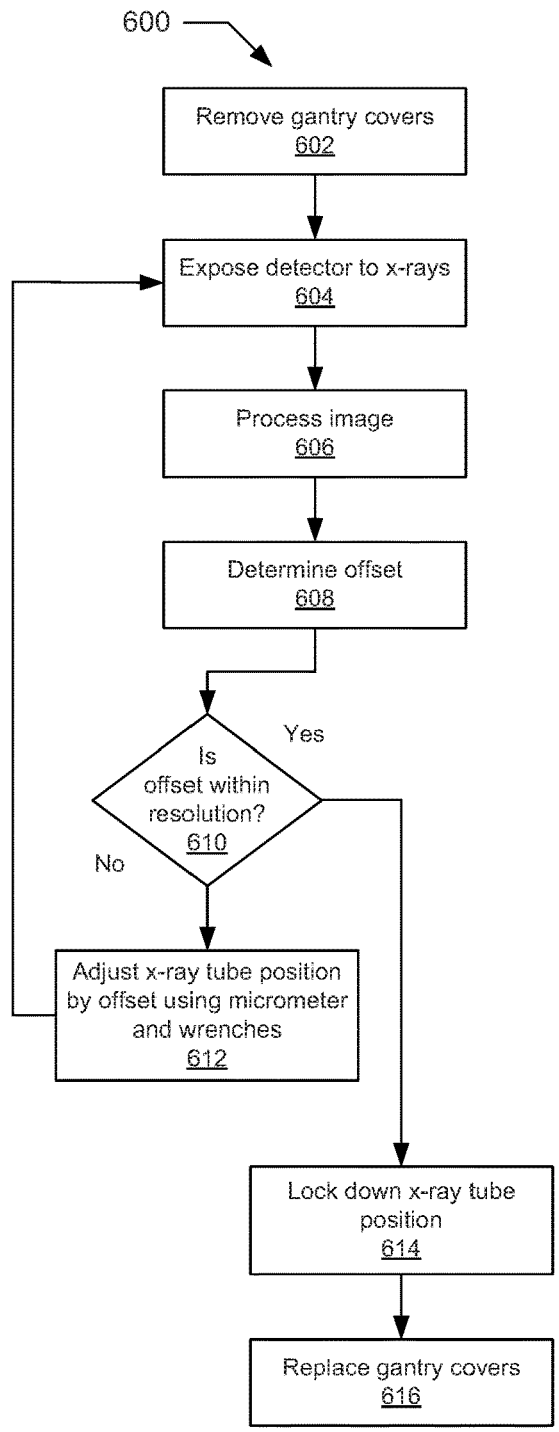
FIG. 7 illustrates a flowchart for an example mechanical alignment of a central x-ray beam.

FIG. 7 illustrates an example flowchart of the mechanical alignment 600 of the x-ray tube, which aligns the central x-ray beam to a specified imager location. The user (e.g., operator or technician) removes the gantry covers 602, which exposes the rotatable gantry frame. The imager or detector is exposed to x-rays from the x-ray tube 604, usually with an alignment object or phantom. The image of the x-ray detector is processed 606 by a processor in the x-ray detector or a system control unit to generate a central x-ray beam position on the detector from which an offset representing a distance of the central ray from the specified imager location (e.g., the x-ray detector geometric center point) is determined 608. The offset can represent a 2D distance in the x-z plane (i.e., with an x-axis component and a z-axis component). The user (or automated process or robot) determines if the offset is within an acceptable tolerance or precision (e.g., <50-200 microns [μm or micrometers]) 610. If the offset is not within an acceptable tolerance or precision, the x-ray tube is adjusted by the offset in the x-direction, z-direction, or both using adjustment tools (e.g., nuts, bolts, turrets, knobs, or wrenches) and measuring devices (e.g., indicators, dials, or micrometers) 612. The detector is again exposed to x-rays 604, and the process repeats until the offset is within the acceptable tolerance or precision. Once the offset is within an acceptable tolerance or precision, the user locks down the x-ray tube position 614 with fasteners (not shown; e.g., screws, nuts, bolts, turrets, or knobs) and replaces the gantry covers 616. Due to the high precision of the fine mechanical alignment, the iterative adjustment of the x-ray tube or collimator can take over ½ to 1 hour to complete. The time to perform a fine mechanical alignment can increase as the acceptable tolerance or precision becomes smaller.

X-Ray Tube Electronic Alignment

Using electronic alignment for the fine alignment can remove the iterative steps in the manual adjustment process, which can save time in calibrating the x-ray tube to the gantry assembly. The coarse mechanical alignment can be performed with relative ease and in a relatively short duration of time, as previously discussed, and the subsequent iterative process of the fine alignment can be performed by an electronic alignment process (i.e., adjustment of the current going to the magnetic coils and resulting magnetic forces on the electron beam in the x-ray tube), thereby saving time and money.

Figure 8:
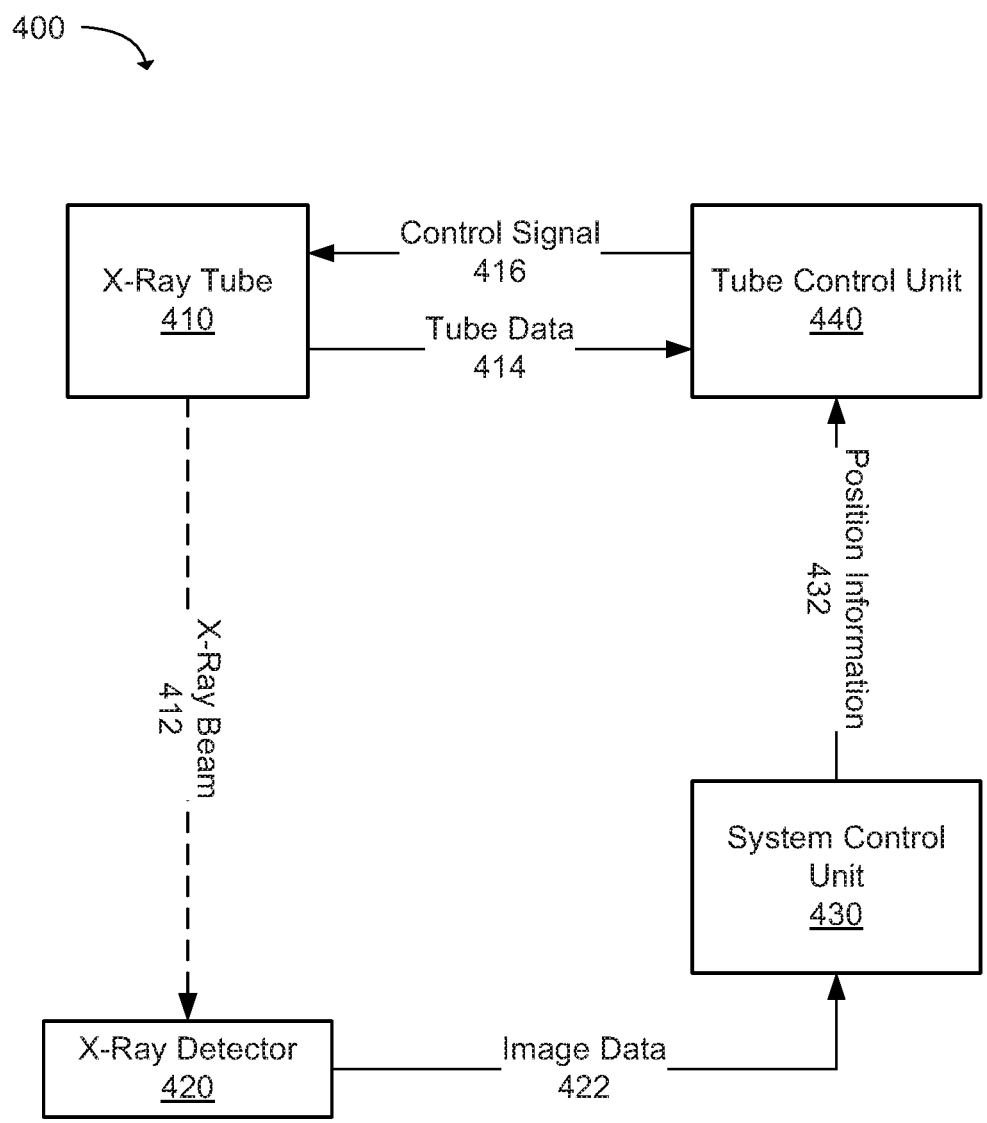
FIG. 8 illustrates a block diagram of an example x-ray system including an x-ray tube, a tube control unit (TCU), an x-ray detector, and a system control unit.

FIG. 8 illustrates an x-ray system 400 that can be used for electronic alignment, which includes an x-ray tube 410, a tube control unit (TCU) 440, an x-ray detector 420 or imager, and a system control unit 430. The TCU can be a separate component from the x-ray tube. In another example (not shown), the TCU is integrated with the x-ray tube. A high voltage tube generator (not shown) can provide a tube voltage (e.g., kilovolts [kV]), tube current (e.g., milliamps [mA]), and exposure duration (e.g., seconds [s]). As a result, the x-ray tube 410 emits an electron beam which collides with an anode target to generate an x-ray beam 412 with a central ray. The x-ray detector 420 detects the x-rays and generates image data 422 which contains the central ray position information, which is sent to the system control unit 430. The system control unit 430 generates position information 432, which can include an offset of the central ray relative to a specified imager location (e.g., the x-ray detector geometric center point), which can be sent to the TCU 440. The TCU 440 can provide control signals 416, such as signals to control steering magnetics and focusing magnetics in the x-ray tube. In some examples, the x-ray tube can provide tube data, such as feedback, to the TCU. In another example (not shown), the TCU can be coupled to the tube generator and also provide tube voltage, tube current, and exposure duration control.

Figure 22:
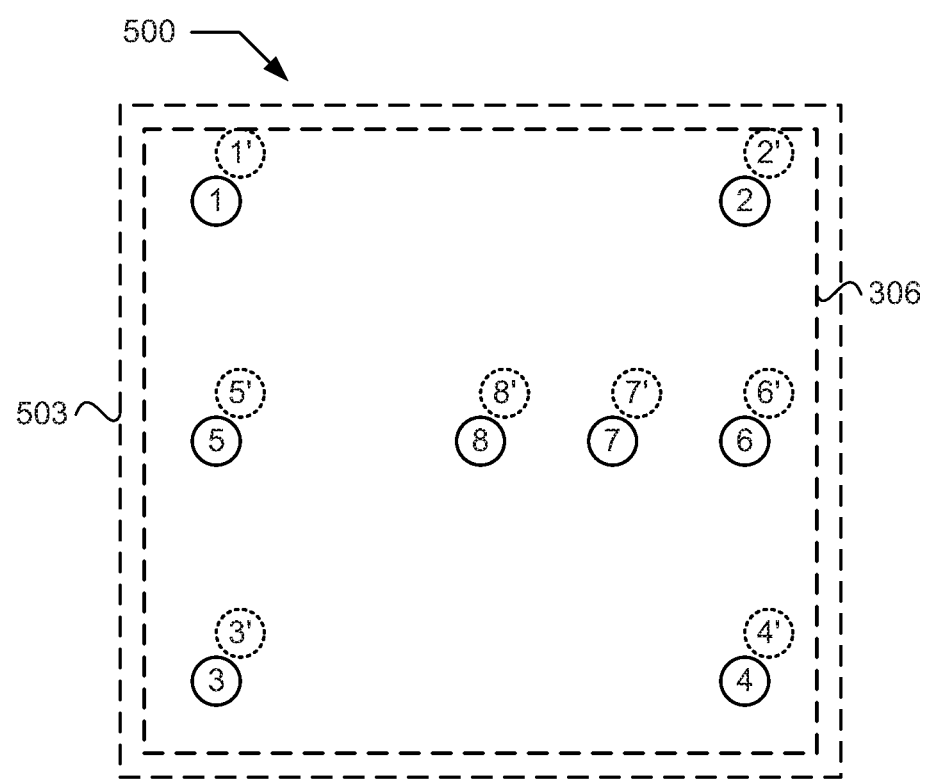
FIG. 22 illustrates an example focal spot deflection pattern showing central x-ray beam offset.

A magnetic steering mechanism of the x-ray tube and TCU electronics can be used to produce a constant offset superimposed on a focal spot deflection pattern, as described in greater detail with FIG. 22. The deflection pattern (or steering pattern) is a series of locations the focal spot is steered to in order to improve image resolution or an image signal to noise ratio. By applying an additional constant current offset to steering coils of the magnetic steering mechanism, the electron beam can be statically directed to a location within in a 2D plane of the x-ray detector, which allows an electronic alignment of the x-ray beam of the x-tube with the collimator or x-ray detector of the x-ray system.

In an example, a group of magnet pairs is oriented in the X and Y direction, substantially perpendicular to the electron beam in the x-ray tube. Current through the steering coils creates two magnetic fields which can be perpendicular to each other. The strength of the magnetic field can be controlled by the number of windings on the steering coils and the current driven through the steering coils. Deflection of the magnetic beam within a region of interest of the magnetic field can be considered linear and the amount of deflection is related to the magnetic field strength. Since magnetic fields along the x-axis and y-axis superimpose on each other, the electron beam can be directed to a location within the 2D x-y plane by applying respective current to the coils. The specific applied current creates the magnetic field needed to achieve a desired deflection. While a perpendicular arrangement of the steering coils can simplify current calculations to the steering coil, a non-perpendicular arrangement of the steering coils may also be used, as magnetic fields are vectors that can be superimposed. In one example, the steering coils can be oriented at various angles within the deflection plane or be broken up into multiple sequential coils along a third axis (e.g., z-axis) achieving deflection in multiple steps along the path of the electron beam. Additionally, more pairs of magnets can be added to form an array of steering magnets, so a vector sum of the magnetic fields produces the desired steering field for offsets and locations.

Focusing magnetics can also be used to focus or refocus the electron beam along the beam path from the emitter to the anode, as the electron beam tends to diverge with an increased distance between the emitter and the anode. By adding the deflection mechanism (or steering magnetics) to the x-ray tube, the distance between the emitter and the anode increases, resulting in an expanding focal spot size. The electron beam divergence can be observed as defocusing of the focal spot (e.g., reducing image resolution), hence an electronic focusing or refocusing mechanism can be used to counter act the expanding or diverging electron beam by focusing the beam in a small area on the anode.

Figure 9:
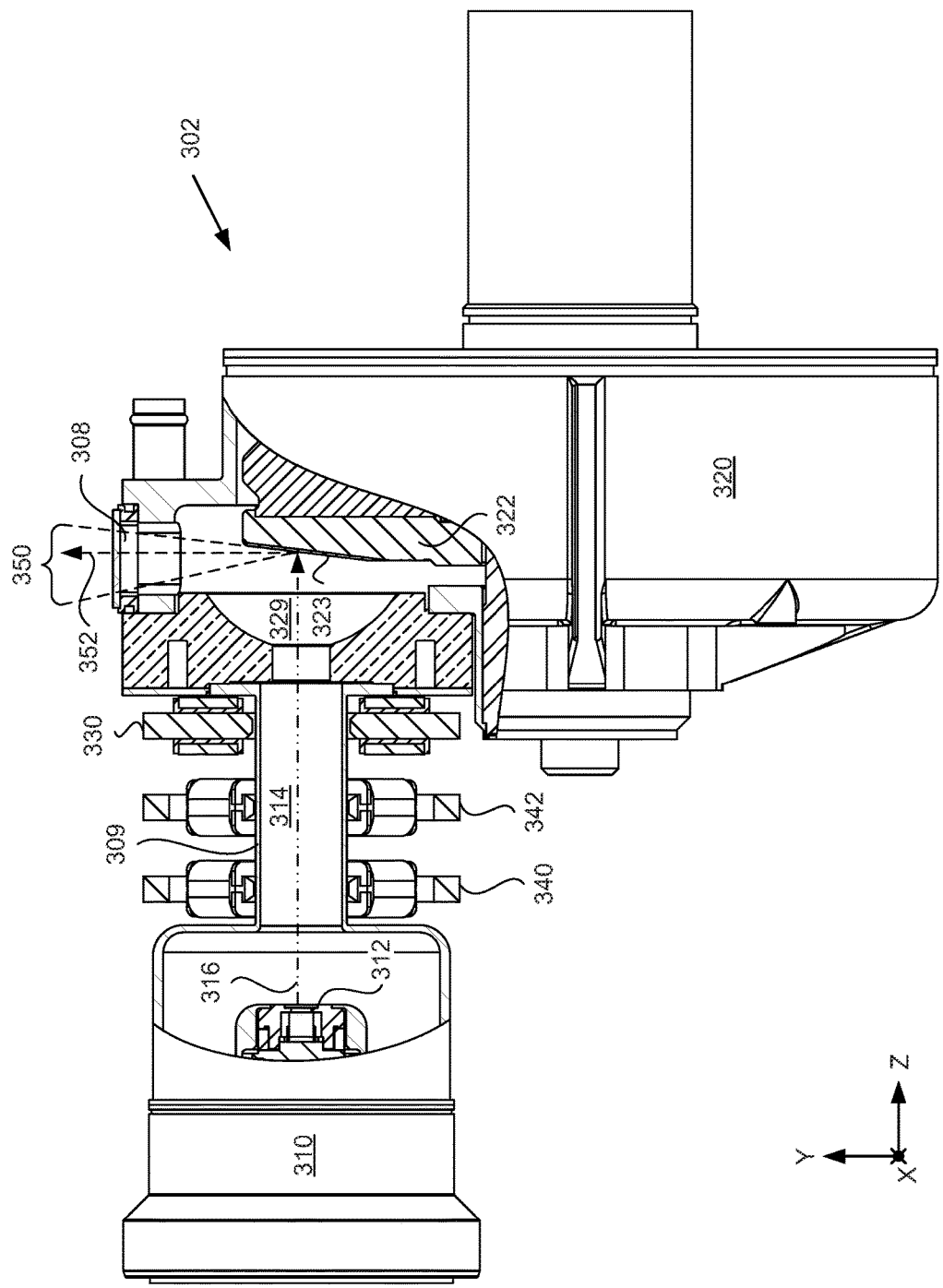
FIG. 9 illustrates a cross section side view of a partially exposed example x-ray tube assembly including focusing magnets and a steering magnet.

FIG. 9 illustrates an example x-ray tube assembly 302 that includes both steering magnetics 330 and focusing magnetics 340 and 342 that can be used for electronic alignment, more specifically electronic central ray alignment or electronic focal spot alignment. Electronic central ray alignment, which involves moving a focal spot 324 (FIG. 10C) on a focal track 323 of an anode 322, can also be referred to as electronic focal spot alignment. Electronic focal spot alignment uses the steering coils 330 and TCU electronics 440 (FIG. 8) of the x-ray tube magnetics to align the focal spot with the imaging system (i.e., x-ray imager or detector).

The x-ray tube assembly 302 includes cathode assembly 310, a drift region 314, and an anode assembly 320. The cathode assembly 310 includes an emitter assembly 312 that generates an electron beam with a centerline 316 that passes through the drift region. The drift region 314 is surrounded by focusing magnetics 340 and 342 and steering magnetics 330, which may be outside the vacuum envelop formed by the insert wall 309 (in the throat of the x-ray tube). An x-ray tube can be considered to have a long throw length when a drift region includes focusing magnetics and steering magnetics. The electron beam passes through an aperture 329 of a shield component, electron shield, or electron collector and strikes an anode target or anode 322 to generate x-radiation 350 with a central x-ray beam 352. The instantaneous area impacted by the electron beam on the anode is referred to as a focal spot and the area struck by the electron beam on rotary anode is referred to as the focal track 323. The x-rays may exit the x-ray tube through a window 308.

Figure 10A:
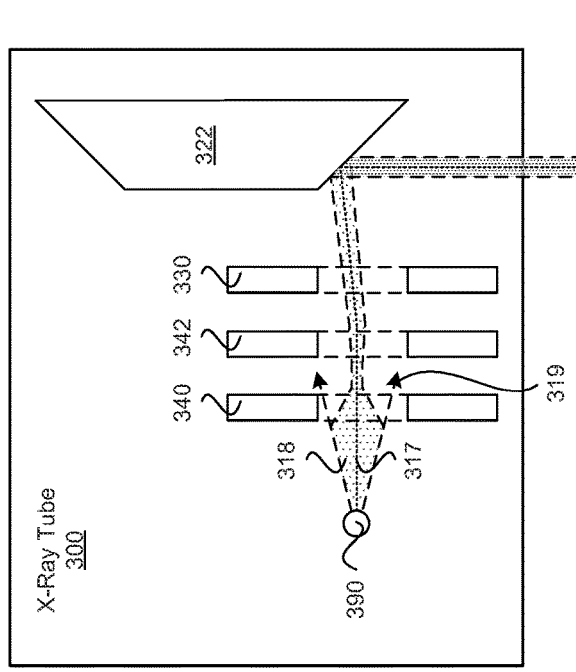
FIG. 10A illustrates a side view block diagram of an example electron beam focusing and steering mechanism in an x-ray tube.
Figure 10B:
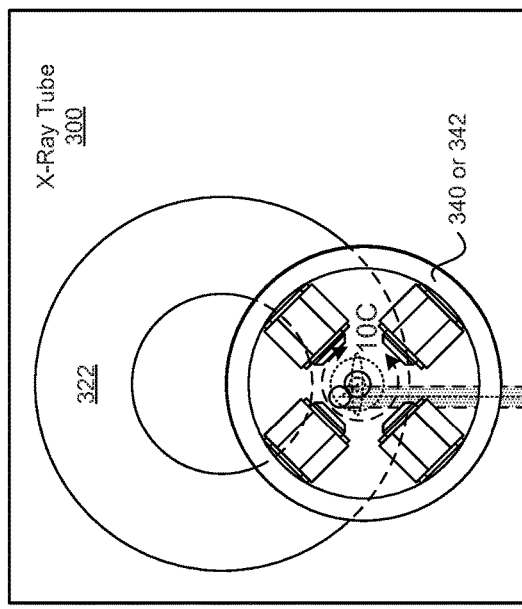
FIG. 10B illustrates a front view block diagram of example electron beam focusing and steering mechanism in an x-ray tube.
Figure 10C:
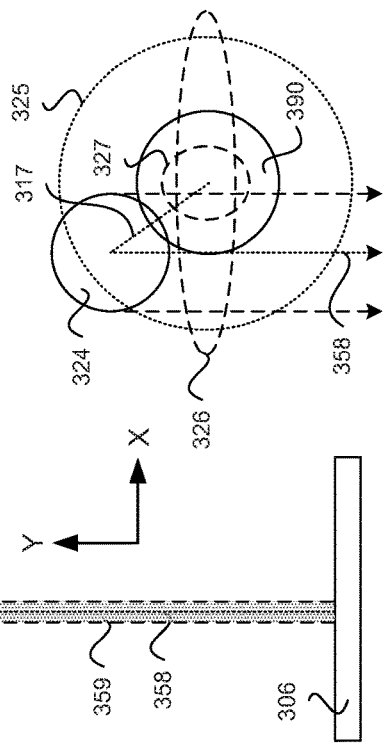
FIG. 10C illustrates an expanded front view block diagram of FIG. 17B showing the focusing and steering of the electron beam.

As shown, the focusing magnetics includes a first focusing magnetic quadrupole 340 (or cathode focusing magnetic quadrupole) and a second focusing magnetic quadrupole 342 (or anode focusing magnetic quadrupole), and the steering magnetics includes two steering magnetic dipoles on a core 330, as illustrated in FIGS. 10A-B. FIGS. 10A-C illustrate various views of electron beam focusing and steering in an x-ray tube 300. Electrons are emitted from the electron source 390 and accelerated towards the anode target 322. The electron beam includes negatively charged particles that have a repelling force between the electrons in the beam, which causes the electron beam to diverge or the cross sectional area (i.e., in the x-y plane) of the electron beam to expand (i.e., defocus) as the electrons travel from the electron source 390 (e.g., an emitter of the cathode assembly) to the anode 322. Thus, the electron density of the beam spreads the beam apart during transit, which may be significant. As a result the focal spot area can be larger than the cross sectional area of the electron beam at the electron source. This expansion or spreading of the electron beam can be referred to as electron beam bloom, electron bloom, or focal spot bloom, which can be greater with slower speeds of the electrons (i.e., lower tube voltages), greater electron densities (i.e., higher tube currents), or greater distances between the electron source and the anode target. Large focal spots distribute the x-ray energy over a larger physical area relative to small focal spots which can reduce the resolution of the x-ray images. The additional space used to add steering magnetics in the drift region can increase propensity for focal spot blooming (i.e., focal spot size growth due to beam space charge effects).

FIGS. 10A-C illustrate an electron beam 318 with electron bloom (i.e., defocusing), focusing, and steering. The electron beam has a centerline 317 that is steered up (as shown in FIGS. 10A-C) and to the left (as shown in FIGS. 10B-C). Electron bloom projections without focusing 319 are also illustrated, which can result in an enlarged focal spot or blurred focal spot (i.e., electron beam cross section with electron blooming or focal spot blooming 325). As shown, the centerline of the electron beam 317 may not change substantially with focusing or defocusing. On the way to the anode the electron beam is focused on a small area on the anode by the focusing mechanism. The focusing magnetics reduces focal spot blooming by compressing the electron beam in at least one direction. For example, the first focusing magnetic quadrupole 340 is configured for providing a first focusing magnetic quadrupole gradient for focusing the electron beam in a first direction (e.g., y-axis) and defocusing the electron beam in a second direction (e.g., x-axis) orthogonal to the first direction (i.e., electron beam cross section after first focusing 326, illustrated as a flat ellipse). The second focusing magnetic quadrupole 342 is configured for providing a second focusing magnetic quadrupole gradient for focusing the electron beam in the second direction (e.g., x-axis) and defocusing the electron beam in the first direction (e.g., y-axis) (i.e., electron beam cross section after second focusing 327). The combination of the first and second focusing magnetic quadrupoles provides a net focusing effect in both first and second directions of a focal spot 324 of the electron beam 318. The net focusing effect produces a high intensity x-ray beam 359 with a central x-ray beam 358 that impinges on the x-ray imager 306. The x-ray beam is shown as a narrow beam to illustrate a high intensity for a narrow focal spot. An actual x-ray beam may have a cone shape with lower intensity x-ray further away from the central x-ray beam 358.

The steering magnetics includes two steering magnetic dipoles on a core 330. The two steering magnetic dipoles 330 are configured to deflect the electron beam in order to shift a focal spot of the electron beam on a target surface or focal track of the anode (in the x-y plane), which in turn moves the generated x-ray beam 359 with a central x-ray beam 358 (in the x-z plane). One steering magnetic dipole moves the focal spot in the x-axis (resulting in the central ray moving along the x-axis) and the other steering magnetic dipole moves the focal spot in the y-axis (resulting in the central ray moving along the z-axis).

U.S. patent application Ser. No. 14/660,584 (or U.S. Patent Application Publication No. 2015/0187536) entitled, "X-Ray Tube Having Planar Emitter and Magnetic Focusing and Steering Components," which is incorporated by reference in its entirety, discloses examples of magnetic focusing components and magnetic steering components.

Figure 11:
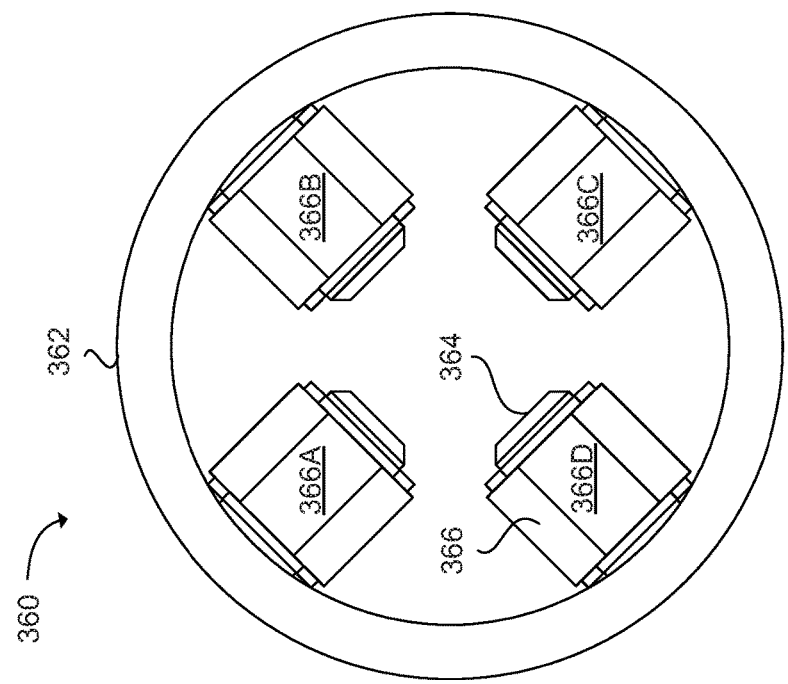
FIG. 11 illustrates a side view of an example magnetic yoke with four pole projections.

FIG. 11 illustrates a magnet system 360 with a magnetic yoke 362 having four pole projections 364, where each pole projection includes corresponding coils 366. The coils 366 can be formed of wire, windings, or turns around the pole projections core that include an electrical conductive material (e.g., copper or aluminum) with an electrically insulated sheath, such as enameled magnet wire (i.e., transformer wire). A current through the coils produces a magnetic field emitted from the pole projections.

The core (or yoke) 362 shown has a substantially circular or annular shape, it will be appreciated that each of the core (or yoke) portions can also be configured with different shapes, such as a rectangular, ellipsoid (i.e., oval), or semi-circular shape, as long as the core at least partially surrounds the electron beam (e.g., in the drift region). The pole projections 364 can include projections that extend from the interior of the core and oppose or face each other in pairs (e.g., pole projections of coils 366A and 366C oppose or face each other and pole projections of coils 366B and 366D oppose or face each other).

The yoke 362 and pole projections 364 can include ferromagnetic or ferrimagnetic materials. Ferromagnetic and ferrimagnetic materials are materials that can exhibit spontaneous magnetization. More specifically, a material is "ferromagnetic" if all of its magnetic ions add a positive contribution to the net magnetization. If some of the magnetic ions subtract from the net magnetization (if magnetic ions are partially anti-aligned), then the material is "ferrimagnetic". A ferrimagnetic material is one that has populations of atoms with opposing magnetic moments, as in antiferromagnetism. However, in ferrimagnetic materials, the opposing moments are unequal and a spontaneous magnetization remains. Ferromagnetism occurs in a few substances, such as iron (Fe), nickel (Ni), cobalt (Co), their alloys, and some alloys of rare earth metals. For example, ferromagnetic compounds or materials include manganese bismuth (MnBi), manganese antimony (MnSb), chromium dioxide or chromium(IV) oxide ($CrO_2$), manganese arsenic (MnAs), gadolinium (Gd), dysprosium (Dy), and europium oxide (EuO). Ferrimagnetic compounds or materials include iron (III) oxide ($Fe_2O_3$) or ferric oxide, iron (II,III) oxide ($FeOFe_2O_3$ or $Fe_3O_4$), nickel oxide-iron (III) oxide ($NiOFe_2O_3$), copper oxide-iron (III) oxide ($CuOFe_2O_3$), magnesium oxide-iron (III) oxide ($MgOFe_2O_3$), manganese oxide-iron (III) oxide ($MnOFe_2O_3$), and yttrium iron garnet ($Y_3Fe_5O_{12}$). As used herein and for simplicity in the description, a "ferromagnetic" material refers to a material that can exhibit spontaneous magnetization (i.e., either a ferromagnetic material or a ferrimagnetic material).

For example, the yoke 362 and pole projections 364 includes can include various materials, such as solid metal core (e.g., a silicon steel core), a powdered metal core (e.g., carbonyl iron core), and ferrite or ceramic cores. The solid metal cores can include "soft" (annealed) iron, "hard" iron, laminated silicon steel, special alloys (specialized alloys for magnetic core applications, such as mu-metal, permalloy, and supermalloy), and vitreous metals (e.g., amorphous metal alloys [e.g. Metglas] that are non-crystalline or glassy).

The four poles 364 of the magnet system 360 shown in FIG. 11 can be configured as a quadrupole (e.g., used for focusing) or configured as a pair of dipoles (e.g., used for steering). In a quadrupole configuration, the coils of the four poles are electrically coupled together in series, which can be coupled to a power supply. In a dipole configuration, the coils of two opposing poles are electrically coupled together in series, which can be coupled to a power supply. If two dipoles are located on the same yoke, each dipole can be coupled to separate power supplies.

Figure 12:
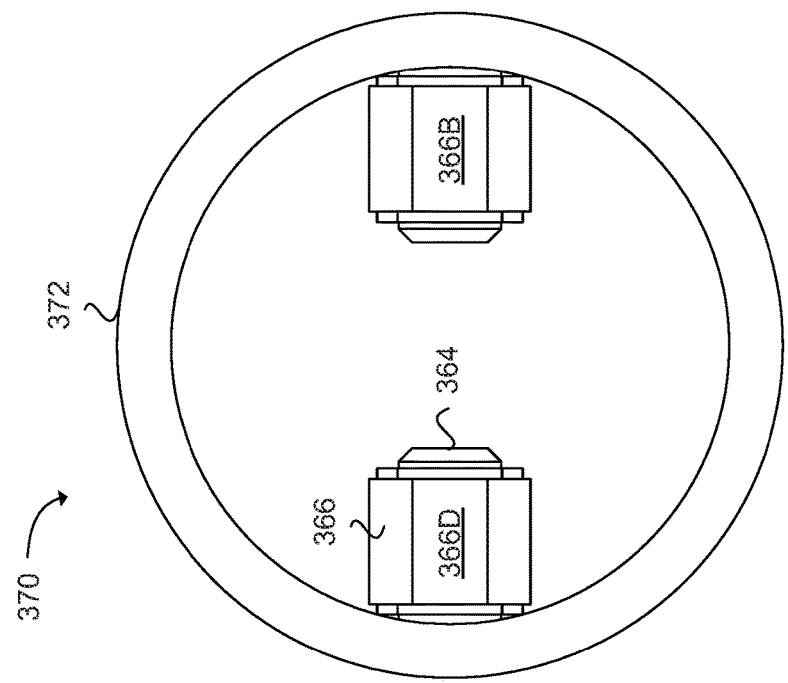
FIG. 12 illustrates a side view of an example magnetic yoke with two pole projections.

FIG. 12 illustrates a magnet system 370 with a magnetic yoke 372 having two pole projections 364, where each pole projection includes corresponding coils 366. The two poles of the magnet system 370 shown in FIG. 12 can be configured as a dipole (e.g., used for steering).

Figure 13B:
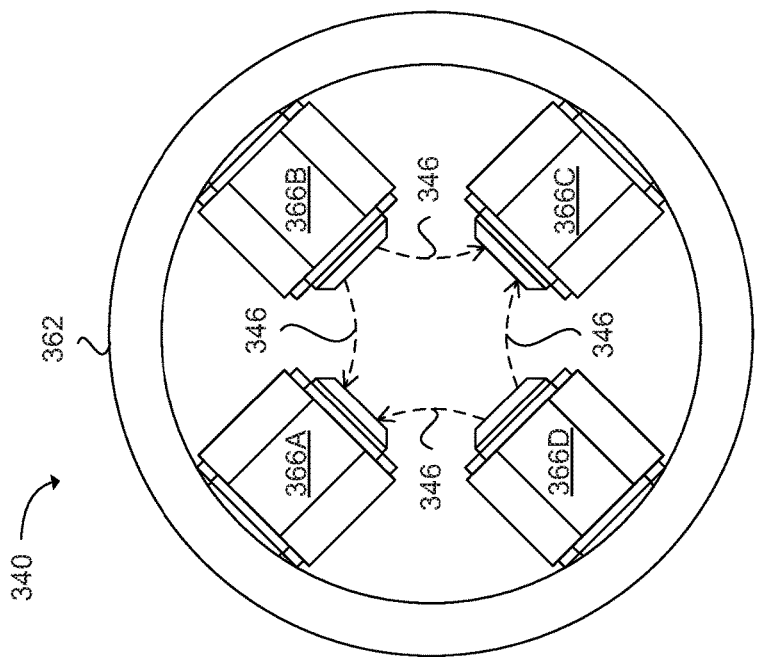
FIGS. 13A-B illustrate a side view of example quadrupole electromagnets used for focusing.
Figure 13A:
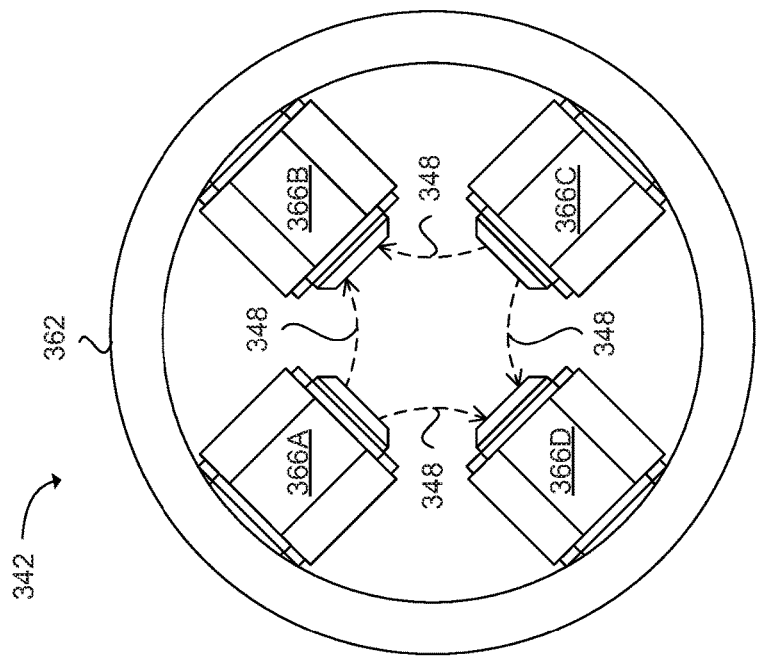

FIG. 13A shows a first focusing magnet 340 having a yoke 362 configured as a quadrupole (e.g., cathode-side focusing magnetic quadrupole 340), and FIG. 13B shows a second focusing magnet 342 having a yoke 362, also configured as a quadrupole (e.g., anode-side focusing magnetic quadrupole 342). Each quadrupole creates a magnetic field having a gradient, where the magnetic field intensity differs within the magnetic field. The gradient is such that the magnetic quadrupole field focuses the electron beam in a first direction (e.g., y-axis) and defocuses in a second direction (e.g., x-axis) that is perpendicular to the first direction. The two quadrupoles can be arranged such that their respective magnetic field gradients are rotated about 90° degrees with respect to each other. A first magnetic field 346 generated by the first focusing magnetic quadrupole 340 is shown in FIG. 13A, and a second magnetic field 348 generated by the second focusing magnetic quadrupole 342 is shown in FIG. 13B. The first focusing magnetic quadrupole 340 focuses in a length direction (e.g., y-axis), and defocuses in width direction (e.g., x-axis) of the electron beam. The electron beam is then focused in a width direction (e.g., x-axis) and defocused in length direction (e.g., y-axis) by the following the second focusing magnetic quadrupole 342. In combination the two sequentially arranged magnetic quadrupoles insure a net focusing effect in both directions of the focal spot.

Figure 14:
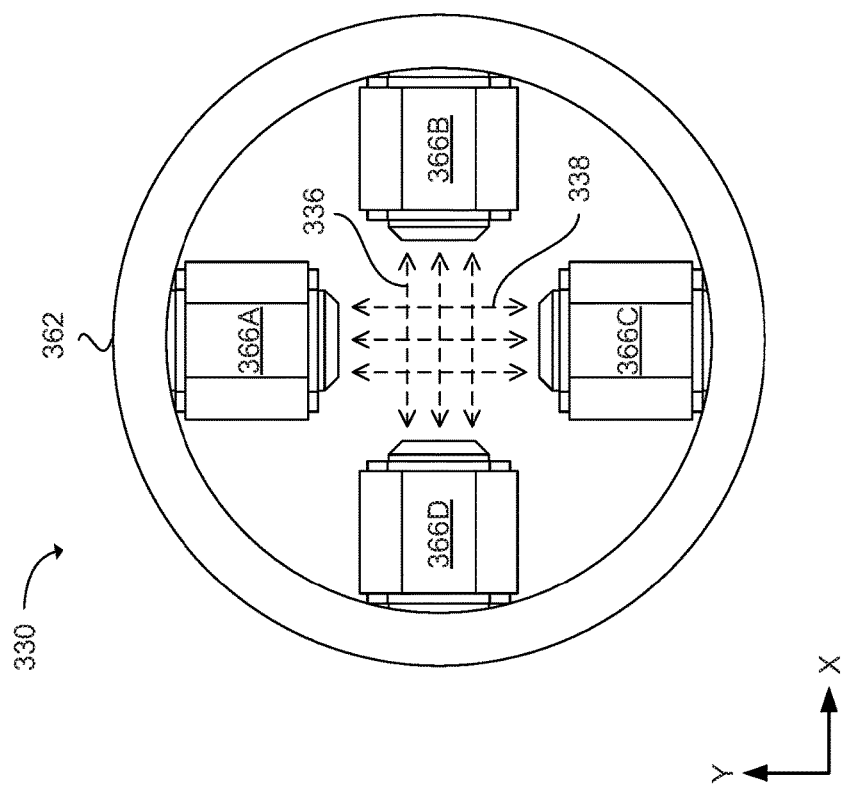
FIG. 14 illustrates a side view of an example of two dipole electromagnets used for steering.

FIG. 14 illustrates a steering magnet 330 having a yoke 362 configured with two sets of dipole coils. The first set of dipole coils (y-axis dipole coils) 366A and 366C generate a uniform or laminar magnetic field 338 in one direction (e.g., y-axis), and the second set of dipole coils (x-axis dipole coils) 366B and 366D generate a uniform or laminar magnetic field 336 in another direction (e.g., x-axis). The steering magnet allows for 2D steering of the electron beam (e.g., in the x-y plane) and resulting in a change in position of the focal spot (e.g., in the x-y plane) and the central ray (e.g., in the x-z plane). The uniform or laminar magnetic fields between the poles projections provides a homogeneous magnetic field in the area where the electron beam crosses the steering magnetic field (e.g., in the x-y plane), so electrons in the electron beam experience a similar amount of deflection, which can maintain a focal spot shape without substantial geometric distortion. Using orthogonal magnetic fields (i.e., a set dipole pole projections that are perpendicular to another set of dipole pole projections) can simplify magnetic vector calculation, but non-orthogonal magnetic fields may also be used.

Figure 15A:
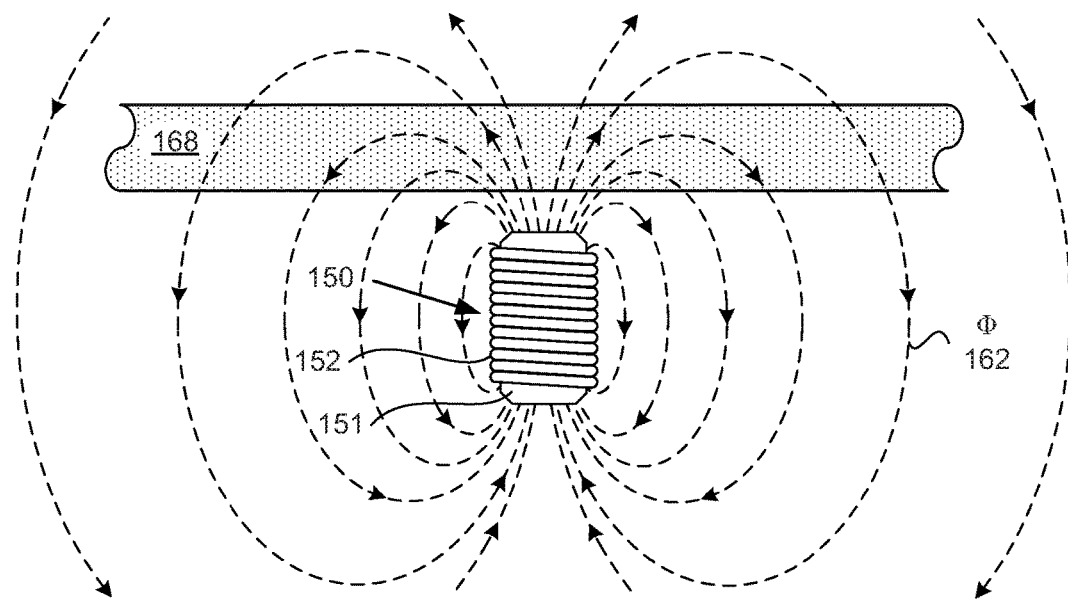
FIG. 15A illustrates a side view of an example electromagnetic solenoid.
Figure 15B:
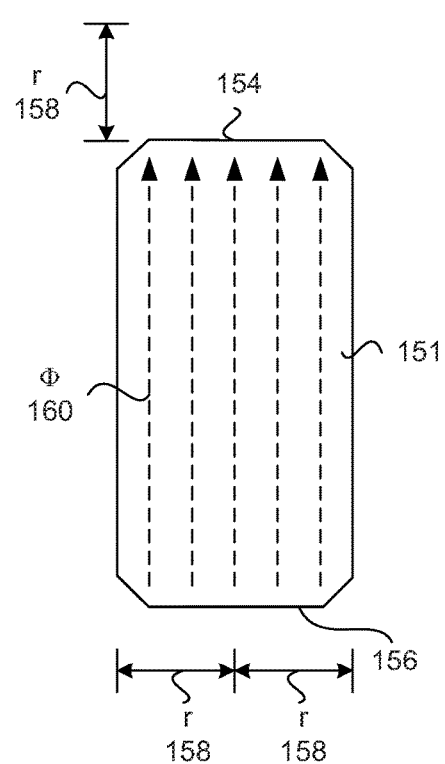
FIG. 15B illustrates an expanded side view of the electromagnetic solenoid core shown in FIG. 15A.

FIGS. 15A-B illustrate a solenoid electromagnet 150 (e.g., with cylindrical core 151) with windings or a coil 152 (e.g., single coil). Although a magnetic core 151 is shown for ease of illustration, the solenoid electromagnet may not require the magnetic core and similar magnetic fields still exit within the coil 152 of the solenoid electromagnet 150 (with an open center volume). The same principles regarding the solenoid electromagnet apply with or without a magnetic core. The magnetic flux 160 within the solenoid magnet core 151 (or within the coil 52) are substantially uniform from the south pole 156 to the north pole 154, but the magnetic flux 162 external to (e.g., surrounding) the solenoid magnet 150 are dissimilar and varied from the north pole 154 to the south pole 156. If a solenoid electromagnet is used for electron beam steering, the magnetic field 162 experienced by the electron beam 168 is very inhomogeneous. The amount of inhomogeneity increases with the distance between the electron beam and the solenoid, so the electrons at the bottom of the electron beam (closer to the solenoid) experience a different amount of deflection than electrons at the top of the beam (further from the solenoid). This difference in deflection causes the focal spot to change shape and size, and in an extreme case can cause the top and bottom of the electron beam to cross each other. Not only is the magnetic field inhomogeneous, the magnetic field at different points in the electron beam also has different vector directions (e.g., not all vertical or horizontal), so the direction of the force on the electrons in the electron beam change not only based on position in the electron beam (in the x-y plane) but the direction of the force on the electrons also changes during the crossing of the magnetic field (in the z-axis). In addition, the magnetic field (from the solenoid) has less force with a greater distance from the poles (e.g., electron beam separated from the pole ends of the solenoid, which may also include an insert wall between the solenoid and the electron beam). For example, a magnetic force at a distance of a radius r 158 away from the pole end of the solenoid (e.g., north pole 154) can be a factor of ten times less than the magnetic force at the pole end of the solenoid. Given the inconsistent deflection throughout the electron beam in both magnitude and direction due to the varying magnetic fields and vectors generated by the solenoid electromagnet, the solenoid type electromagnetic is problematic for fine control of the deflection of the electron beam used in steering. Focal spots created using the solenoid electromagnet for steering can suffer from severe distortion in shape and size. Changes in the shape or size (i.e., enlarged size) of the focal spot can negatively impact image quality and resolution, so an x-ray system generating such focal spots can be limited in detecting fine structures. Furthermore, without focusing, the challenges of inhomogeneous magnetic field from the solenoid electromagnet in conjunction with the repelling force between electrons causing blooming of the focal spot can generate a focal spot that is so large that the resulting image does not have a usable resolution.

Referring back to FIG. 14, the magnetic core that surrounds the electron beam with pole projections on opposite sides of the electron beam can generate a homogeneous magnetic field so the electrons in the electron beam experience a similar magnetic field and deflection enabling a fine control of the position of the focal spot. Fine control of the size of the focal spot can be provided by the focusing magnetics, previously described. As previously discussed, the magnetic field between the dipoles can be linear and perpendicular to travel direction of the electron beam so the electrons experience a similar amount of deflection in a substantially same direction.

Although, a four pole magnet system is shown for the focusing magnetics 340 and 342 and steering magnetics 330 in FIGS. 9-10C, 13A-14, and 16-17, other configurations of a magnetic multipole may be used with at least two poles. In a four pole magnet system, the coils can be configured as a quadrupole or a pair of dipoles. In a two pole magnet system, the coils can be configured as a dipole. It can be appreciated the magnet system used for focusing or steering can have multiple poles (e.g., two, four, six, or eight) and can have various configurations (e.g., dipole, quadrupole, hexapole, or octupole).

Figure 16B:
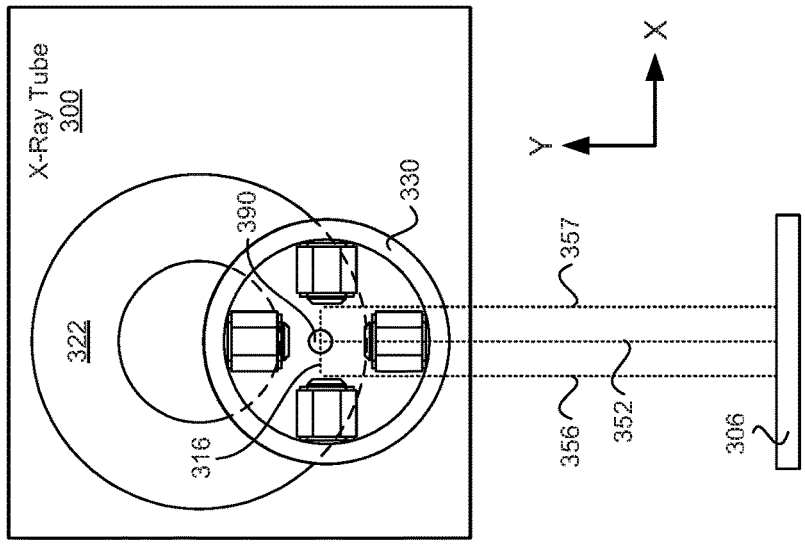
FIG. 16B illustrates a front view block diagram of example electron beam steering mechanism in an x-ray tube and corresponding central x-ray beam.
Figure 16A:
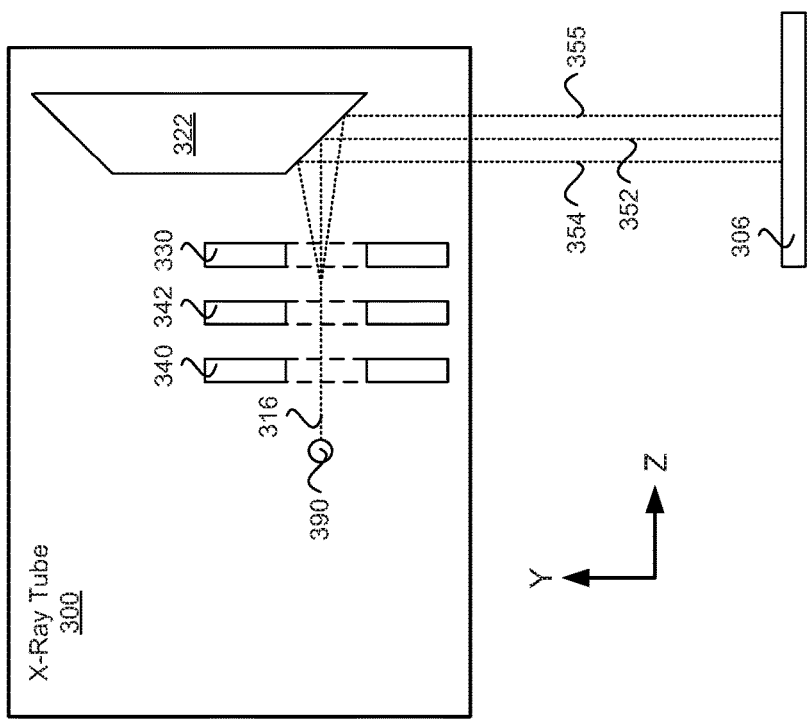
FIG. 16A illustrates a side view block diagram of example electron beam steering mechanism in an x-ray tube and corresponding central x-ray beam.

FIGS. 16A-B illustrate an electron beam steering mechanism 330 integrated in an x-ray tube 300 controlled by the TCU that can provide fine electronic central ray alignment or fine electronic focal spot alignment for the x-ray tube. As electrons impact the anode 322, x-rays are emitted. The location of the electron impact is projected onto the x-ray detector 306, thus a change in the location of the impact changes the location of the central x-ray beam on the x-ray detector 306. Hence by static deflection of the electron beam, the central x-ray beam location on the detector can be changed. The steering mechanism 330 is used to align the central x-ray beam location with an image axis. Misalignment of the x-ray axis (or central x-ray beam) with the imaging axis results in blurring and geometric distortion of the image and can thereby degrade image quality and diagnostic value of the image.

For example, based on the signals (e.g., current) applied to the coils of the steering magnet 330 the electron beam centerline 316 can be adjusted to different positions due to changes in focal spots on the anode 322, resulting in different central ray 352, 354, 355, 356, and 357 positions. Central ray 354, 355, 356, or 357 positions result from a deflected electron beam. By moving the location of the electron impact on the target of the anode 322, the location of the central ray on the x-ray detector 306 is changed. An upward (e.g., y-axis) steered electron beam results in an downward (e.g., z-axis) steered central x-ray beam 354, and an downward (e.g., y-axis) steered electron beam results in an upward (e.g., z-axis) steered central x-ray beam 355. A left (e.g., x-axis) steered electron beam results in a left (e.g., x-axis) steered central x-ray beam 356, and a right (e.g., x-axis) steered electron beam results in a right (e.g., x-axis) steered central x-ray beam 357. Without an applied signal to the coils of the steering magnet 330 the central x-ray beam 352 is referred to as a non-steered central x-ray beam or a central x-ray beam without an offset.

Figure 17:
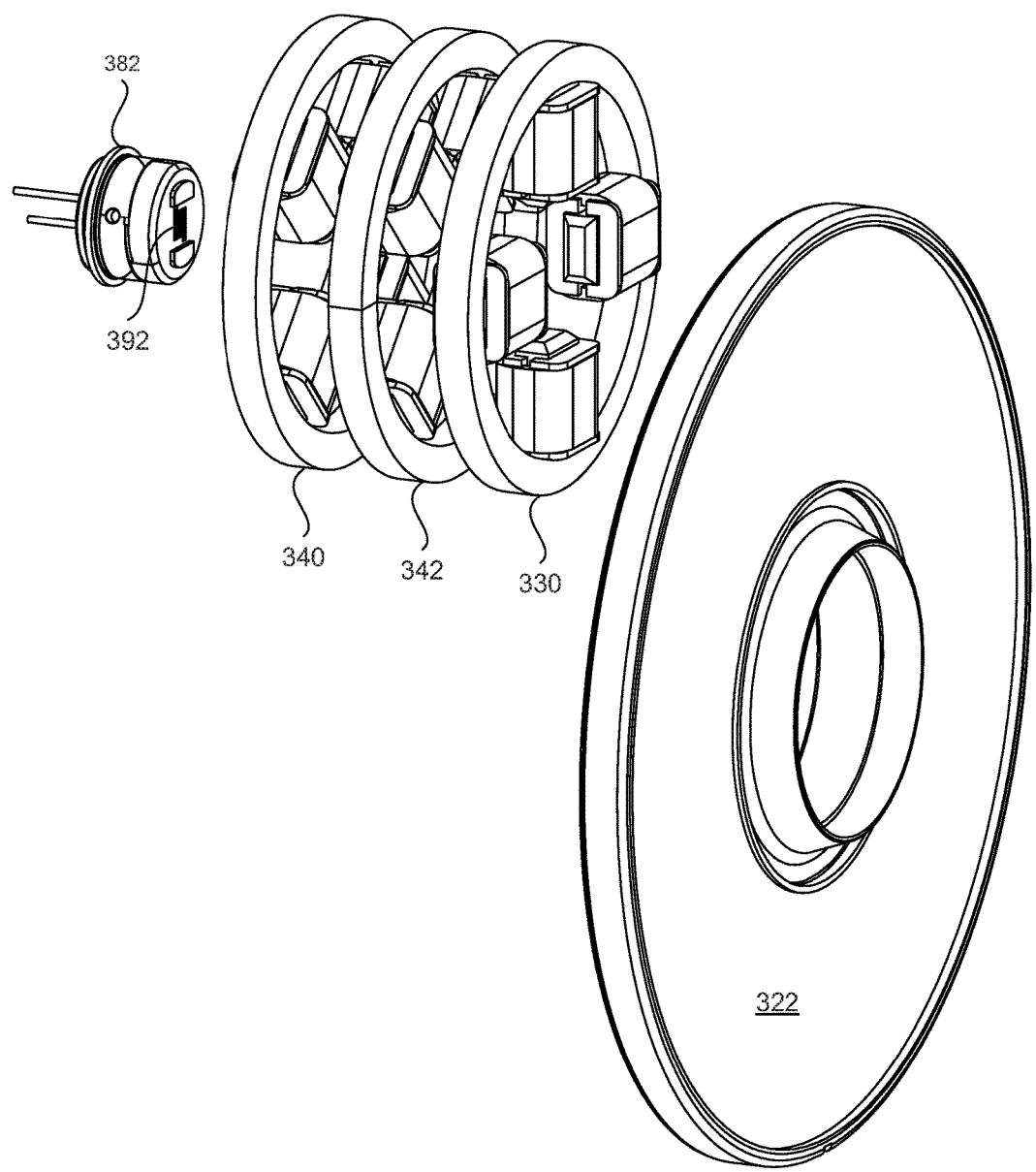
FIG. 17 illustrates a perspective view of an emitter, focusing magnets, a steering magnet, and an anode.

FIG. 17 illustrates a perspective view of x-ray tube components showing the emitter assembly 382, focusing magnets 340 and 342, a steering magnet 330, and anode 322, which configuration is similar to the x-ray tube assembly shown in FIG. 9. The components in FIG. 17 can provide electronic central ray alignment or fine electronic focal spot alignment for the x-ray tube. The emitter assembly 382 is shown with a planar emitter 392. U.S. patent application Ser. No. 14/660,607 (or U.S. Patent Application Publication No. 2015/0187530) entitled, "X-Ray Tube Having Planar Emitter with Tunable Emission Characteristics," which is incorporated by reference in its entirety, discloses an example planar emitter.

Figure 18A:
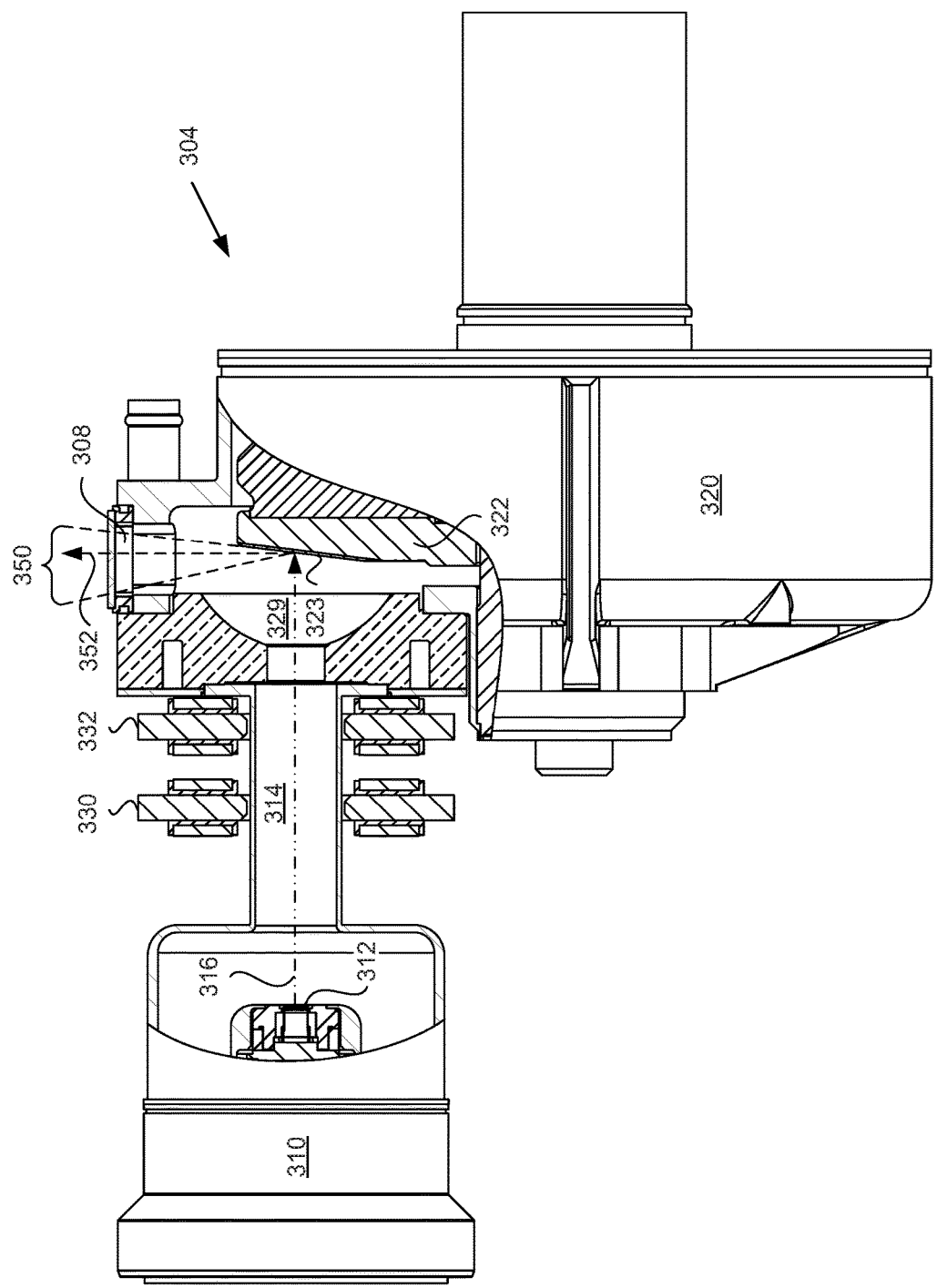
FIG. 18A illustrates a cross section side view of a partially exposed example x-ray tube assembly including steering magnets.
Figure 18B:
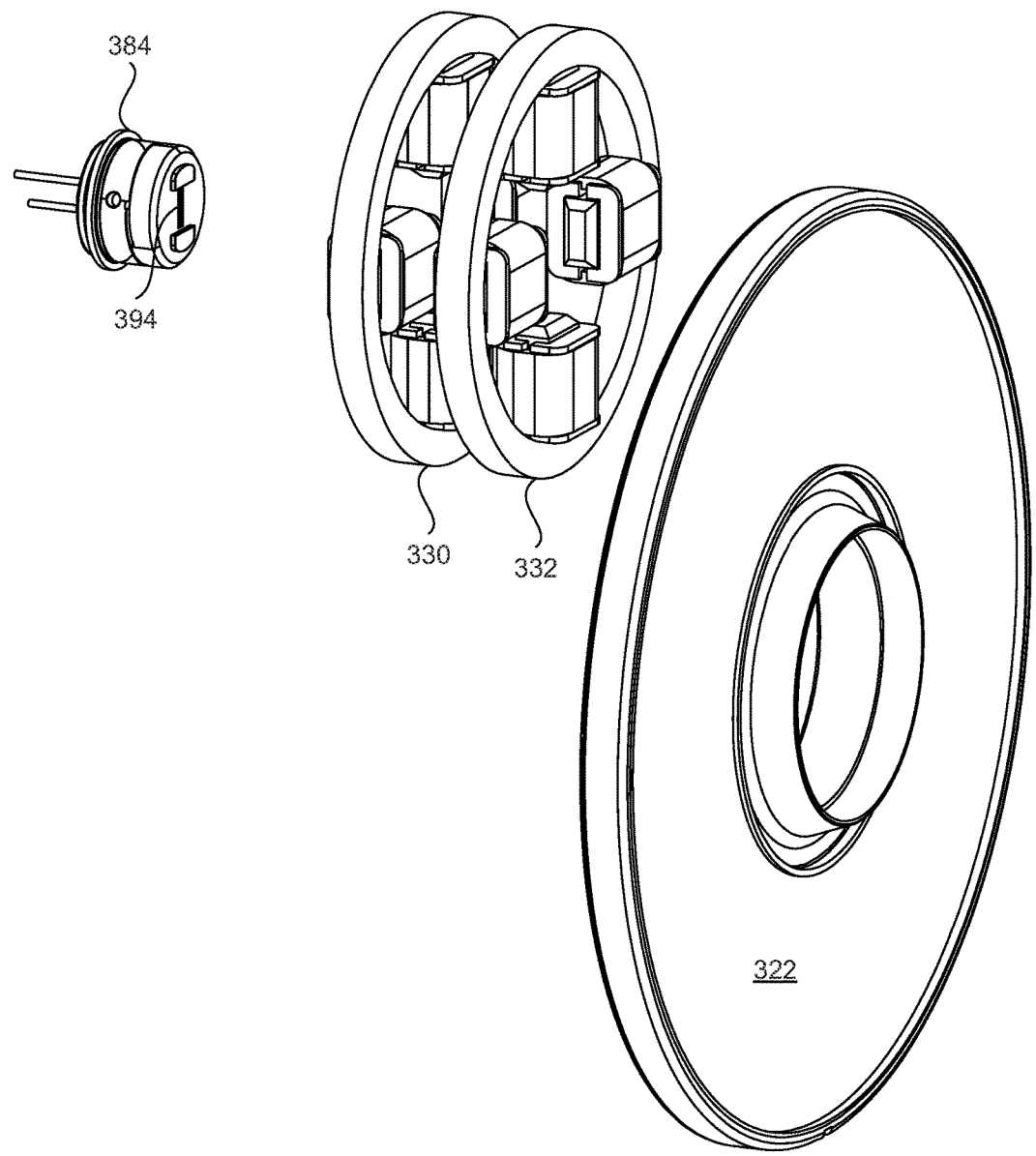
FIG. 18B illustrates a perspective view of an example emitter, steering magnets, and anode.

FIGS. 18A-B illustrates an x-ray tube assembly that includes two steering magnet cores 330 and 332. In an example, a first steering magnet 330 can provide a first steering magnetic field and a second steering magnet 332 can provide a second steering magnetic force (e.g., ultra-fine adjustment or steering). FIG. 18B illustrates an emitter assembly 384 with a coil emitter 394. A planar emitter or coil emitter can be used with the various focusing and steering magnetics shown or described.

Figure 19:
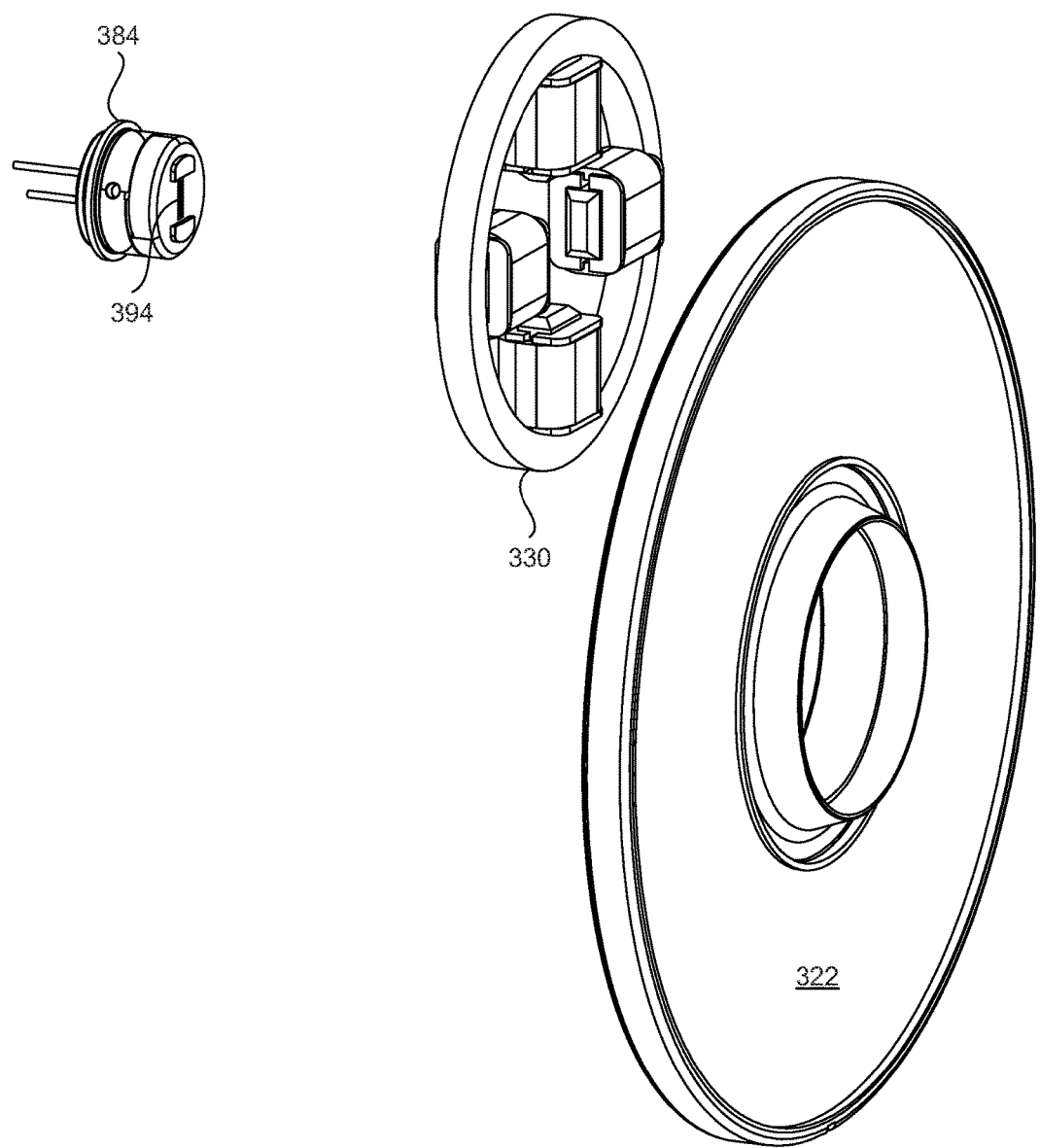
FIG. 19 illustrates a perspective view of an example emitter, two dipole steering coils on a yoke, and anode.

FIG. 19 illustrates a perspective view of x-ray tube components showing the emitter assembly 384, a steering core with two dipole steering coils 330, and anode 322. The steering core 330 can provide 2D steering.

Figure 20:
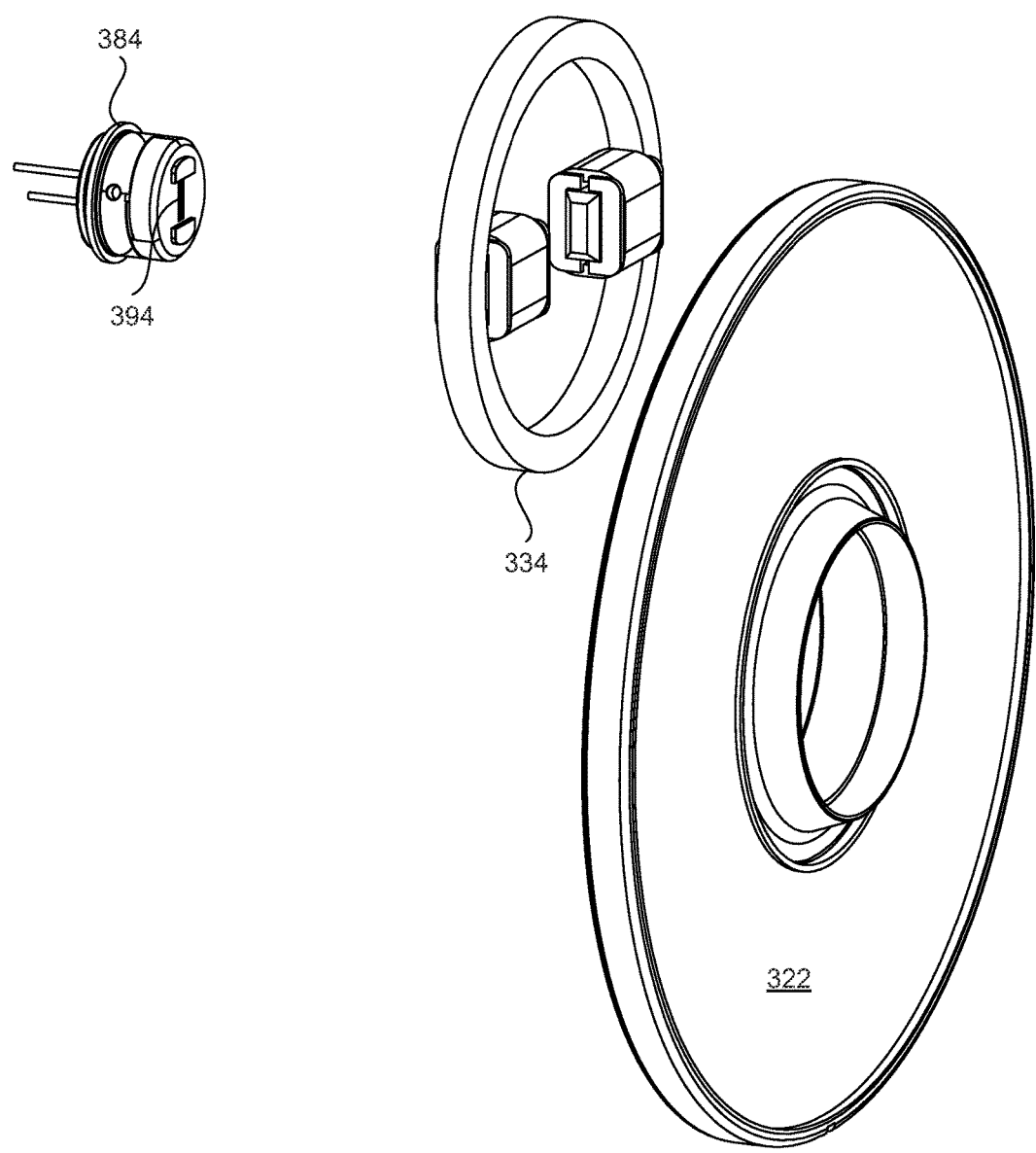
FIG. 20 illustrates a perspective view of an example emitter, a dipole steering coil on a yoke, and anode.

FIG. 20 illustrates a perspective view of x-ray tube components showing the emitter assembly 384, a steering core with dipole steering coils 334, and anode 322. The steering core 334 can provide one dimensional (1D) steering (e.g., along the y-axis).

Figure 21:
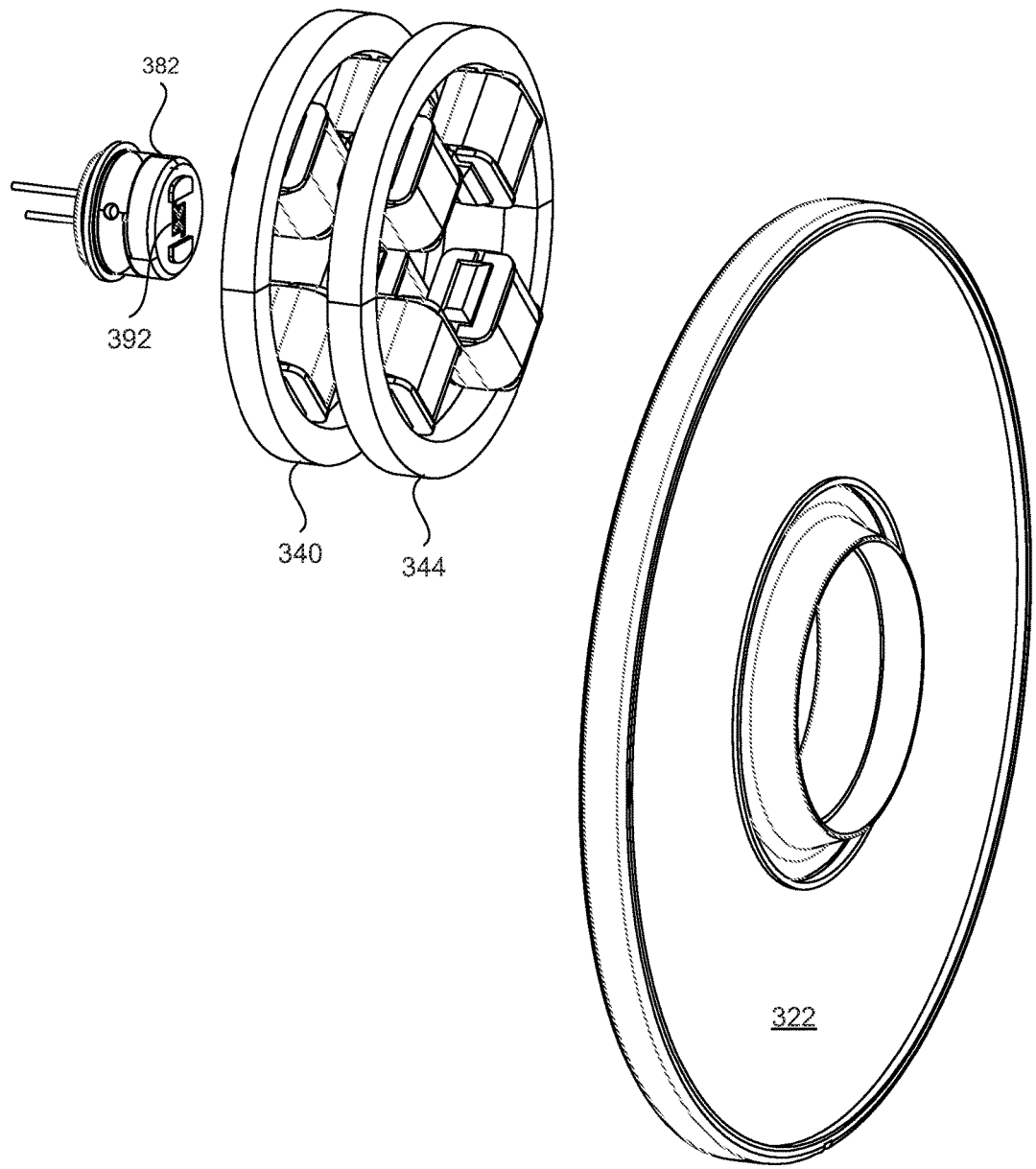
FIG. 21 illustrates a perspective view of an example emitter, steering coils and focusing coils co-wound on a yoke, and anode.

FIG. 21 illustrates a perspective view of x-ray tube components showing the emitter assembly 382, anode 322, a focusing magnet 340, and a second focusing magnet 344 that includes core with pole projections, where each pole projection includes focusing coils and steering coils. The second core assembly 344 is configured to provide both focusing and steering. The magnet field vectors from focusing and steering can be super imposed on each other. In an example, the focusing coils and steering coils can use different power supplies or driver circuits.

The steering magnetics can be used to change the location of the central ray relative to the x-ray imager 306. The central ray may change or toggle during a scan (e.g., CT scan) or an x-ray exposure based on the location and orientation of an object relative to the x-ray imager 306 at a specified time. An x-ray system may use a central ray beam deflection pattern 500 (or a focal spot deflection pattern), as illustrated in FIG. 22. The number of deflection points and position of deflection points depend on a particular deflection pattern (or steering pattern). An order in which the different deflection points are steered can depend on the imaging requirements. A deflection pattern can be used for a particular x-ray system or type of image being acquired (e.g., specific patient anatomy). Each deflection position can be oriented relative to a specified imager location (e.g., the x-ray imager geometric center point 8) within a steering range 503. The steering range 503 may be greater than, equal to, less than, or a different shape from the exposure area of the x-ray imager 306. The deflection pattern 500 shown in FIG. 22 includes eight deflection points 1-8 with a non-deflected center point 8. In an image acquisition, the x-ray system may only toggle between a few points or toggle through any combination of the deflection points (e.g., eight points). The sequences and location can depend on an imaging goal. For example, if a goal is to increase resolution in the horizontal direction, the x-ray system may toggle between points 8 and 7, 8 and 6, or 5 and 8. An order and location for the steering pattern can be determined by a system manufacturer or an imaging physicist.

Figure 23:
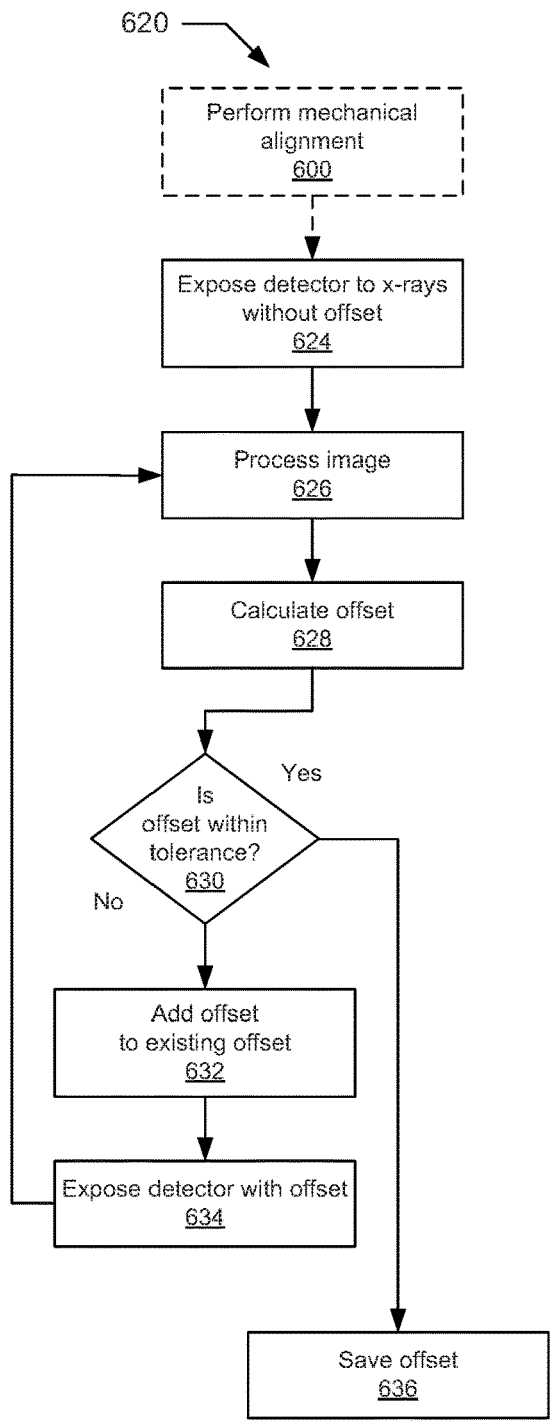
FIG. 23 illustrates a flowchart for an example electronic alignment of a focal spot (and a central x-ray beam).

In electronic central ray alignment (or electronic focal spot alignment), a constant offset value can be added to a central ray position or a steered ray beam position. FIG. 23 illustrates an example flowchart of the electronic central ray alignment 620 of the x-ray tube, which aligns the central x-ray beam with the specified imager location. First, a relatively coarse mechanical alignment can be performed 600. In one example, the coarse mechanical alignment is less than (<) 0.5 mm. In another example, the coarse mechanical alignment is <0.1 mm. The time to perform the course mechanical alignment can be less than 30 minutes (e.g., 15 minutes). The remaining offset (to an acceptable tolerance) can be adjusted by the steering magnetics (e.g., steering the electron beam) in the x-ray tube. The electronic central ray alignment allows a far finer and accurate adjustment than mechanical alignment, which also can be adjusted in shorter timeframe. The electronic fine adjustment process can be performed by changing a digital offset value compared to fine mechanical adjustments accomplished with measurements and tools.

Referring back to the flowchart 620, the imager or detector is exposed to x-rays from the x-ray tube 624, usually with an alignment object or phantom. The image of the x-ray detector is processed 626 by a processor in the x-ray detector or a system control unit, and the processor calculates an offset (or offset value) representing a distance of the central ray on the imager from the specified imager location (e.g., the x-ray detector geometric center point) 628. In one example, the offset represents a 2D distance of the focal spot in the x-y plane (i.e., with an x-axis component and a y-axis component) or the central ray in the x-z plane (i.e., with an x-axis component and a z-axis component). In another example, the offset represents a 1D distance of the focal spot along the x-axis or the y-axis or the central ray along the x-axis or the z-axis. The processor determines if the offset is within an acceptable tolerance or precision 630 (e.g., the central ray with the offset is within an acceptable tolerance or precision). In an example, the offset value can have an acceptable tolerance or precision that is <25 μm (from perfect alignment). In another example, the offset value can have an acceptable tolerance or precision that is <200 μm (from perfect alignment). The precision of the alignment can depend on the focal spot size, an imager pixel size, temporal resolution desired, and the image quality requirements for an x-ray system. For example, in CT imaging, shifting the central x-ray beam by ¼ detector pixel size can avoid aliasing and increase the temporal resolution. Pixel aliasing can occur when a pixel detects light or x-rays intended for a neighboring pixel, which can cause image artifacts. In such a case, the fine electronic alignment can set the precision to ¼ pixel and can align down to ¼ pixel. If the detector pixel size is 100 μm, the processor calculates an offset to align and shift the pixel of the imager to one side by 25 μm. Hence, the precision of the fine alignment can be at least 25 μm. At least one mechanism for determining the alignment for a specified precision is provided below.

Referring back to the flowchart 620, if the offset is not within an acceptable tolerance or precision, the offset is added to an existing offset (if any) 632. The steering magnetics adjust the focal spot by the offset and the detector is exposed with the central ray that includes the applied offset 634, and the process repeats until the offset is within an acceptable tolerance or precision. In an example, the offset can be applied to the steering magnetics using a steering signal generated from the TCU. Once the offset is within an acceptable tolerance or precision, the offset can be saved 636. The offset can be saved in the TCU associated with the x-ray tube. In an example, a different offset can be calculated with each tube voltage and tube current combination. The offset can also be calculated based on other characteristics of the x-ray tube, focal spot, or steering mechanism, such as temperature or focal spot size. With increase temperature, the focal spot and the resulting central ray can shift, known as thermal drift. Temperature can be measured via a temperature sensor or calculated based on other parameters (e.g., tube voltage, tube current, running exposure time and non-operating time) In another example, the electronic alignment can be extended to adjust for thermal drift as well as mechanical misalignment. The offset can be calculated with a specific tube voltage, a specific tube current, a specific tube temperature, or other focal spot or steering varying characteristic or parameter in combination.

The electronic alignment or adjustment can provide an automated alignment as measurement values can be directly fed back to an adjustment system (e.g., digital adjustment system) when the x-ray tube or TCU are coupled with the system's imager or detector. The electronic alignment can adjust the focal spot in 2D space utilizing an x-ray tube's existing beam steering or deflection mechanism.

In the electronic alignment portion of the alignment process, the gantry covers do not need to be removed or further mechanical adjustment may not be needed once initially provided. The fine tune alignment moves the electron beam using the steering magnetics within the x-ray, the image is evaluated, and the electron beam is adjusted in either a deterministic or iterative adjustment cycle.

Figure 24:
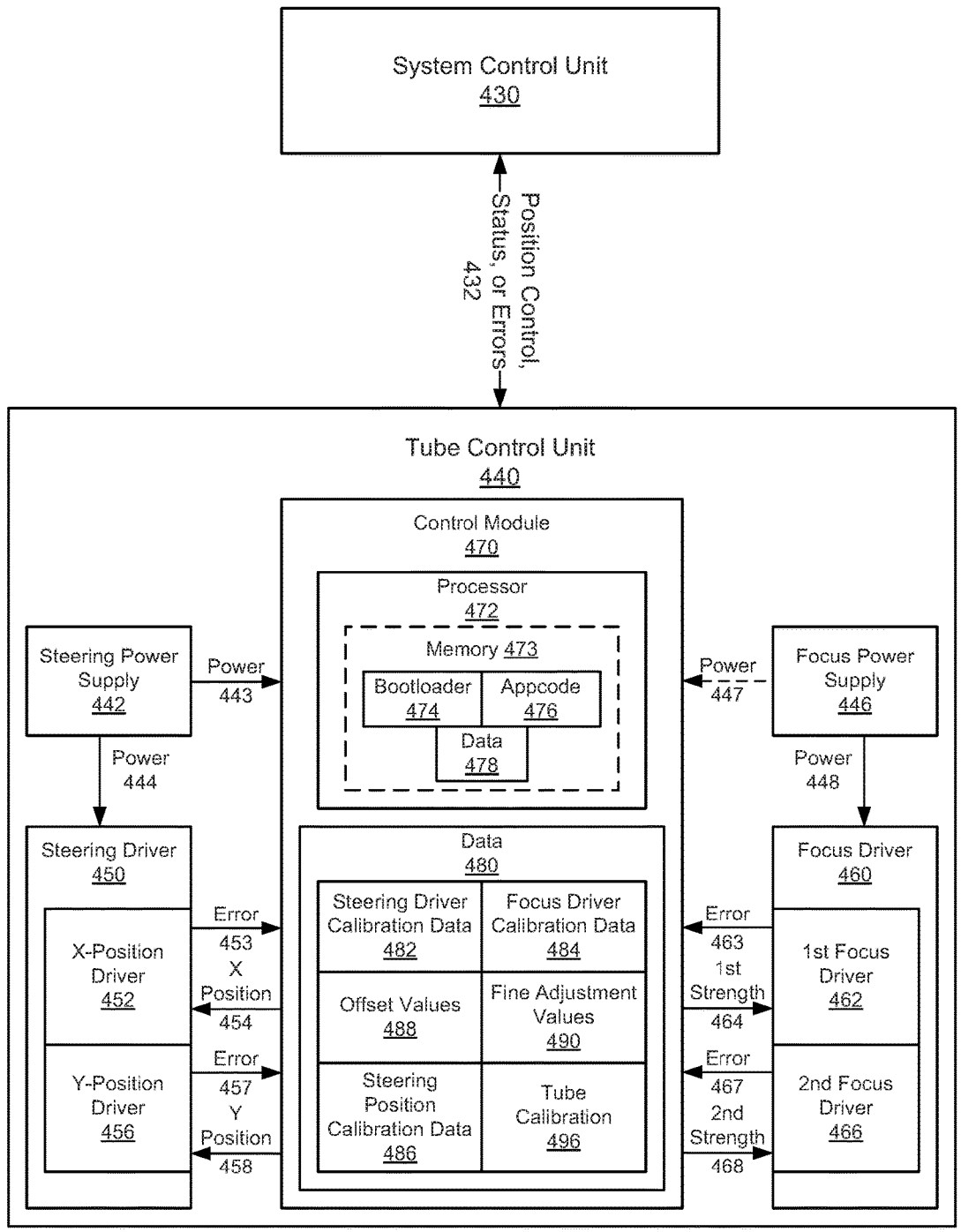
FIG. 24 illustrates a block diagram of an example tube control unit (TCU) and a system control unit.

FIG. 24 illustrates a tube control unit (TCU) 440 with position control, status, or error signals 432 communicated with the system control unit 430. The TCU can be configured for a specific x-ray tube. The TCU includes a focus power supply 446, a focus driver 460, a steering power supply 442, a steering driver 450, and a control module 470. The focus power supply 446 provides power 448 to the focus driver 460 and can provide power 447 to other components (e.g., control module 470). The steering power supply 442 provides power 444 to the steering driver 450 and can provide power 443 to other components (e.g., control module 470).

The focus driver provides the focusing signal (e.g., current) for the coils of the focusing magnetics (340 or 342 of FIGS. 9 and 17; 344 of FIG. 21). The focus driver can include at least one focus driver. In the TCU shown in FIG. 24, the focus driver 460 can include a first focus driver 462 and a second focus driver 466. The first focus driver 462 can provide the focusing signal (e.g., current) to coils of the first focusing magnet (340 of FIGS. 9, 17, and 21), and the second focus driver 466 can provide the focusing signal (e.g., current) to coils of the second focusing magnet (342 of FIGS. 9 and 17; 344 of FIG. 21). Each focus driver 462 or 466 can receive a strength value 464 or 468 from the control module 470 and provide an error signal 463 or 467 (or hand shaking signal) to the control module 470.

The steering driver can include at least one steering driver. In the TCU shown in FIG. 24, the steering driver 460 can include an x-position driver 452 and a y-position driver 456. The x-position driver 452 can provide the steering signal (e.g., current) to the x-axis dipole coils (366B and 366D of FIG. 14) of the steering magnet (330 of FIGS. 9, 17, 18A-B, 19; 334 or FIG. 20; 344 of FIG. 21 [if rotated 45°]), and the y-position driver 456 can provide the steering signal (e.g., current) to the y-axis dipole coils (366A and 366C of FIG. 14) of the steering magnet (330 of FIGS. 9, 17, 18A-B, 19; 344 of FIG. 21[if rotated 45°]). Each steering driver 452 or 456 can receive a position value 454 or 458 from the control module 470 and provide an error signal 453 or 457 (or hand shaking signal) to the control module 470.

The control module 470 includes a processor 472 and data storage 480. The processor can include memory 473 and a central processing unit (CPU), controller, microprocessor, field programmable gate arrays (FPGA), or other programmable component. The memory 473 includes a bootloader 474 for initializing the processor or control module, appcode 476 and data storage 478 for program execution. Data 480 (e.g., tables) can reside on non-volatile memory (e.g., non-volatile random-access memory [NVRAM] or flash memory) or volatile memory (e.g., static random-access memory [SRAM] or dynamic random-access memory [DRAM]). The memory for the data 480 can reside in the memory 473 of the processor 472 or on an external memory chip. The data can include steering driver calibration data 482, focus driver calibration data 484, steering position calibration data 486, offset values 488, fine adjustment values (or user adjustment values) 490, and tube calibration 496. The steering driver calibration data 482 provides adjustments based on steering driver circuitry (e.g., steering driver board). The focus driver calibration data 484 provides adjustments based on focus driver circuitry or focusing driver circuitry (e.g., focus driver board). The steering position calibration data 486 can include position data for deflection or steering patterns (as shown in FIG. 22). Offset data 488 can include calculated values generated during electron central x-ray beam alignment or focus spot alignment, as previously discussed. Fine adjustment values (or user adjustment values) 490 can include additional adjustments or user adjustments in steering (e.g., position correction values) or focusing (e.g., size correction values). The user adjustment values may be a section of the data can be accessed or changed by user control. The changes to user adjustment values may be small or minor and well within the safety parameters of an x-ray tube. Tube calibration can be x-ray tube data specific to an x-ray tube, which may be determined or generated during manufacturing of the x-ray tube. The data may be copied (e.g., initially or on each start up) from the x-ray tube or otherwise provided (downloaded) to the TCU for the x-ray tube. Data may be stored for each combination of tube voltage (e.g., kV), tube current (e.g., mA), focus spot size, temperature, or other relevant x-ray tube or magnetics parameter.

The control module 470 can extract the focusing parameters from the data or calculate the focusing parameters based on input. Once focusing data or values are determined, the focusing data are sent to the focus drivers 460. The system control unit 430 can send a signal to the TCU indicating that the system control unit is ready to activate the driver outputs of the TCU. In response to the ready to activate signal, the TCU communicates to the system control unit that the x-ray tube and TCU is ready for an x-ray exposure. If any errors occur during the process, the errors can be transmitted back to the system control unit.

To increase speed and responsiveness of steering, position changes may be transmitted by discrete line to the TCU. In addition or alternatively, the position or steering information can be transmitted through a sufficiently fast communication interface. In another example, as shown, the position or steering information can be sent to the TCU and the TCU controls the position or steering changes.

In one example, at the startup of the x-ray system, the TCU 440 can retrieve the different tables or data from memory and combine the data to generate the output signals for the x-ray tube. During this setup, various data (e.g., tube calibration data 496) is combined with the calibration data for a specified driver 450, 452, 456, 460, 462, or 466. For steering data, the steering data result can then be offset by the offset data before fine adjustment values 490 (or fine calibration data) are added and merged into final steering data for the specified driver. The final focus or steering data can be stored in the memory 473 and used during the execution of the appcode to generate a focus or steering control signal (416 of FIG. 8). The final focus or steering data can be regenerated each time the x-ray system or TCU starts up or a value in the data updated or modified.

Figure 25A:
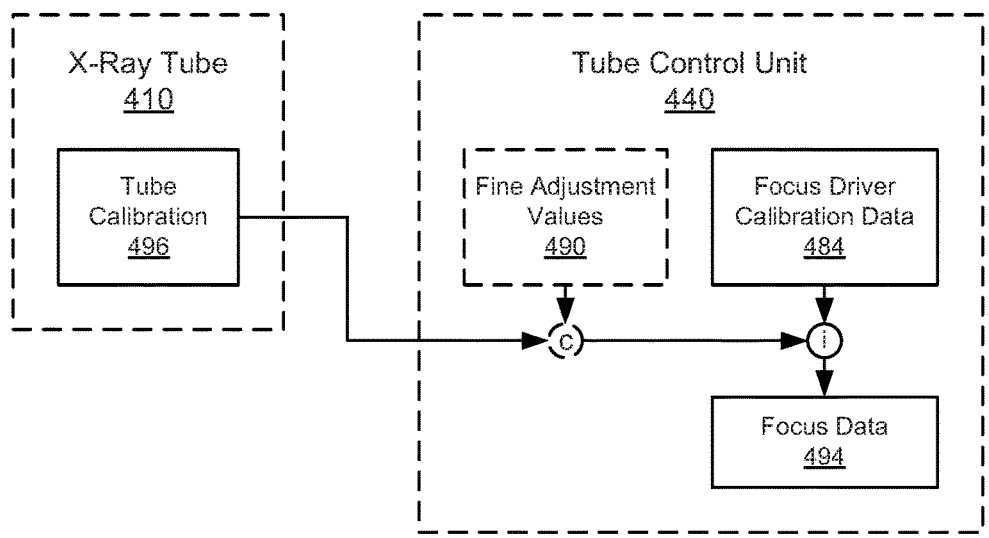
FIG. 25A illustrates a block diagram of example focus data.

FIG. 25A illustrates the generation or combination of focus data 494. Tube calibration data 496 is partially iterated with the focus driver calibration data 484 to generate the focus data 494. In an example, when fine adjustment values 490 are available or used for focusing, the fine adjustment values 490 (e.g., size correction values) are combined with the tube calibration 496 before being partially iterated with the focus driver calibration data 484 to generate the focus data 494.

Figure 25B:
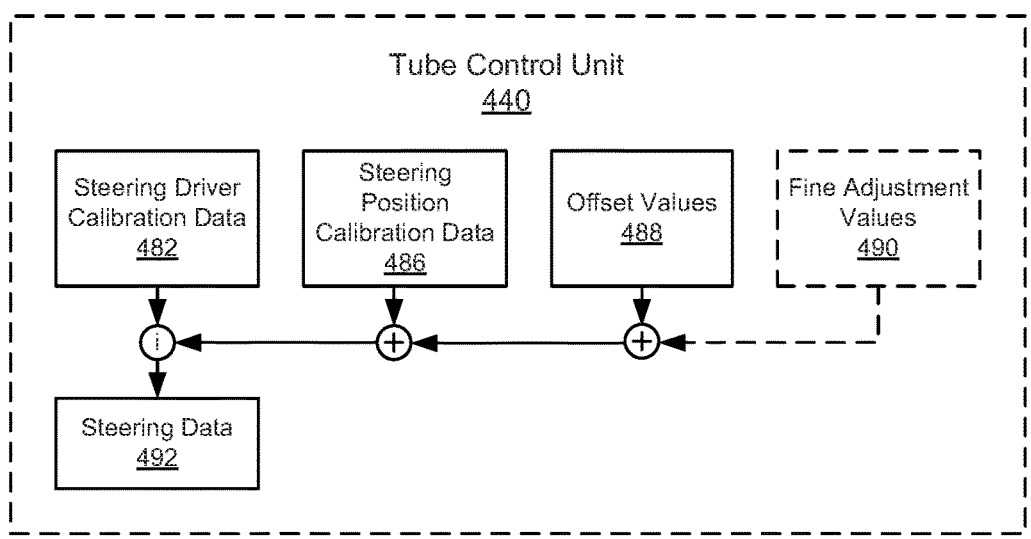
FIG. 25B illustrates a block diagram of example steering data.

FIG. 25B illustrates the generation or combination of steering data. The offset value 488 (e.g., for a tube voltage and tube current) is added to each position of the steering position calibration data 486 and partially iterated with the steering driver calibration data 482 to generate the steering data 492. In an example, when fine adjustment values 490 are available or used for steering, the fine adjustment values 490 (e.g., position correction values) are added to the offset value 488 and each position of the steering position calibration data 486 before being partially iterated with the steering driver calibration data 482 to generate the steering data 492.

Referring back to FIG. 24, combined focus data (e.g., focus tables) or combined steering data (e.g., steering tables) can be generated from the data in memory at startup and reside in the data storage of 478 of the memory 473 of the processor 472. The system control unit 430 can be the control unit of the x-ray system used to interface with and control various components of the x-ray system. For example, a system control unit for a CT scanner can send information to the TCU 440 to setup a scan. The focusing parameters can be dependent on the type of scan to be executed, such as focal spot size, tube voltage, or tube current.

Separating the x-ray tube 410 from the TCU 440, as shown in FIG. 8, allows the x-ray tubes and the TCUs to be interchangeable so if the x-ray tube or TCU changes the x-ray tube calibration data 496 (FIGS. 24 and 25A) can be uploaded to the TCU without any additional data for calibration. Data 480 or 478 may be stored on the x-ray tube or the TCU or exchanged between the x-ray tube and the TCU.

Referring back to FIG. 22, the offset value can be applied to a deflection pattern or steering pattern 500, as represented by 1'-8'. The offset may be limited by physical structure (e.g., x-ray tube), mechanical properties of the x-ray tube, or deflection position (e.g., an edge of the imager). For example, the amount of deflection allowed can be determined by the track width and a throat size of the tube (e.g., in the drift region). The TCU driver design can determine the speed at which position or steering changes can occur (e.g., offset or deflection position). In an example, the TCU can steer a central x-ray beam to a position on an x-ray imager in less than 30 microsecond (≤30 μs). If less deflection is needed, the speed to change position can be faster. The speed for a position or steering change can be determined by the driver voltage and the amount of deflection needed. The TCU may limit the amount of deflection based on the driver strength. In an example, the driver strength may be adjusted or selected for the TCU design.

Figure 26:
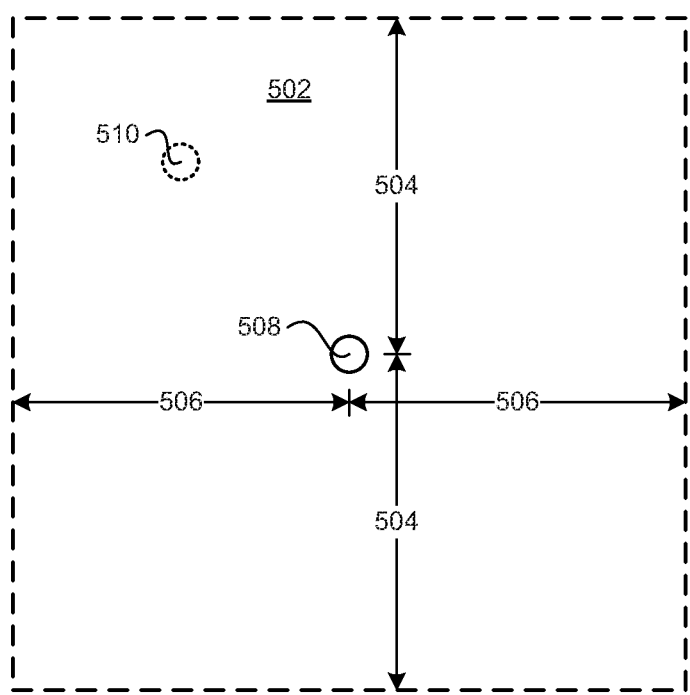
FIG. 26 illustrates a range of central x-ray beam offset on an x-ray detector.

FIG. 26 illustrates offset region 502 with a vertical offset range (limit) 504 and a horizontal offset range (limit) 506 surrounding a central x-ray beam without offset 508. In an example, the offset range can be less than 1 mm. A central x-ray beam with offset 510 can occur within the offset region. Based on the physical structure or deflection position, the vertical offset range or horizontal offset range on either side of the central x-ray beam without offset may not be symmetrical or may vary from each other.

Focusing can limit the focal spot size, with can be determined by the focusing magnetics, the focus driver current, the target material, and the x-ray tube power (e.g., tube voltage and tube current). The x-ray target (on the anode) may withstand a certain amount of heat density before damage occurs. As a generalization, more power can be utilized with larger focal spot.

For both mechanical and electronic tube alignment a reference object, referred to as a phantom (e.g., an alignment phantom or a resolution phantom), can be used. Alignment can be determined on both rotating and stationary (non-rotating) x-ray systems. It may be simpler to perform an initial alignment on an x-ray system in a stationary position. On a stationary x-ray system, such as a digital x-ray system or mammography system, or a rotational x-ray system in a stationary position, the alignment phantom can be a ball, a pin, or a long cylinder placed at the center of the x-ray detector. Sometimes, the pin, ball or cylinder is combined with other features in an x-ray phantom for image quality. However, the function of the pin, ball, or cylinder is similar. Independent of the phantom type, the purpose of the phantom is to align the central x-ray beam of the x-ray system with a specified location of the x-ray imager (e.g., the center of the x-ray imager). The x-ray imager can include film or an electronic detector. In many cases, other components (e.g., collimator or laser cross hairs) may also be aligned with the central x-ray beam and the imager. For example, laser cross hairs are often used in patient setup to align the x-ray imager with the patient anatomy to be imaged. In an x-ray system that is perfectly aligned, the pin is located directly under the central x-ray beam and the phantom produces a circle or round spot in the image. If the spot is not at the center of the imager, another step can be to shift the phantom or x-ray source until the phantom or x-ray source are aligned with the imager.

If the phantom is misaligned with the x-ray source, the diameter and the ratio of the perpendicular diameters may be different. A careful examination can also show that the density of the spot or circle is not homogeneous and has different contrast levels on each side of the spot. The amount distortion or deviation from the actual phantom diameter can have a direct geometric relation to the offset from the central x-ray beam. The exact amount of offset can depend on the magnification, beam angle, and other factors for the x-ray system.

The distortion or deviation of the image can be visually detected or the distortion or deviation of the image can be measured in the image using various computer applications or programs. With automation in measuring distortion in images to determine offset, the electronic central x-ray beam alignment process can generate a final offset value which aligns the central x-ray beam with the specified location of the imager within just a few minutes or less.

Figures 27A, 27B:
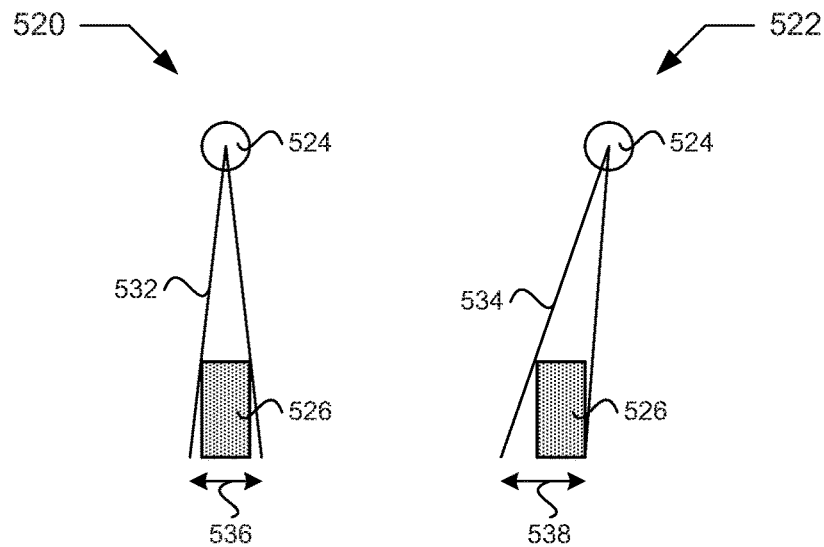
FIGS. 27A-B illustrates variations of image dimensions with differences in x-ray source location.

FIGS. 27A-B illustrates variations of image dimensions with differences in x-ray source location. FIG. 27A shows an aligned phantom with x-ray source 520 with an aligned x-ray beam 532 that occurs when an x-ray source 524 is aligned with a phantom 526. FIG. 27B shows a misaligned phantom with x-ray source 522 with a misaligned x-ray beam 534 occurs when the x-ray source 524 is misaligned with the phantom 526. The image dimensions 536 (i.e., aligned phantom projected width) of the aligned x-ray beam 532 is smaller than the image dimensions 538 (i.e., misaligned phantom projected width) of the misaligned x-ray beam 534.

In a stationary x-ray system or rotational x-ray system in a stationary position, the phantom is placed at purported center of the detector and an image is acquired. The phantom can be moved until the phantom is placed at the center of the imager. Once the phantom is centered, the position of the x-ray source can be adjusted either by the mechanical or electronic alignment process described. An image is acquired, the distortion measured, and an offset is calculated, and an electronic adjustment or mechanical alignment of the x-ray source is made. The configuration with the offset adjustment can be verified with another image. The alignment of the phantom with the imager and the central x-ray beam can affect each other, so the position of the phantom and adjustment of the central x-ray beam may be iterated until a correct alignment between the three components is achieved (i.e., phantom, imager, and central x-ray beam).

Figure 28:
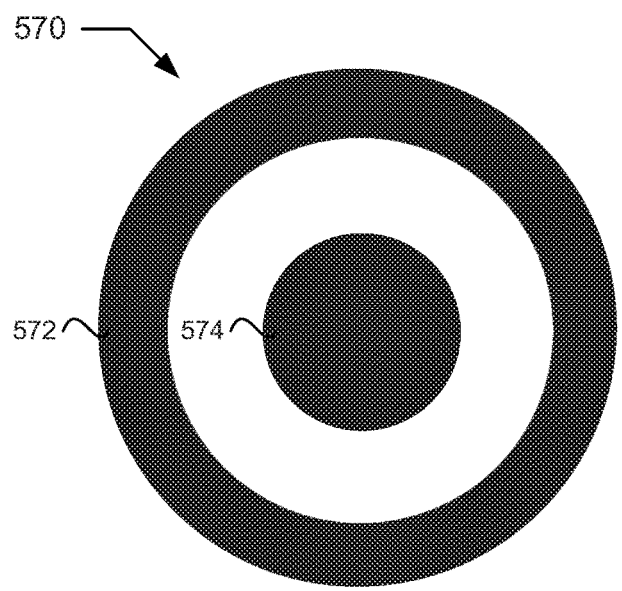
FIG. 28 illustrates an example of a ring phantom with a center point.

FIG. 28 illustrates an example of a ring phantom with a center point 570 which includes a ring feature 572 with a center point 574 within the ring. The ring phantom 570 may also be used in alignment and can provide additional information. The center point (spot) 574 can be relatively flat (as the effect of the distortion decrease with height) with a small diameter, which can allow alignment of the phantom with the imager. The ring feature is thicker or higher and produces a distortion or deviation in shape when the ring phantom is not aligned properly with the x-ray source (e.g., x-ray tube). The ring phantom can require less iteration steps for alignment than some other phantoms.

In rotational x-ray systems (e.g., CT systems), a misalignment of the x-ray beam with respect to the detector and a central axis of the x-ray system can result in image artifacts, such as streak artifacts. Depending on the amount of misalignment, the image quality can decrease as streak artifacts become more significant with larger misalignment. During alignment, a phantom with a pin or ball at the center is placed on the couch or table of the x-ray system (near the central axis of the x-ray system) so the pin or ball is centered at the rotation axis of the rotational x-ray system. The placement of the phantom can be verified by a scan and examining the artifacts and geometric size of the phantom in the image. If the phantom is not centered correctly the image can show a distortion. If a stationary image is taken (gantry is not rotating), the measurements can be similar to a stationary x-ray system to align the central x-ray beam with the detector array used on a rotating x-ray system. In many cases, an offset of as small as ¼ pixel size can be used to minimize artifacts and increase image quality.

Another method to align the central x-ray beam to the imager, thus improving the resolution of the image is using line pair phantoms. If a certain separation is not detectable, alignment may not be correct and the x-ray tube or central x-ray beam may need to be adjusted. The adjustment can be made until the line pair is distinguishable or visible. FIGS. 29A-B illustrate examples of different sizes of line shape phantoms used for alignment or resolution determinations. FIG. 29A shows three small cuboid shaped line shape phantoms 540A-C. FIG. 29B shows three large cuboid shaped line shape phantoms 550A-C. The ends (or two faces) of the cuboid can have a square shape and each side of the square can have length 542 or 552 that is substantially similar to the space 544 or 554 between the line phantoms. A phantom device may include varying sizes of line shaped phantoms for different levels or degrees of alignment or resolution.

FIGS. 29C-E illustrate different images that can result from the line shape phantoms shown in FIGS. 24A-B, which can be based on precision of the alignment of the imager to the central x-ray beam. FIG. 29C shows distinct and separate line shape phantom images 560A-C, which can be the result of correct alignment of the imager to the central x-ray beam. FIG. 29D shows a compact line shape phantom images 562A-C, which can be the result of slight misalignment of the imager to the central x-ray beam. FIG. 29E shows blurred line shape phantom image 564, which can be the result of misalignment of the imager to the central x-ray beam.

Other mechanisms and phantoms may also be used to align the imager to the central x-ray beam of the x-ray tube (or central axis of an x-ray system).

Method of Aligning a Central X-Ray Beam of an X-Ray Tube to a Radiation Imager

Figure 30:
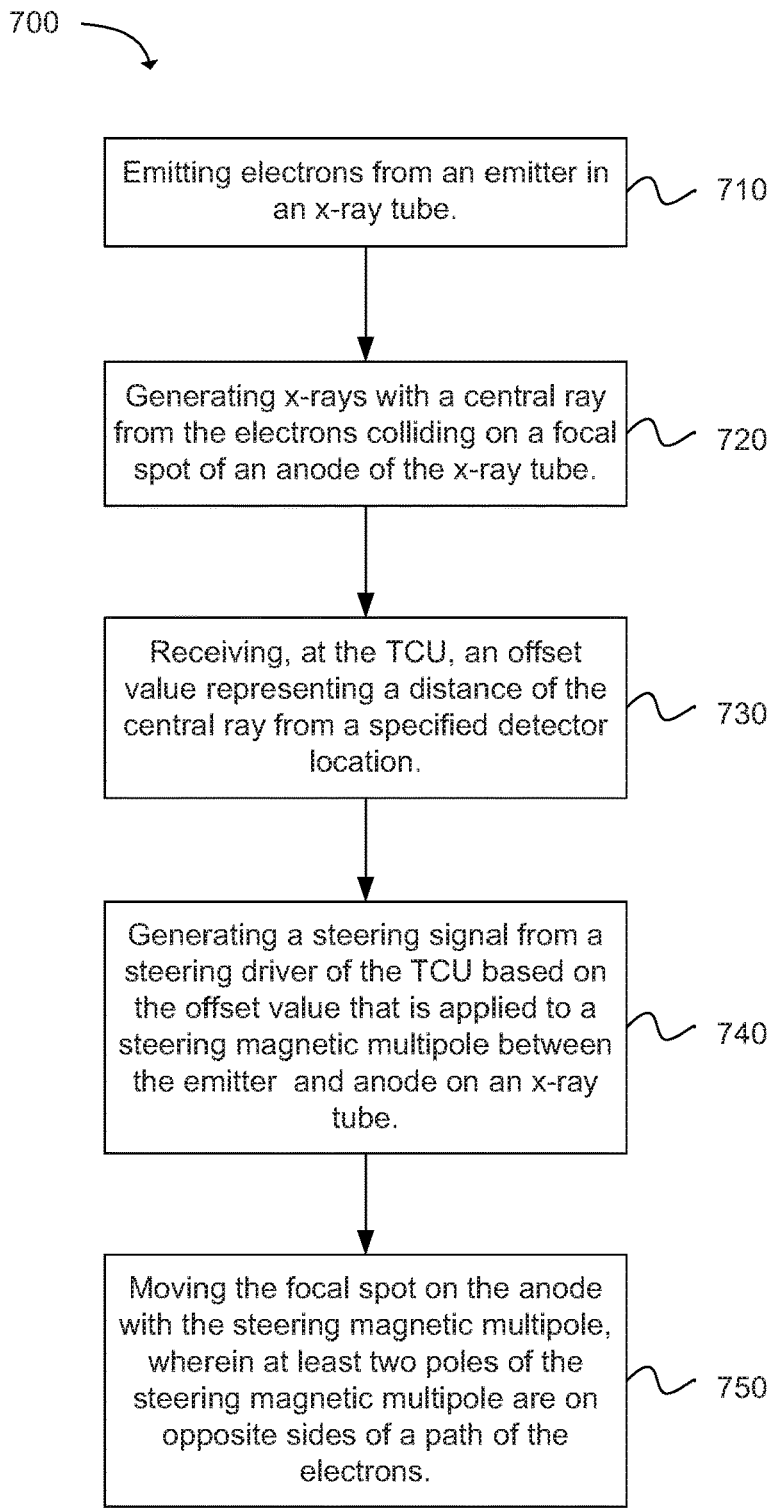
FIG. 30 is a flowchart illustrating an example of a method of aligning a central ray of an x-ray tube to a radiation detector using a tube control unit (TCU).

The flowchart shown in FIG. 30 illustrates a method 700 of aligning a central ray of an x-ray tube to a radiation detector using a tube control unit (TCU). The method includes the step of emitting electrons from an emitter in an x-ray tube, as in step 710. The step of generating x-rays with a central ray from the electrons colliding on a focal spot of an anode of the x-ray tube follows, as in step 720. The next step of the method includes receiving, at the TCU, an offset value representing a distance of the central ray from a specified imager location, as in step 730. The method can further include generating a steering signal from at least one steering driver of the TCU based on the offset value that is applied to a steering magnetic multipole between the emitter and the anode on an x-ray tube, as in step 740. The next step of the method can include moving the focal spot on the anode with the steering magnetic multipole to align the central ray to the specified imager location, as in step 750. At least two poles of the steering magnetic multipole are on opposite sides of a path of the electrons.

The electronic focal spot alignment (or central ray alignment) technology described herein can align a central x-ray beam of an x-ray tube to an imager by providing a position or value to the tube control unit (TCU) to adjust the offset in a specified direction. While adjustment of the offset can still be an iterative process, the speed, accuracy, and precision of the adjustment can increase. The precision and accuracy of an alignment including the electronic alignment can be increased as the amount of deflection is determined by the electronic resolution. In contrast, mechanical adjustment is limited to the measuring devices used and the ability of the technician to move the tube accurately. Often the mechanical adjustment in one direction can result in small translational or rotational motions in another direction, which can degrade or invalidate the mechanical alignment. Accuracy and precision in the electronic alignment can be determined by the measurement system and the resolution inherent in the electronics, which can be far more precise than a service technician. Since mechanical adjustment is not required after a course mechanical adjustment, the process can be automated and can be performed without a service technician or without a partial disassembly of the x-ray system, as no mechanical access to the x-ray tube and the tube controls may be needed. The electronic alignment can be performed by a qualified operator on site. For example, an operator may place a test phantom in the x-ray system and run the automated alignment procedure, which can eliminate a service call to a technician to align the tube or check tube alignment. Alignment checks and verification of x-ray system performance can be performed at any time and needed adjustments can be made without the involvement of a service technician. In addition, the protective covers of the x-ray system may not need to be removed. In one example, the total calibration or alignment time can be reduced from ½ to 1 hour down to a few minutes.

In addition to the static offset adjustment, the electronic alignment also provides a mechanism to adjust for dynamic variations on the x-ray tube due to force and thermal expansion or contraction. The electronic alignment described also overcomes challenges from conventional steering mechanisms and processes. Challenges with conventional steering mechanisms include a deflection that results in blooming of the focal spot over the range of various tube current and tube voltage combinations and an increase in focal spot size due to the additional length of the throat of the x-ray tube (i.e., in the drift region) due to the added deflection mechanism in the drift region. Other challenges with conventional steering mechanisms include single sided magnetics, which can cause geometric distortion of the focal spot. The additional mechanisms (e.g., focusing magnetics and magnetic poles on opposite sides of an electron beam) described can avoid blooming and precisely control the focal spot size and position.

The electronic focal spot alignment (or central ray alignment) technology using a steering or deflection mechanism can be used to increase image resolution by superimposing a static or dynamic offset to keep the focal spot in alignment, which can thereby optimize image quality and reduce geometric distortion. The focusing mechanism in line with the steering or deflection mechanism can have the additional benefit of reducing or eliminating focal spot bloom. Blooming of focal spots can occur due to the increase of the tube current (i.e., higher electron density or higher current density) and decrease in tube voltage (i.e., lower electron speed). Having an additional focusing mechanism can control, reduce, or minimize blooming.

Electronic Calibration of Focal Spot Size and Position

The steering magnetics and focusing magnetics of the x-ray tube along with the TCU can also provide electronic calibration of focal spot position (or central ray position) or electronic calibration of focal spot size (focal spot dimensions, central ray intensity, or x-ray beam energy distribution). In an x-ray tube, the focal spot size can be defined, in part, by a tube voltage and tube current setting. The focal spot size can change due to electron beam space charge effects at different tube voltages and tube currents. Changing the tube voltage or the tube current can generate focal spot blooming, as previously described. Using the steering magnetics or focusing magnetics described, the focal spot size can be adjusted to a uniform size over a dynamic range of tube voltages and tube currents to avoid the blooming of the focal spot, which can improve the image quality for the various tube voltage and tube current combinations.

Conventionally, the deflection (used to generate deflection positions) is generated using a set of tube operation parameters (e.g., a specific tube voltage and tube current). The deflection may only be accurate at the specific tube operation parameters. At other positions, the deflection may vary with respect to the focal spot location.

Figure 31A:
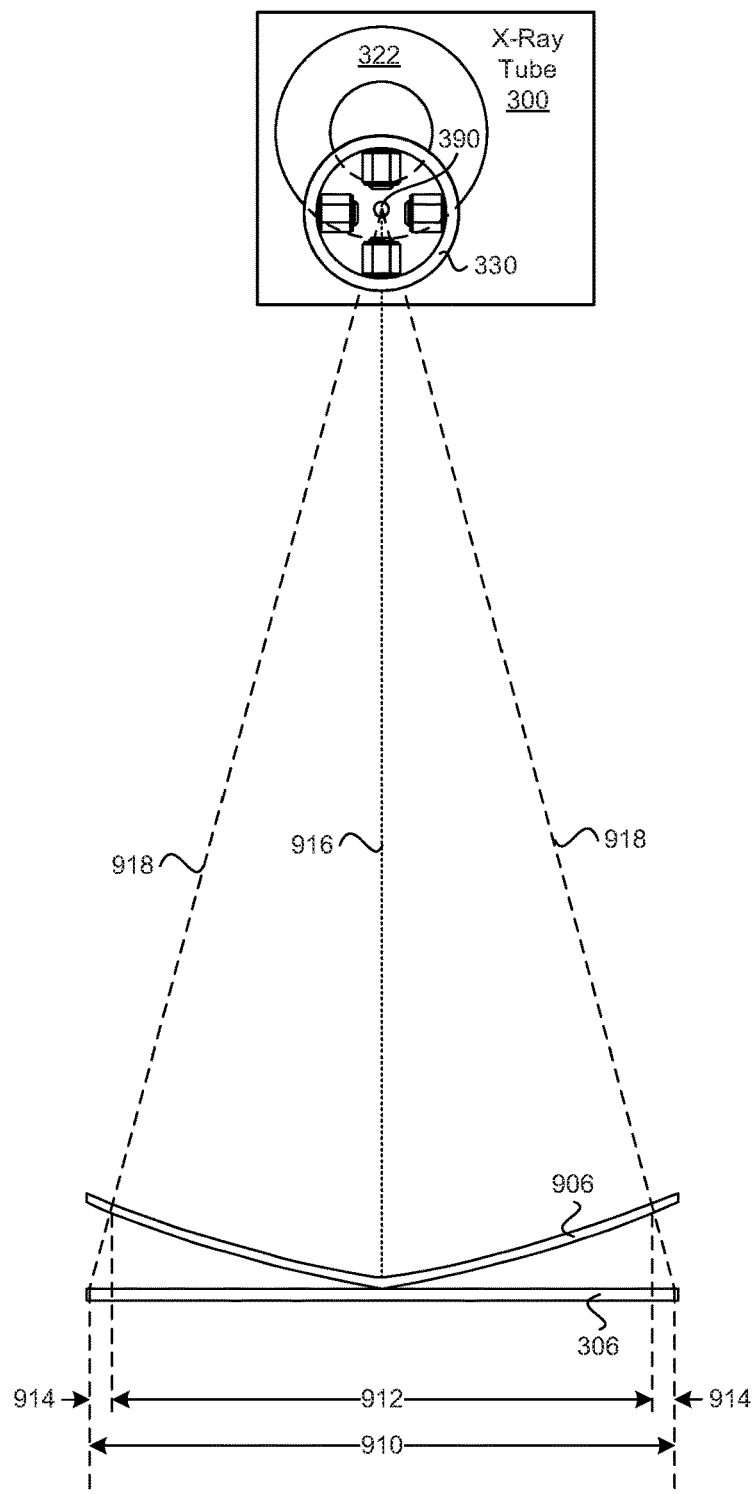
FIG. 31A illustrates an error in deflection range between central x-ray beam on a flat x-ray detector and a curved x-ray detector.
Figure 31B:
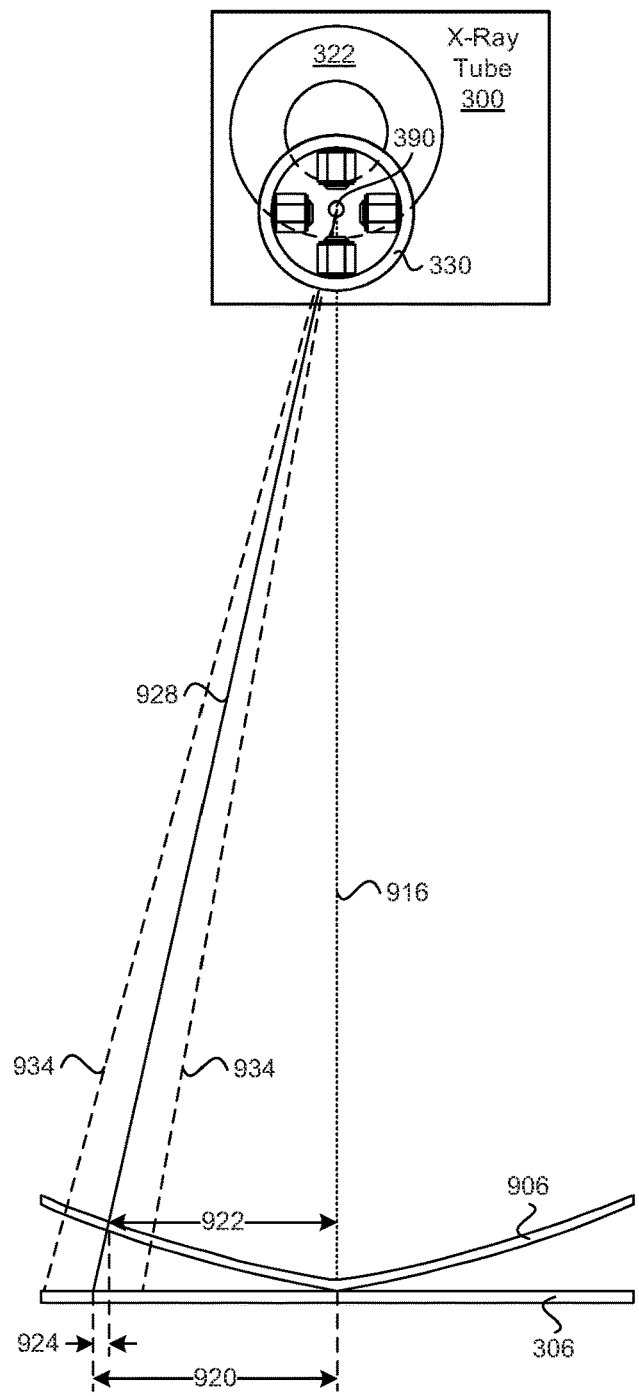
FIG. 31B illustrates an error in position between central x-ray beam on a flat x-ray detector and a curved x-ray detector.
Figure 31C:
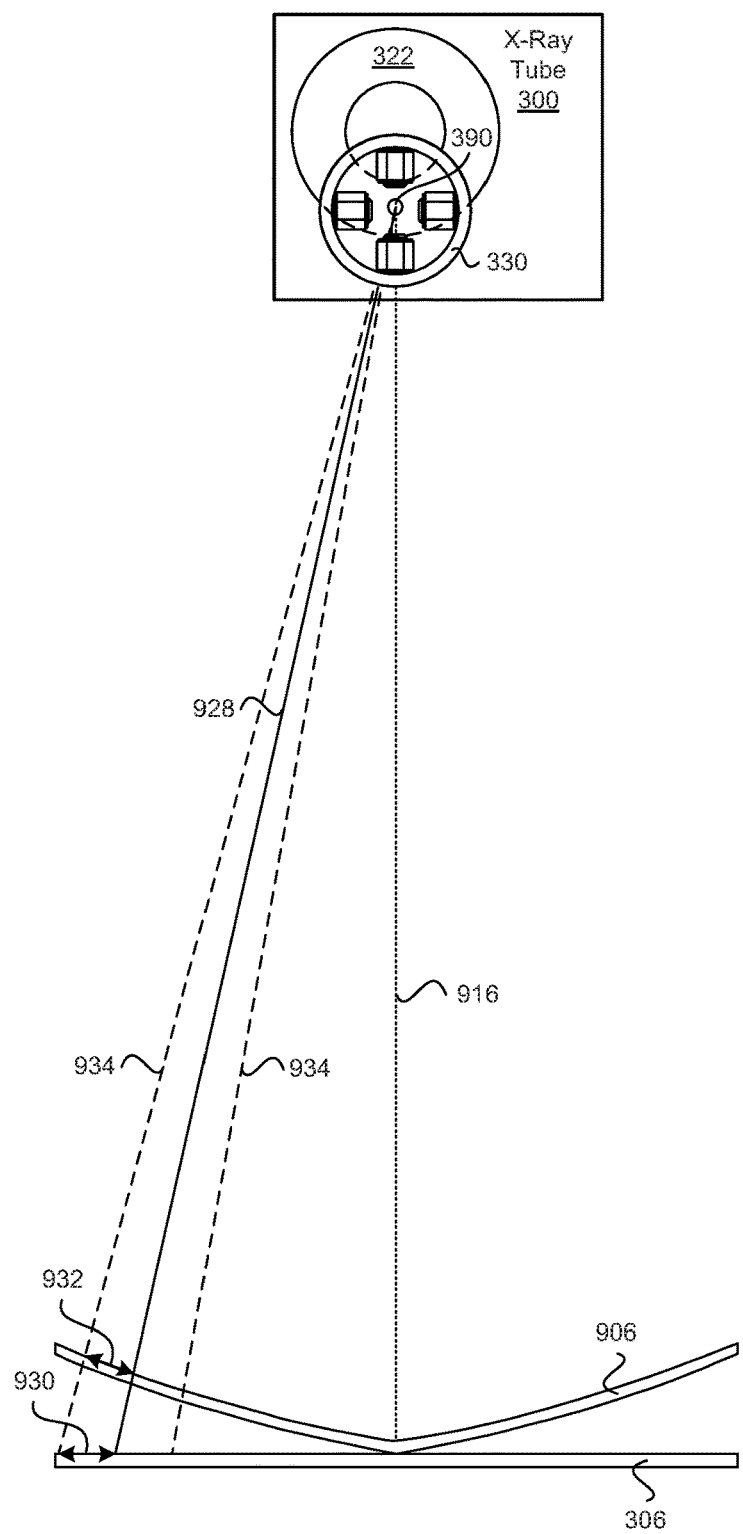
FIG. 31C illustrates an error in size between central x-ray beam on a flat x-ray detector and a curved x-ray detector.

Many x-ray tubes can be used on different types of x-ray systems (e.g., from different manufacturers). Typically, during x-ray tube calibration, a flat detector is used to calibrate the deflection distance and focal spot size. However, x-ray detectors 240 used in rotating x-ray systems are mounted on a circular gantry and are intrinsically arc shaped or curved, as shown in FIGS. 2 and 4-6. The curved shape in the x-ray detector can generate distance differences when compared to a flat detector, as illustrated in FIGS. 31A-C. Because gantry dimensions, such as a gantry diameter and a distance of the x-ray detector from the x-ray tube, are often unknown to an x-ray tube manufacturer or can be difficult and expensive to reproduce during a calibration process (with the gantry), the calibration using the flat x-ray detector can have some distortions or errors when applied to the curved detector of the rotating x-ray systems. The focusing and steering mechanism of the x-ray tube along with the TCU can be used to correct for aperture errors existing due to the difference in calibration with a flat detector versus a curved detector on a rotational x-ray system or to adjust steering or focusing to optimize the imaging results for a specific application.

FIG. 31A illustrates an error (i.e., secondary error) in deflection range between a deflected central x-ray beam 918 on a flat x-ray detector 306 and a curved x-ray detector 906 (i.e., flat x-ray detector central x-ray beam deflection range 910 and curved x-ray detector central x-ray beam deflection range 912). A secondary error is a difference in focal spot size or position between a flat detector and a usually curved detector on a rotatable gantry. A half of the error 914 between a central x-ray beam deflection range on the flat x-ray detector and the curved x-ray detector is shown on each side of the detectors. Because the curvature of a detector used by specific user is usually not available a priori (i.e., before calibration), the focal spot sizes and deflections can have secondary error. A mismatch of focal spot size and deflection errors can have a negative impact on image quality and image signal to noise.

FIG. 31B illustrates an example of a position error 924 introduced by the detector curvature. The position error 924 is the difference between a distance 920 between a deflected central x-ray beam 928 and a central x-ray beam at a specified reference position 916 (e.g., the x-ray detector geometric center point) on the flat x-ray detector 306 and a distance 922 between the deflected central x-ray beam 928 and the central x-ray beam at the specified reference position 916 on the curved x-ray detector 906.

FIG. 31C illustrates an example of a size error introduced by the detector curvature. The deflected central x-ray beam 928 is shown with an x-ray beam outline 934 representing x-rays of specified intensity or power level. The x-ray beam outline 934 can illustrate a change in focal spot size. The flat x-ray detector central x-ray beam size 930 with the specified intensity (representing a focal spot size applied to the flat x-ray detector) can have a different size from the curved x-ray detector central x-ray beam size 932 with the specified intensity (representing a focal spot size applied to the curved x-ray detector).

As discussed previously, the shift in the position and the change in focal spot size have a negative effect on image quality. Electromagnetic deflection allows for fine calibration of each position for each of the x-ray tube's operating parameters. In an example, referring back to FIG. 8, x-ray tube 410, the x-ray detector 420, the system control unit 430, and the TCU 440 form a closed loop system that can be used to automatically calibrate each central ray position or focal spot without having to return the tube or the TCU to a manufacturer for calibration and without the intervention of a service technician. The x-ray tube 410 in combination with the TCU 440 allows an attached system control unit system 430 to adjust and calibrate each position for various tube operation parameters, such as focal spot position (or central ray position) or focal spot size (or central ray intensity or x-ray beam energy distribution), which can be used to avoid, reduce, or minimize the introduction of imaging errors (e.g., secondary errors) into the imaging chain. In an example, the calibrations adjustments can be accomplished at the system level without the need of a service call to a technician to perform the calibration. As a result, operators can verify calibration in accordance with their daily, monthly, quarterly, semiannual, or annual quality assurance procedures and recalibrate the imaging chain without the need for a technical service call. In another example, calibration verification can be performed within a few minutes or less and without the intervention of a technician.

Figure 32:
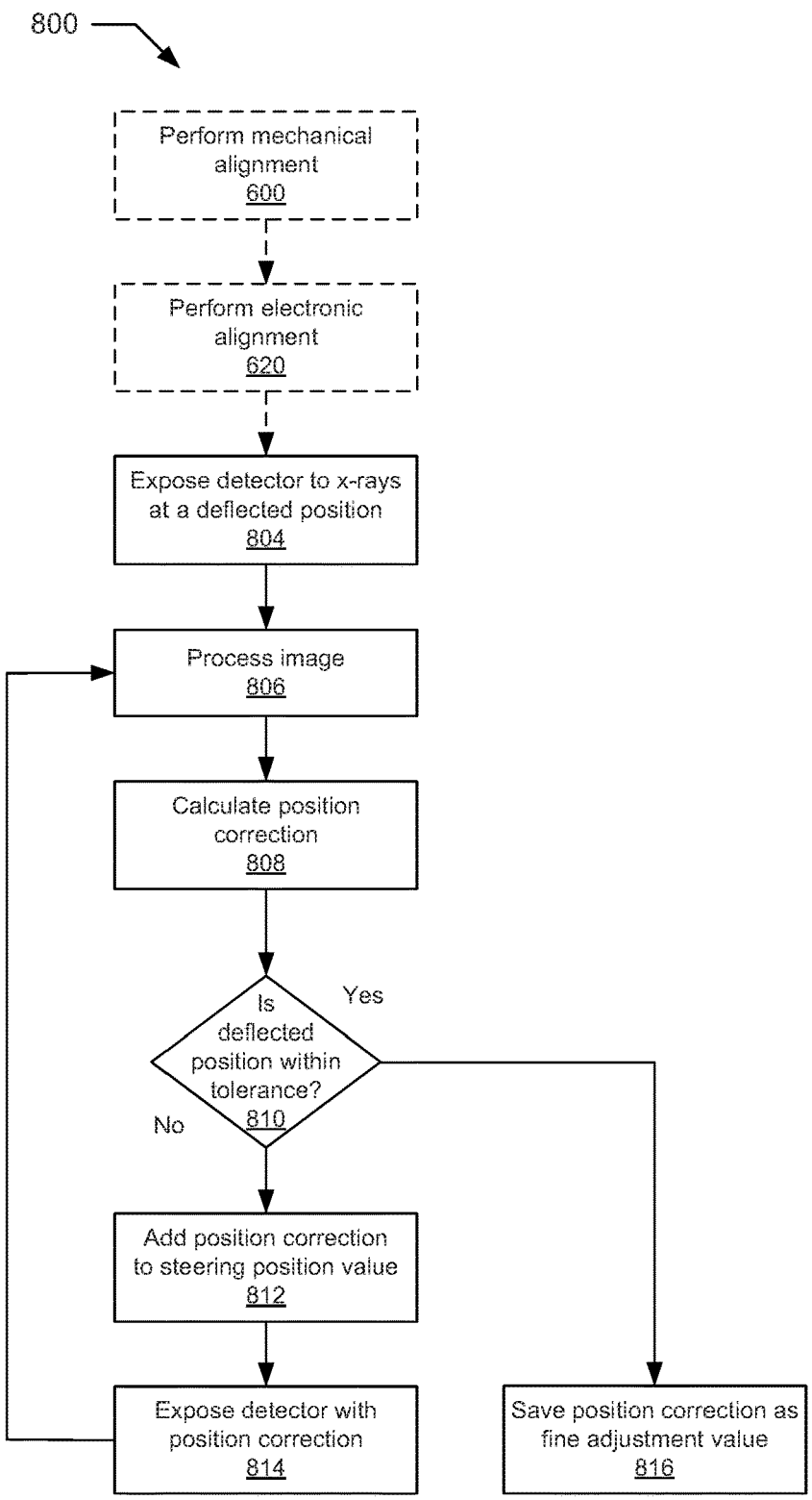
FIG. 32 illustrates a flowchart for an example adjustment of a focal spot (or a central x-ray beam) for positions in a focal spot deflection pattern.

FIG. 32 illustrates a flowchart of the electronic adjustment of a focal spot position (or a central x-ray beam position) of the x-ray tube for various steered positions 800 (e.g., in a focal spot deflection pattern), which can be used to correct secondary error. A relatively coarse mechanical alignment may be performed 600. Then, the electronic central ray alignment of the x-ray tube may be performed 620. The imager or detector is exposed to x-rays from the x-ray tube at a deflected position 804. The exposure can be performed with an alignment object or phantom. The image of the x-ray detector is processed 806 by a processor in the x-ray detector or the system control unit, and the processor calculates a position correction (or position correction value or position adjustment) representing a distance of a deflected central ray (i.e., actual deflected central ray position) from a specified deflection position (i.e., the targeted deflected central ray position with or without the position correction) 808. In one example, the position correction represents a 2D distance. In another example, the position correction represents a 1D distance. The processor determines if the deflected central ray position (with or without the position correction) is within an acceptable tolerance or precision 810. In an example, the position correction can have an acceptable tolerance or precision that is smaller than an offset value used for each of the central ray positions. For example, if the offset value can have an acceptable tolerance or precision that is <25 μm (from perfect alignment), the position correction can have an acceptable tolerance or precision that is <5 μm (from perfect alignment).

If the position correction is not within an acceptable tolerance or precision, the position correction is added to the steering position value (e.g., used to generate the deflected position) and an existing position correction (if any) 812. The steering magnetics adjust the focal spot by the adjusted or corrected steering position value that includes the position correction and the detector is exposed with the adjusted deflected central ray 814, and the process repeats until the position correction is within an acceptable tolerance or precision for the deflected position. In an example, the position correction can be applied to the steering magnetics using a steering signal generated from the TCU. Once the position correction is within an acceptable tolerance or precision, the position correction can be saved as a fine adjustment value 816. The position correction can be saved in the TCU associated with the x-ray tube. In an example, a different position correction can be calculated with each tube voltage and tube current combination. Referring back to FIG. 22, the deflection position can be calibrated with the position correction at a position in an allowed or acceptable steering range 503.

Figure 33:
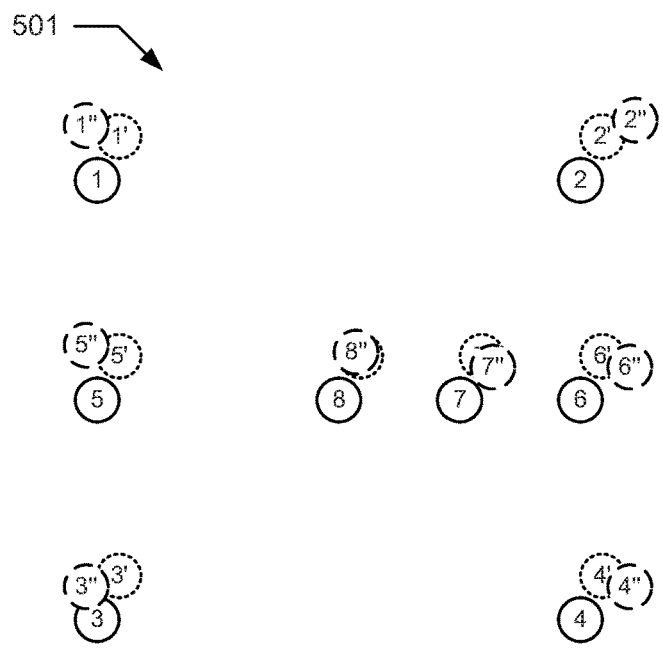
FIG. 33 illustrates an example focal spot deflection pattern showing central x-ray beam offset and fine adjustment.

In another example, different position corrections can be calculated with each deflection position or steering position (in a deflection pattern) for each tube voltage and tube current combination. FIG. 33 illustrates a central ray deflection pattern 501 (or a focal spot deflection pattern) showing the eight deflection points 1-8 and the eight deflection points 1'-8' with offset, shown in FIG. 22, along with eight deflection points 1"-8" with offset combined with different position corrections for each deflection point 1"-8". Each deflection point 1"-8" illustrates a different position correction from the other deflection points.

Figure 34:
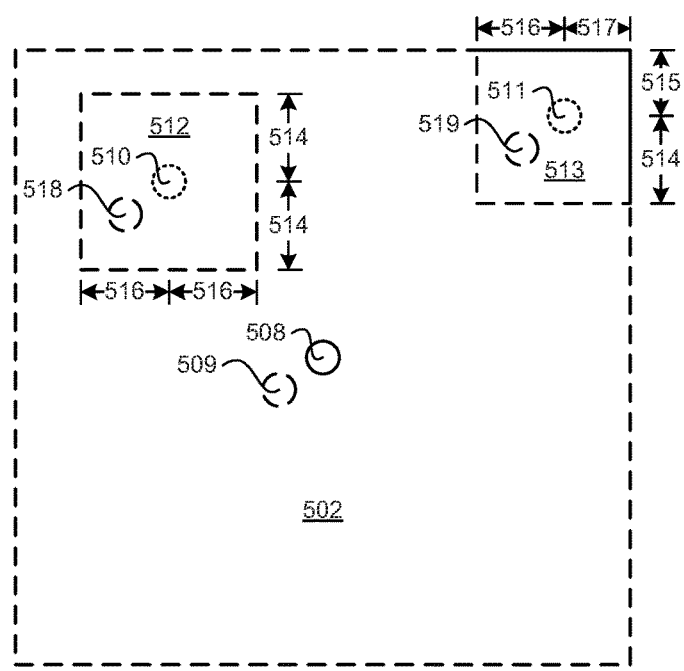
FIG. 34 illustrates a range of central x-ray beam fine adjustment on an x-ray detector.

In another configuration, the different position corrections can be combined with other alignment values (e.g., the offset value) or adjustment values. FIG. 34 illustrates a position correction region (or fine adjustment region) 512 for central x-ray beam position corrections (e.g., fine adjustment) on an x-ray detector overlaid on an offset region 502. The position correction region 512 can be defined by a vertical position correction range (limit) 514 and a horizontal position correction range (limit) 516 surrounding a central x-ray beam with offset 510. A central x-ray beam with offset and position correction 518 can occur within the position correction region 512. In an example, the position correction range can be less than 50 µm. In an example, the position correction range can be less than 10 µm. Based on the physical structure of the x-ray tube or deflection position, the vertical position correction range or horizontal position correction range on either side of the central x-ray beam with offset may not be symmetrical or may vary from each other.

For example, if a central x-ray beam with offset 511 (i.e., a different offset value from position 510) is on an edge of the offset region 502 or the allowed steering range 503, the position correction region 513 can be reduced with a smaller vertical position correction range 515 or smaller horizontal position correction range 517 surrounding a central x-ray beam with offset 511. A central x-ray beam with offset and position correction 519 can occur within the position correction region 513. In another example, the position correction can be used without the offset, so a central x-ray beam with position correction 509 can occur within the position correction region (not shown).

Figure 35:
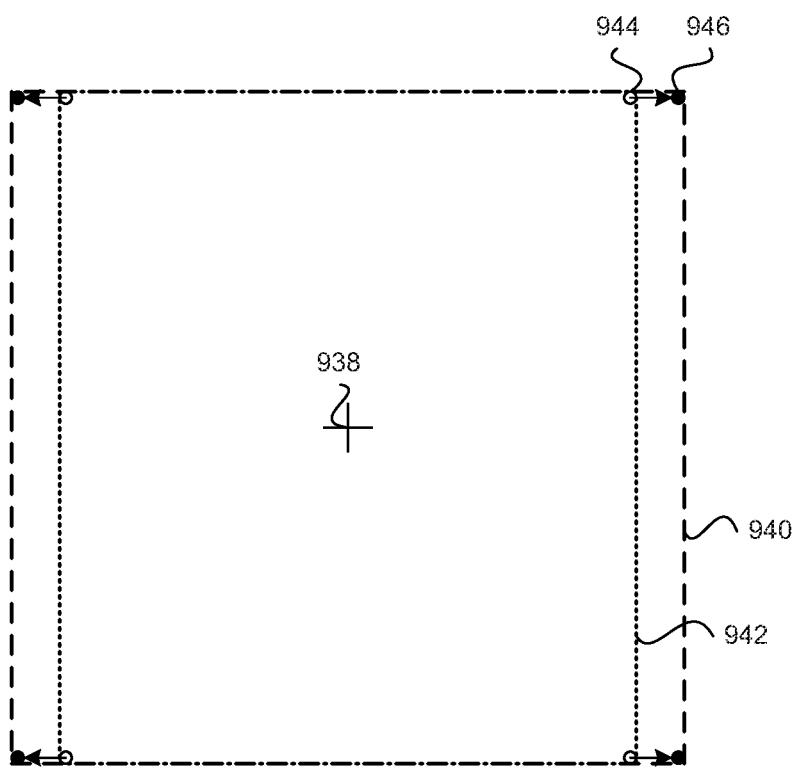
FIG. 35 illustrates distortion between a flat x-ray detector and a curved x-ray detector.

FIG. 35 illustrates a top view of a curved x-ray detector 906 (FIGS. 31A-C) overlaid on a flat x-ray detector 306 (FIGS. 31A-C), which illustrates the distortion between the flat x-ray detector and the curved x-ray detector. A flat x-ray detector outline 940 of an image is shown relative to a curved x-ray detector outline 942 of an image and a center point 916 (FIGS. 31A-C) or 938 on the flat x-ray detector and the curved x-ray detector. An edge point 944 of a curved x-ray detector that was calibrated to a flat x-ray detector can be adjusted, shifted, or calibrated to shifted edge point 946 of a curved x-ray detector to match a calibration or an image generated on the flat x-ray detector. The center point 938 may not have a corrected position or an adjusted position. The rest of the points at other positions (e.g., intermediate positions) may also be adjusted proportionate to known or measured calibrated positions (with position correction). The intermediate positions can be calculated from the known deflection point corrections.

Figure 36:
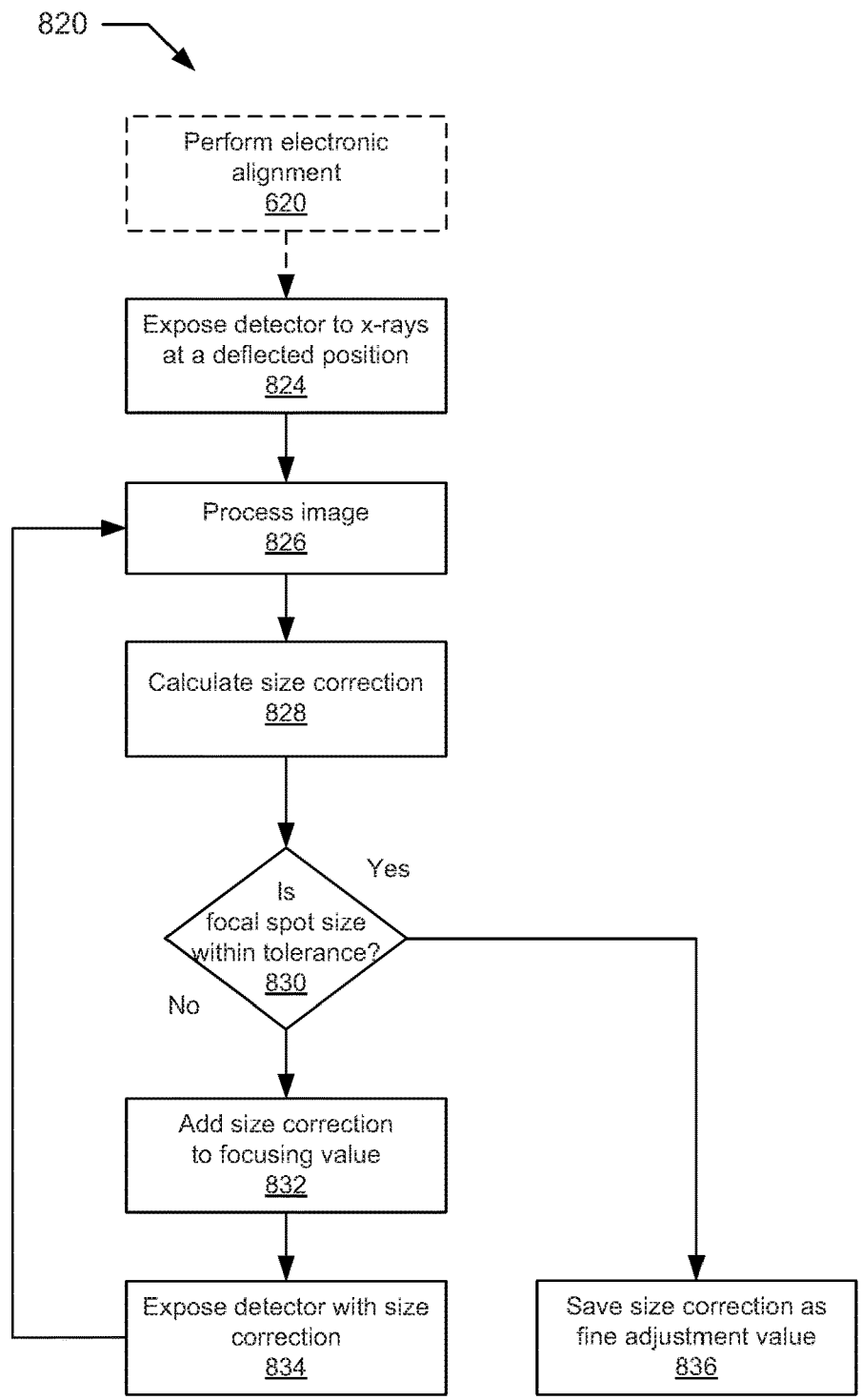
FIG. 36 illustrates a flowchart for an example adjustment of a focal spot size (or a central x-ray beam intensity) for positions in a focal spot deflection pattern.

FIG. 36 illustrates a flowchart of the electronic adjustment of a focal spot size (or central ray intensity or x-ray beam energy distribution) of the x-ray tube for various steered positions 820 (e.g., in a focal spot deflection pattern), which can be used to correct secondary error. The electronic central ray alignment of the x-ray tube may be performed 620. The imager or detector is exposed to x-rays from the x-ray tube at a deflected position 824. The detector may be configured to measure a central ray intensity, x-ray beam power level, x-ray beam energy distribution representing the focal spot size. The measurement can occur at a pixel or a region of the detector. The image of the x-ray detector with the intensity or power level is processed 826 by a processor in the x-ray detector or the system control unit, and the processor calculates a size correction (or size correction value or size adjustment) representing an x-ray intensity difference between the deflected central ray (i.e., actual deflected central ray size) and the central ray at a specified reference position (i.e., the targeted deflected central ray size with or without the size correction) 828. In one example, the size correction is associated with a tube voltage and tube current combination for each deflected position. The processor determines if the deflected central ray size (with or without the size correction) is within an acceptable tolerance or intensity 830.

If the size correction is not within an acceptable tolerance or intensity, the size correction is added to the focusing value (e.g., used to generate a specified focal spot size) and an existing size correction (if any) 832. The focusing magnetics adjust the focal spot by the adjusted or corrected focusing size value that includes the size correction and the detector is exposed with the adjusted deflected central ray 834, and the process repeats until the size correction is within an acceptable tolerance or intensity for the deflected position. In an example, the size correction can be applied to the focusing magnetics using a focusing signal generated from the TCU. Once the size correction is within an acceptable tolerance or intensity, the size correction can be saved as a fine adjustment value 836. The size correction can be saved in the TCU associated with the x-ray tube. In an example, a different size corrections can be calculated with each tube voltage and tube current combination.

Typically, focal spot focusing occurs before focal spot steering with the focusing magnetics located before the steering magnetics relative to the electron beam. If both the focal spot size 820 and the focal spot position 800 are electronically adjusted, the electronic adjustment of the focal spot size 820 can occur before the electronic adjustment of the focal spot position 800 (either per position or per x-ray detector).

Although electronic calibration or adjustment of focal spot position (or central ray position) or electronic calibration of focal spot size (or central ray intensity or x-ray beam energy distribution) is discussed for position correction and size correction relative to differences between flat x-ray detectors and curved x-ray detectors, the mechanisms and techniques described can be applied to other features that cause distortions and errors. For example, one type of error generated as a result deflection is the geometric distortion of the focal spot due to the electron beam impinging on different areas of the curved, angled target track surface of the anode, which can cause some distortions and errors in focal spot position or size. The tube calibration (496 of FIGS. 24 and 25A) or the steering position calibration data (486 of FIGS. 24 and 25B) may correct the errors and distortions due to the rounded surface of the anode target. In some examples, tube calibration or the steering position calibration data may not adequately compensate for the distortions and errors due to the curvature of the anode. Alternatively or additionally, the electronic calibration of focal spot position and size may be used to provide greater precision to focal spot position or size and better image resolution.

Combining the processes shown in FIGS. 32 and 36, the electron beam can be steered to one of the predefined positions and an image is acquired. The image data are processed and respective correction or calibration parameters are calculated. The process is repeated until the focal spot size and deflection are within a defined limit or tolerance. Once the focal spot size and deflection for a particular tube parameter setting is calibrated, the calibration values are stored and the next position can be calibrated. The positions may be defined by a user, and as such, the processes described allows the user to tailor or calibrate each positions to the imaging techniques the user desires to achieve.

In some examples, the calibration of the focal spot size or position can be performed in manual mode in which the operator or user commands the electron beam to a specific positon, which in turn causes the x-ray beam to be emitted at a certain position. Data are acquired and the focal spot size and deflection distance can be accessed, measured, or determined. The measured data can then be used to determine the needed adjustments. The calibration process can also be run in an automated mode allowing the user or operator to make adjustment for the enhancement of image quality without the expense and time of calling a service technician. By calibration process, individual positions can be optimized and the parameters used to generate the optimized positions can be stored in the TCU for use during various procedures (e.g., patient exams). In an automated mode, applications (e.g., scanner system software) may be used to control the x-ray detector or extract the relevant information from the x-ray detector or system control unit. In another example, the focal spot size error and the deflection error can be corrected dynamically, such as when the electron beam is moving from one position to the next position. Electronic calibration of focal spot position or electronic calibration of focal spot size includes a mechanism for adjustment and adjustment verification that can be automated so the operator or user is able to verify the correct position and focal spot size without the intervention of a service technician. If a recalibration is needed the user or operator can make adjustments or start the automated calibration procedure to eliminate or reduce the detected errors.

The adjustments of the deflection position and focal spot size in manual or automated mode allow fine adjustment of the electron beam and can generate "optimized" values to correct for aperture errors and other deflection errors due to curvature on the detector. Making fine adjustments to the focal spot size or deflection position allows a user (e.g., operator) to correct for distortion errors and can improve image resolution, the signal to noise ratio, and image quality.

The x-ray tube in combination with the TCU can run an automated electronic calibration procedure that includes adjustments of the focal spot position or size. The electronic calibration allows a service technician to optimize image quality during installation or service or enables the user to verify and correct calibrations or redo the calibrations on site without a service call. The position and size corrections can be made throughout the life of the x-ray tube based on user needs.

Figure 37:
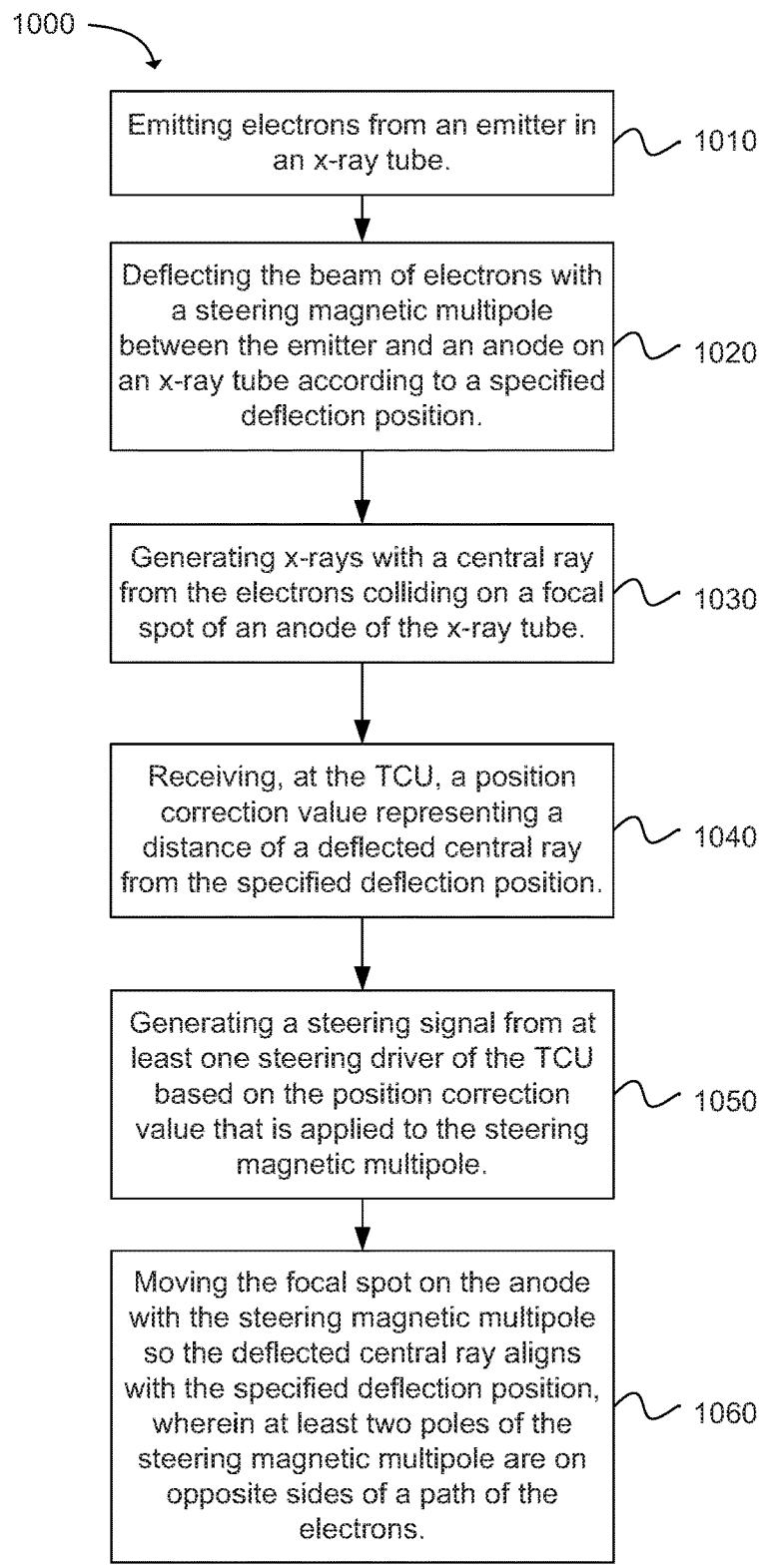
FIG. 37 is a flowchart illustrating an example of a method of adjusting a central ray of an x-ray tube to a radiation detector for positions in a focal spot deflection pattern using a tube control unit (TCU).

The flowchart shown in FIG. 37 illustrates a method 1000 of adjusting a central ray of an x-ray tube to a radiation detector for various deflected positions using a tube control unit (TCU). The method includes the step of emitting electrons from an emitter in an x-ray tube, as in step 1010. The step of deflecting the beam of electrons with a steering magnetic multipole between the emitter and an anode on an x-ray tube according to a specified deflection position follows, as in step 1020. The next step of the method includes generating x-rays with a central ray from the electrons colliding on a focal spot of an anode of the x-ray tube, as in step 1030. The method can further include receiving, at the TCU, a position correction value representing a distance of a deflected central ray from the specified deflection position, as in step 1040. The next step of the method can include generating a steering signal from at least one steering driver of the TCU based on the position correction value that is applied to the steering magnetic multipole, as in step 1050. The method can further include moving the focal spot on the anode with the steering magnetic multipole so the deflected central ray aligns with the specified deflection position, as in step 1060. At least two poles of the steering magnetic multipole are on opposite sides of a path of the electrons.

All references recited herein are incorporated herein by specific reference in their entirety.

Circuitry can include hardware, firmware, program code, executable code, computer instructions, and/or software. A non-transitory computer readable storage medium can be a computer readable storage medium that does not include a signal.

It should be understood that many of the functional units described in this description have been labeled as modules (or units), in order to more particularly emphasize their implementation independence. For example, a module may be implemented as a hardware circuit comprising custom very-large-scale integration (VLSI) circuits or gate arrays, including but not limited to logic chips, transistors, or other components. A module may also be implemented in programmable hardware devices, including but not limited to field programmable gate arrays (FPGA), programmable array logic, programmable logic devices or similar devices.

Reference throughout this specification to an "example" or an "embodiment" means that a particular feature, structure, or characteristic described in connection with the example is included in at least one embodiment of the invention. Thus, appearances of the words an "example" or an "embodiment" in various places throughout this specification are not necessarily all referring to the same embodiment.

Furthermore, the described features, structures, or characteristics may be combined in a suitable manner in one or more embodiments. In the following description, numerous specific details are provided (e.g., examples of layouts and designs) to provide a thorough understanding of embodiments of the invention. One skilled in the relevant art will recognize, however, that the invention can be practiced without one or more of the specific details, or with other methods, components, layouts, etc. In other instances, well-known structures, components, or operations are not shown or described in detail to avoid obscuring aspects of the invention.

While the forgoing examples are illustrative of the principles of the invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited. Various features and advantages of the invention are set forth in the following claims.

What is claimed is:

1. A method of aligning a central ray of an x-ray tube to a radiation imager using a tube control unit (TCU), the method comprising:
   emitting electrons from an emitter in an x-ray tube;
   generating x-rays with a central ray from the electrons colliding on a focal spot of an anode of the x-ray tube;
   receiving, at the TCU, an offset value representing a distance of the central ray from a specified imager location; and
   generating a steering signal from at least one steering driver of the TCU based on the offset value that is applied to a steering magnetic multipole between the emitter and the anode on an x-ray tube; and
   moving the focal spot on the anode with the steering magnetic multipole to align the central ray to the specified imager location, wherein at least two poles of the steering magnetic multipole are on opposite sides of a path of the electrons;
   wherein generating the steering signal further comprises:
      summing the offset value and steering position calibration data, wherein the steering position calibration data represent current values to generate at least one steering position using the steering magnetic multipole for a tube voltage and tube current combination.

2. The method of claim 1, wherein generating the steering signal further comprises:
   combining the sum of the offset value and the steering position calibration data with steering driver calibration data, wherein the steering driver calibration data represent current values of the at least one steering driver.

3. The method of claim 1, wherein generating the steering signal further comprises:
   determining a position change of the central ray from the specified imager location;
   calculating a deflection value using steering position calibration data; and
   summing the offset value representing a static position change of the central ray and the deflection value representing a dynamic position change of the central ray.

4. The method of claim 1, further comprising:
   generating a focusing signal from at least one focusing driver of the TCU that is applied to a focusing magnetic multipole between the emitter and the anode on the x-ray tube; and
   narrowing an area of the focal spot on the anode with the focusing magnetic multipole.

5. The method of claim 4, wherein generating the focusing signal further comprises:
   receiving tube calibration data from the x-ray tube, wherein the tube calibration data represent current values to generate a specified focal spot size for the x-ray tube; and
   combining the tube calibration data and focus driver calibration data, wherein the focus driver calibration data represent current values of at least one focus driver for narrowing the area of the focal spot on the anode.

6. The method of claim 1, further comprising, prior to receiving the offset value:
   receiving, at a system control unit, image data from a radiation imager including a central ray position on the radiation imager;
   calculating the offset value based on a center ray position relative to the specified imager location; and
   sending the offset value to the TCU.

7. The method of claim 6, further comprising, prior to receiving the offset value:
   detecting x-rays;
   converting detected x-rays into image data that includes the central ray position; and
   sending the image data to the system control unit.

8. The method of claim 1, further comprising:
   saving the offset value in an offset table.

9. The method of claim 1, wherein the specified imager location represents an align position of the radiation imager.

10. An x-ray system, comprising:
    an x-ray tube comprising:
       a cathode including an electron emitter configured to emit an electron beam,
       an anode configured to receive the electron beam and generate x-rays with a central ray from electrons of the electron beam colliding on a focal spot of the anode, and
       a steering magnetic multipole between the cathode and the anode that is configured to produce a steering magnetic field from a steering signal and at least two poles of the steering magnetic multipole are on opposite sides of the electron beam, wherein the steering magnetic field moves the focal spot of the electron beam on the anode; and
    a tube control unit (TCU) configured to receive an offset value and convert the offset value to the steering signal, wherein the offset value represents a distance of the central ray from a specified imager location, and the TCU comprises:
       at least one steering driver configured to generate the steering signal;
       wherein the TCU includes:
          steering position calibration data representing current values to generate at least one steering position using the steering magnetic multipole for a tube voltage and tube current combination, wherein the steering signal includes the offset value added to the steering position calibration data.

11. The x-ray system of claim 10, further comprising a system control unit configured to:
    receive image data from a radiation imager that includes a central ray position;
    calculate the offset value based on a center ray position relative to the specified imager location; and
    send the offset value to the TCU.

12. The x-ray system of claim 11, further comprising an x-ray imager configured to:
    detect x-rays;
    convert detected x-rays into image data that includes the central ray position; and
    send the image data to the system control unit.

13. The x-ray system of claim 10, wherein the steering magnetic multipole has a steering yoke with at least two evenly distributed pole projections extending from the steering yoke and oriented toward a central axis of the steering yoke and each of the at least two pole projections having a steering electromagnetic coil operably coupled to the at least one steering driver that provides a current to each steering electromagnetic coil to produce a steering magnetic field.

14. The x-ray system of claim 10, wherein:
the steering magnetic multipole includes at least two sets of steering magnetic dipoles that provides two dimensional (2D) steering of the focal spot, and a first set of the steering magnetic dipoles include two poles on opposite sides of the electron beam and a second set of the steering magnetic dipoles include another two poles on opposite sides of the electron beam, and a first path of magnetic flux from between the two poles of the first set of the steering magnetic dipoles is substantially orthogonal to a second path of magnetic flux from between the two poles of the second set of the steering magnetic dipoles; and
the at least one steering driver includes at least one horizontal driver configured to generate the steering signal to the two poles and at least one vertical driver configured to generate the steering signal to the other two poles.

15. The x-ray system of claim 10, wherein the steering magnetic multipole includes two sets of steering magnetic dipoles that have a steering yoke with four evenly distributed steering pole projections extending from the steering yoke and oriented toward a central axis of the steering yoke and each of the four steering pole projections having a steering electromagnetic coil operably coupled to the at least one steering driver that provides a current to each steering electromagnetic coil to produce a steering magnetic field.

16. The x-ray system of claim 10, wherein:
the x-ray tube further comprises a focusing magnetic multipole between the cathode and the steering magnetic multipole that is configured to produce a focusing magnetic field from a focusing signal, wherein the focusing magnetic field narrows the electron beam on a focal track of the anode; and
the TCU further comprises at least one focusing driver configured to generate the focusing signal.

17. The x-ray system of claim 16, wherein the TCU includes:
focus driver calibration data representing current values of at least one focus driver, wherein the focusing signal includes the focus driver calibration data, which represent current values of at least one focus driver for narrowing the area of the focal spot on the anode, partially iterated with tube calibration data representing current values to generate a specified focal spot size for the x-ray tube a tube voltage and tube current combination.

18. The x-ray system of claim 16, wherein the focusing magnetic multipole is disposed on the steering magnetic multipole, wherein the steering magnetic multipole is configured to produce the focusing magnetic field.

19. The x-ray system of claim 10, wherein the TCU includes:
steering driver calibration data representing current values of the at least one steering driver;
wherein the steering signal is partially iterated with the steering driver calibration data.

20. The x-ray system of claim 19, wherein:
the at least one steering position comprises multiple steering positions; and
the steering position calibration data includes data for each of the multiple steering positions.

21. The x-ray system of claim 10, wherein the x-ray system includes a computerized tomography (CT) scanner or a rotational x-ray system and further comprises a gantry configured to receive the x-ray tube and the TCU.

22. A tube control unit (TCU) configured to align an x-ray tube to an x-ray imager, comprising:
at least one steering driver configured to generate a steering signal for at least one steering coil of a steering magnetic multipole for an x-ray tube;
memory configured to store steering position calibration data representing current values to generate at least one steering position using the steering magnetic multipole for a tube voltage and tube current combination; and
a processor configured to:
receive an offset value representing a distance of a central ray of the x-ray tube from a specified imager location of an x-ray imager,
generate a deflection value using the steering position calibration data,
sum the offset value representing a static position change of the central ray and the deflection value representing a dynamic position change of the central ray, and
control the at least one steering driver to generate the steering signal for the at least one steering coil based on the sum of the offset value and the deflection value.

23. The TCU of claim 22, wherein
the memory is further configured to store steering driver calibration data that represent current values of the at least one steering driver; and
the processor is further configured to combine the sum of the offset value and the deflection value with the steering driver calibration data.

24. The TCU of claim 22, further comprising at least one focusing driver configured to generate a focusing signal for at least one focusing coil of a focusing magnetic multipole for the x-ray tube, wherein:
the memory is further configured to:
store focus driver calibration data that represent current values of the at least one focusing driver, and
store tube calibration data representing current values to generate a specified focal spot size for the x-ray tube; and
the processor is further configured to combine the tube calibration data and the focus driver calibration data.

* * * * *